United States Patent
Brosnan

(10) Patent No.: US 9,757,353 B2
(45) Date of Patent: *Sep. 12, 2017

(54) METHODS OF INDUCING ANESTHESIA

(71) Applicant: THE REGENTS OF THE UNIVERSITY OF CALIFORNIA, Oakland, CA (US)

(72) Inventor: Robert J. Brosnan, Davis, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/186,335

(22) Filed: Jun. 17, 2016

(65) Prior Publication Data

US 2016/0296496 A1 Oct. 13, 2016

Related U.S. Application Data

(63) Continuation of application No. 14/414,089, filed as application No. PCT/US2013/049985 on Jul. 10, 2013, now Pat. No. 9,381,185, which is a continuation-in-part of application No. PCT/US2013/031668, filed on Mar. 14, 2013.

(60) Provisional application No. 61/681,747, filed on Aug. 10, 2012, provisional application No. 61/670,098, filed on Jul. 10, 2012.

(51) Int. Cl.

| | | |
|---|---|---|
| *A01N 31/00* | (2006.01) |
| *A61K 31/045* | (2006.01) |
| *A61K 31/351* | (2006.01) |
| *A61K 31/357* | (2006.01) |
| *A61K 31/025* | (2006.01) |
| *A61K 31/341* | (2006.01) |
| *A61K 31/02* | (2006.01) |
| *A61K 31/08* | (2006.01) |
| *A61D 7/04* | (2006.01) |
| *A61M 16/01* | (2006.01) |
| *A61K 9/00* | (2006.01) |

(52) U.S. Cl.

CPC .............. *A61K 31/351* (2013.01); *A61D 7/04* (2013.01); *A61K 9/007* (2013.01); *A61K 31/02* (2013.01); *A61K 31/025* (2013.01); *A61K 31/045* (2013.01); *A61K 31/08* (2013.01); *A61K 31/341* (2013.01); *A61K 31/357* (2013.01); *A61M 16/01* (2013.01)

(58) Field of Classification Search

None
See application file for complete search history.

(56) References Cited

U.S. PATENT DOCUMENTS

| | | |
|---|---|---|
| 3,314,850 A | 4/1967 | Gilbert |
| 3,476,860 A | 11/1969 | Croix et al. |
| 3,683,092 A | 8/1972 | Regan et al. |
| 3,870,797 A | 3/1975 | Holdsworth et al. |
| 3,883,559 A | 5/1975 | Burdon et al. |
| 3,897,502 A | 7/1975 | Russell et al. |
| 3,954,893 A | 5/1976 | O'Neill et al. |
| 4,017,519 A | 4/1977 | Moore et al. |
| 4,060,532 A | 11/1977 | Hartmann |
| 4,088,701 A | 5/1978 | Siegemund et al. |
| 4,287,124 A | 9/1981 | Siegemund et al. |
| 4,334,105 A | 6/1982 | Terrell et al. |
| 4,346,246 A | 8/1982 | Terrell et al. |
| 4,533,741 A | 8/1985 | Squire |
| 4,762,856 A | 8/1988 | Terrell |
| 5,488,189 A | 1/1996 | Sievert et al. |
| 6,218,586 B1 | 4/2001 | Takada et al. |
| 7,067,468 B2 | 6/2006 | DeGroot et al. |
| 8,393,321 B2 | 3/2013 | Burns, Jr. et al. |
| 9,381,185 B2 * | 7/2016 | Brosnan ............... A61K 31/357 |
| 2012/0219596 A1 | 8/2012 | Limbach et al. |
| 2014/0018414 A1 | 1/2014 | Brosnan |
| 2015/0157596 A1 | 6/2015 | Brosnan |
| 2016/0113887 A1 | 4/2016 | Brosnan |

FOREIGN PATENT DOCUMENTS

| | | |
|---|---|---|
| AU | 35950/71 A | 5/1973 |
| DE | 2524956 A1 | 12/1976 |
| EP | 0 460 948 A2 | 12/1991 |
| JP | S48-28453 A | 4/1973 |
| WO | 2009/029618 A1 | 3/2009 |
| WO | 2014/011235 A1 | 1/2014 |

(Continued)

OTHER PUBLICATIONS

Altomare et al., "Highly water-soluble derivatives of the anesthetic agent propofol: in vitro and in vivo evaluation of cyclic amino acid esters," European Journal of Pharmaceutical Sciences, 2003, vol. 20, pp. 17-26.

Bagnall et al., "New Inhalation Anaesthetics: I. Fluorinated 1,3-Dioxolane Derivatives," Journal of Fluorine Chemistry, 1977, vol. 9, pp. 359-375.

Bagnall et al., "New Inhalation Anaesthetics: III. Fluorinated Aliphatic Ethers," Journal of Fluorine Chemistry, 1979, vol. 13, pp. 123-140.

Brosnan et al., "Hydrocarbon molar water solubility predicts GABA(A) and NMDA receptor modulation," Anesthesiology, 2011, American Society of Anesthesiologists Annual Meeting, 2011, A1597.

(Continued)

*Primary Examiner* — Jeffrey H Murray

(74) *Attorney, Agent, or Firm* — Kilpatrick Townsend & Stockton LLP

(57) ABSTRACT

Methods of inducing anesthesia in a subject by administering an effective amount of a compound or a mixture of compounds according to Formula I are provided. Compounds of Formula I are a class of halogenated alcohol derivatives with a vapor pressure of at least 0.1 atmospheres (76 mmHg) at 25° C. Compounds of Formula I can be administered by any route sufficient to achieve a desired anesthetic endpoint.

23 Claims, 7 Drawing Sheets

(56) References Cited

FOREIGN PATENT DOCUMENTS

| WO | 2014/011815 A2 | 1/2014 |
| WO | 2015/187918 A2 | 12/2015 |

OTHER PUBLICATIONS

Brosnan et al., "Hydrocarbon molar water solubility predicts NMDA vs. $GABA_A$ receptor modulation," BMC Pharmacology and Toxicology, Nov. 2014, vol. 15, No. 62, 13 pages.
Burns et al., "An investigation of new fluorine compounds in anaesthesia (1)," Anaesthesia, vol. 16, No. 1, Jan. 1961, 16 pages.
Burns et al., "Fluorine compounds in anaesthesia (6)," Anaesthesia, Apr. 1964, vol. 19(2), pp. 167-176.
Cromwell et al, "Forane Uptake, Excretion, and Blood Solubility in Man," Anesthesiology, vol. 35 No. 4, Oct. 1971, pp. 401-408.
Eger et al., "Dioxychlorane: A Challenge to the Correlation of Anesthetic Potency and Lipid Solubility," Anesth. Analg., vol. 60, No. 4, Apr. 1981, pp. 201-203.
Eger et al, "Nonimmobilizers and Transitional Compounds May Produce Convulsions by Two Mechanisms," Anesth Analg 1999; 884-892.
Fang et al., "Anesthetic and Convulsant Properties of Aromatic Compounds and Cycloalkanes: Implications for Mechanisms of Narcosis," Anesth Analg., 1996, vol. 83, pp. 1097-1104.
Hudlicky et al, "Practical preparation of potentially anesthetic fluorinated ethyl methyl ethers by means of bromine trifluoride and other methods," Journal of Fluorine Chemistry, vol. 102, 2000, pp. 363-367.
Ingolfsson et al., "Alcohol's Effects on Lipid Bilayer Properties," Biophysical Journal, Aug. 2011, vol. 101, pp. 847-855.
Koblin et al, "Polyhalogenated Methyl Ethyl Ethers: Solubilities and Anesthetic Properties," Anesth Analg 1999; 88:1161-1677.
Leroux et al., "a-Fluorinated Ethers, Thioethers, and Amines: Anomerically Biased Species," Chem. Rev., 2005, vol. 105, pp. 827-856.
Liu et al., "Role of GABA in the actions of ethanol in rats selectively bred for ethanol sensitivity," Pharmacology Biochemistry and Behavior, 1998, vol. 60, No. 4, pp. 793-801.
Ludvig et al., "Histological evidence for drug diffusion across the cerebral meninges into the underlying neocortex in rates," Brain Research, 2008, vol. 1188, pp. 228-232.
Massuda et al., "Breaking' and formation of hydrogen bonds by proton donor anesthetics," Can. J. Chem., vol. 55, 1977, pp. 3211-3217.
Ming et al., "Differential modulation of GABA- and NMDA-gated currents by ethanol and isoflurane in cultured rat cerebral cortical neurons," Brain Research, 2001, vol. 920, pp. 117-124.
Muffler et al. STN Entry—STN Accession No. 1983:125927; Original Publication Date: 1982; 2 pages.
Muffler et al., "Cyclization in the presence of fluoride ions. 2. 4,5-Perfluoro-1,3-dioolanes," Journal of Fluorine Chemistry, 1982; 21(2): pp. 107-132.
Nath et al., "Studies in vitro on the Effects of 1H,2H,4H(5H)-Octafluorocyclohexane and 1H,4H(2H)-Nonafluorocyclohexane on Enzymes and Organelles," Bochem. J., vol. 114, 1969, pp. 785-792.
Navarrini et al., "A new approach to the synthesis of 2,2-difluoro-1,3-dioxolanes," Journal of Fluorine Chemistry, 1995, vol. 71, pp. 111-117.
Patani et al., "Bioisosterism: A Rational Approach in Drug Design," Chem. Rev., 1996, vol. 96, pp. 3147-3176.
Rozov et al., "Asymmetric Synthesis of the Volatile Anesthetic 1,2,2,2-Tetrafluoroethyl Chlorofluoromethyl Ether Using a Stereospecific Decarboxylation of Unusual Stereochemical Outcome," J. Org. Chem., 1995, vol. 60, pp. 1319-1325.
Rudo et al, "Anaesthetic Molecules," Br. J. Anaesth., 1974, vol. 46, 181-189.
Russo et al., "Perfluoro-4-methyl-1,3-dioxole: a new monomer for high-$T_g$ amorphous fluoropolymers," Journal of Fluorine Chemistry, 2004, vol. 125, pp. 73-78.
Sako et al, "Critical Parameters and Normal Boiling Temperatures of Five Fluorinated Ethers and Two Fluorinated Ketones," J. Chem. Eng. Data, 2001, vol. 46, pp. 1078-1081.
Soares et al., "Solubility of Haloether Anesthetics in Human and Animal Blood," Anesthesiology, Jul. 2012, vol. 117(1), pp. 48-55.
Speers et al, "General Anesthetics. 2. Halogenated Methyl Isopropyl Ethers," Journal of Medicinal Chemistry, 1971, vol. 14, No. 7, pp. 593-595.
Terrell et al., "General Anesthetics. 1. Halogenated Methyl Ethyl Ethers as Anesthetic Agents," Journal of Medicinal Chemistry, 1971, vol. 14, No. 6, pp. 517-519.
Terrell et al., "General Anesthetics. 3. Fluorinated Methyl Ethyl Ethers as Anesthetic Agents," Journal of Medicinal Chemistry, 1972, vol. 15, No. 6, pp. 604-606.
Williams et al., Foye's Principals of Medicinal Chemistry, 5th Ed., 2002, pp. 59-61.

* cited by examiner

METHODS OF INDUCING ANESTHESIA

CROSS-REFERENCES TO RELATED APPLICATIONS

This patent application is a continuation of U.S. application Ser. No. 14/414,089, filed Jan. 9, 2015, which application is a National Phase application under 35 U.S.C. 371 of International Application No. PCT/US2013/049985, filed Jul. 10, 2013, which is a continuation-in-part of International Application No. PCT/US2013/031668, filed Mar. 14, 2013, which claims the benefit of priority to U.S. Provisional Patent Application No. 61/681,747, filed Aug. 10, 2012, and of U.S. Provisional Patent Application No. 61/670,098, filed Jul. 10, 2012, the contents of all of which are hereby incorporated herein by reference in their entireties.

STATEMENT AS TO RIGHTS TO INVENTIONS MADE UNDER FEDERALLY SPONSORED RESEARCH AND DEVELOPMENT

This invention was made with government support under Grant No. GM092821 awarded by National Institutes of Health. The government has certain rights in the invention.

FIELD OF THE INVENTION

The present invention provides methods for determining the selectivity of an anesthetic for an anesthetic-sensitive receptor by determining the molar water solubility of the anesthetic. The invention further provides methods for modulating the selectivity of an anesthetic for an anesthetic-sensitive receptor by altering or modifying the anesthetic to have higher or lower water solubility. The invention further provides methods of inducing anesthesia in a subject by administering via the respiratory pathways (e.g., via inhalational or pulmonary delivery) an effective amount of an anesthetic compound identified according to the present methods. The invention also provides methods of inducing sedation in a subject by administering via the respiratory pathways (e.g., via inhalational or pulmonary delivery) an effective amount of an anesthetic compound identified according to the present methods.

BACKGROUND OF THE INVENTION

Molecular Mechanisms of Anesthetic Action

All general anesthetics in common clinical use modulate either three-transmembrane (TM3) ion channels (e.g., NMDA receptors), four-transmembrane (TM4) ion channels (e.g., $GABA_A$ receptors), or members of both ion channel superfamilies. Sonner, et al., Anesth Analg (2003) 97:718-40. For example, many structurally unrelated inhaled anesthetics potentiate $GABA_A$ currents and inhibit NMDA currents. But why should a diverse group of compounds all modulate unrelated ion channels? A highly specific "induced fit" model between protein and ligand, as proposed for enzyme-substrate binding, (Koshland, Proc Natl Acad Sci USA 1958; 44: 98-104) is problematic since it implies the conservation of specific binding sites across non-homologous proteins to compounds (i.e., anesthetics) not found in nature. Sonner, Anesth Analg (2008) 107: 849-54. Moreover, promiscuous anesthetic actions on disparate receptors typically occurs at drug concentrations 50-200 times the median effective concentration (EC50) at which modulation of a single receptor class typically occurs, such as with etomidate agonism of $GABA_A$ receptors (Tomlin et al., Anesthesiology (1998) 88: 708-17; Hill-Venning, et al., Br J Pharmacol (1997) 120: 749-56; Belelli, et al., Br J Pharmacol (1996) 118: 563-76; Quast, et al., J Neurochem (1983) 41:418-25; and Franks, Br J Pharmacol 2006; 147 Suppl 1: S72-81) or dizocilpine (MK-801) antagonism of NMDA receptors. Wong, et al., Proc Natl Acad Sci USA (1986) 83: 7104-8; Ransom, et al., Brain Res (1988) 444: 25-32; and Sircar, et al., Brain Res (1987) 435: 235-40. It is unknown what molecular properties confer specificity for a single receptor (or members of a single receptor superfamily) and what properties allow other anesthetics to modulate multiple unrelated receptors. However, since ion channel modulation is important to conferring desirable anesthetic efficacy—as well as undesirable drug side effects—it is desirable to know what factors influence anesthetic receptor specificity in order to develop new and safer agents.

Anesthetics and Specific Ion Channel Targets

General anesthetics mediate central nervous system depression through actions on cell membrane receptors and channels which have a net hyperpolarizing effect on neurons. Sonner, et al., Anesth Analg (2003) 97:718-40; Grasshoff, et al., Eur J Anaesthesiol (2005) 22: 467-70; Franks, Br J Pharmacol (2006) 147 Suppl 1: S72-81; 33; Hemmings, et al., Trends Pharmacol Sci (2005) 26: 503-10; and Forman, et al., Int Anesthesiol Clin (2008) 46: 43-53. Although anesthetics partition into cell membranes as a function of lipid solubility, it is through competitive protein binding that these agents most likely produce anesthetic effects. In fact, general anesthetics have been shown to competitively inhibit functions of membrane-free enzymes (Franks, et al., Nature (1984) 310: 599-601), indicating that the lipid phase is not essential for anesthetic modulation of protein function. Specific high-affinity binding sites have been identified for some of these anesthetics. For example, apropofol (Jewett, et al., Anesthesiology (1992) 77: 1148-54; Bieda, et al., J Neurophysiol (2004) 92: 1658-67; Peduto, et al., Anesthesiology 1991; 75: 1000-9; Sonner, et al, Anesth Analg (2003) 96: 706-12; and Dong et al., Anesth Analg (2002) 95: 907-14), etomidate (Flood, et al., Anesthesiology (2000) 92: 1418-25; Zhong, et al., Anesthesiology 2008; 108: 103-12; O'Meara, et al., Neuroreport (2004) 15: 1653-6), and thiopental (Jewett, et al., Anesthesiology (1992) 77: 1148-54; Bieda, et al, J Neurophysiol (2004) 92: 1658-67; Yang, et al., Anesth Analg (2006) 102: 1114-20) all potently potentiate $GABA_A$ receptor currents, and their anesthetic effects are potently antagonized or prevented by $GABA_A$ receptor antagonists, such as pictotoxin or bicuculline. Ketamine produces anesthesia largely (but not entirely) through its antagonism of NMDA receptors. Harrison et al., Br J Pharmacol (1985) 84: 381-91; Yamamura, et al., Anesthesiology (1990) 72: 704-10; and Kelland, et al., Physiol Behav (1993) 54: 547-54. Dexmedetomidine is a specific a2 adrenoreceptor agonist that is antagonized by specific a2 adrenoreceptor antagonists, such as atipamezole. Doze, et al., Anesthesiology (1989) 71: 75-9; Karhuvaara, et al., Br J Clin Pharmacol (1991) 31: 160-5; and Correa-Sales, et al., Anesthesiology (1992) 76: 948-52. It is probably not by coincidence that anesthetics for which a single receptor contributes to most or all of the anesthetic effect also have low aqueous $ED_{50}$ values (see, Table 1).

TABLE 1

Aqueous phase $EC_{50}$ for several anesthetics.

| Anesthetic | Aqueous $EC_{50}$ (μM) | Species | Reference |
|---|---|---|---|
| Propofol | 2 | Rat | Tonner et al., *Anesthesiology* (1992) 77: 926-31 |
| Ketamine | 2 | Human | Flood, et al., *Anesthesiology* (2000) 92: 1418-25 |
| Etomidate | 3 | Tadpole | Tomlin, et al., *Anesthesiology* (1998) 88: 708-17 |
| Dexmedetomidine | 7 | Tadpole | Tonner, et al., *Anesth Analg* (1997) 84: 618-22 |
| Thiopental | 25 | Human | Flood, et al., *Anesthesiology* (2000) 92: 1418-25 |
| Methoxyflurane | 210 | Tadpole | Franks, et al., *Br J Anaesth* (1993) 71: 65-76 |
| Halothane | 230 | Tadpole | Franks, et al., *Br J Anaesth* (1993) 71: 65-76 |
| Isoflurane | 290 | Tadpole | Franks, et al., *Br J Anaesth* (1993) 71: 65-76 |
| Chloroform | 1300 | Tadpole | Franks, et al., *Br J Anaesth* (1993) 71: 65-76 |
| Diethyl ether | 25000 | Tadpole | Franks, et al., *Br J Anaesth* (1993) 71: 65-76 |

Ion channel mutations, either in vitro or in vivo, dramatically alter anesthetic sensitivity, not only for the very potent and specific agents, but also for the inhaled anesthetics. Several mutations in the $GABA_A$ (Hara, et al., *Anesthesiology* 2002; 97: 1512-20; Jenkins, et al., *J Neurosci* 2001; 21: RC136; Krasowski, et al., *Mol Pharmacol* 1998; 53: 530-8; Scheller, et al., *Anesthesiology* 2001; 95: 123-31; Nishikawa, et al., *Neuropharmacology* 2002; 42: 337-45; Jenkins, et al., *Neuropharmacology* 2002; 43: 669-78; Jurd, et al., *FASEB J* 2003; 17: 250-2; Kash, et al., *Brain Res* 2003; 960: 36-41; Borghese, et al., *J Pharmacol Exp Ther* 2006; 319: 208-18; Drexler, et al., *Anesthesiology* 2006; 105: 297-304) or NMDA (Ogata, et al., *J Pharmacol Exp Ther* (2006) 318: 434-43; Dickinson, et al., *Anesthesiology* 2007; 107: 756-67) receptor can decrease responses to isoflurane, halothane, and other volatile anesthetics. Although mutations that render receptors insensitive to anesthetics could suggest a single site that is responsible for binding a specific drug, it need not be the case. Most of these mutations are believed to reside near lipid-water interfaces, either in amphiphilic protein pockets (Bertaccini et al., *Anesth Analg* (2007) 104: 318-24; Franks, et al., *Nat Rev Neurosci* (2008) 9: 370-86) or near the outer lipid membrane. It is possible that an anesthetic could be excluded from its protein interaction site because of size. However, it is also possible that the mutation substantially increases (but does not entirely exclude) the number of "non-specific" low-affinity anesthetic-protein interactions necessary to modulate the receptor. In this case, modulation of the mutant receptor will either only occur at anesthetic concentrations in excess of the wild-type minimum alveolar concentration (MAC) (Eger, et al., *Anesthesiology* (1965) 26: 756-63) or, if the drug is insufficiently soluble at the active site to allow a sufficient number of "non-specific" interactions with the mutant protein, no receptor modulation will be possible even at saturating aqueous drug concentrations.

Another argument for specific "induced fit" binding sites on ion channels is the "cut-off" effect. For example, increasing the carbon chain length of an alkanol increases lipid solubility and anesthetic potency, as predicted by the Meyer-Overton hypothesis (Overton C E: Studies of Narcosis. London, Chapman and Hall, 1991), until a 12-carbon chain length (dodecanol) is reached (Alifimoff, et al., *Br J Phar-macol* (1989) 96: 9-16). Alkanols with a longer chain length were not anesthetics (hence, a "cut-off" effect at C=13 carbons). However, the hydrocarbon chain length needed to reach the cut-off effect is C=9 for alkanes (Liu, et al., *Anesth Analg* (1993) 77: 12-8), C=2 for perfluorinated alkanes (Liu, et al., *Anesth Analg* (1994) 79: 238-44), and C=3 for perfluorinated methyl ethyl ethers (Koblin, et al., *Anesth Analg* (1999) 88: 1161-7). If size is essential to access a specific anesthetic binding site, then why is the "cut-off" chain length not constant? At the cellular level, straight-chain alcohols can maximally inhibit NMDA receptor function up to octanol with complete cut-off at C=10. But straight-chain 1, Ω-diols maximally inhibit NMDA receptors up to decanol, with complete cut-off not observed until C=16 (Peoples, et al., *Mol Pharmacol* (2002) 61: 169-76). Increasing hydrocarbon chain length does not only increase molecular volume, but also decreases water solubility. The cut-off effect therefore refers to a minimum water solubility necessary to produce an effect, rather than a maximum molecular size.

At the tens of micromolar concentrations or less, anesthetics most likely exert their effects on ion channels by specific binding to relatively high-affinity sites on proteins to induce a conformational change that alters ion conductance, either alone or in the presence of another endogenous ligand. However, these agents can still interact with other receptors (or the same receptor at different sites) if present in higher concentrations. For example, assume that two dissimilar receptors (R1 and R2) each can exert an anesthetic effect. Assuming that efficacy of a drug at R1=1, that R1 is able to produce a full anesthetic effect in isolation, and that the EC99 of R1 is less than the EC1 of R2, then this drug will produce anesthesia by selectively modulating R1. However, if any of these assumptions is not true, then some contribution of R2 will be required to produce an anesthetic effect (FIG. 1).

Many injectable anesthetics seem to follow the example described above. Propofol is a positive modulator of $GABA_A$ receptor currents with an EC50 around 60 μM (Hill-Venning, et al., *Br J Pharmacol* (1997) 120: 749-56; Prince, et al., *Biochem Pharmacol* (1992) 44: 1297-302; Orser, et al., *J Neurosci* (1994) 14: 7747-60; Reynolds, et al., *Eur J Pharmacol* (1996) 314: 151-6), and propofol is believed to mediate the majority of its anesthetic effects through potentiation of $GABA_A$ currents (Sonner, et al, *Anesth Analg* (2003) 96: 706-12). However, propofol also inhibits currents from the unrelated NMDA receptor with an IC50 of 160 μM (Orser, et al., *Br J Pharmacol* (1995) 116: 1761-8). Ketamine produces anesthesia largely through antagonism of NMDA receptors, which it inhibits with an IC50 of 14 μM (Liu, et al., *Anesth Analg* (2001) 92: 1173-81), although 365 μM ketamine also increases unrelated 4 transmembrane $GABA_A$ receptor currents by 56% (Lin, et al., *J Pharmacol Exp Ther* (1992) 263: 569-78). In these cases, it seems plausible that 2 different types of interactions (for high- vs. low-affinity responses) could occur on a single receptor to produce the same qualitative effect. In contrast, volatile inhaled anesthetics generally have little or no effect on $GABA_A$ and NMDA receptors at aqueous phase concentrations <50 μM (Lin, et al., *J Pharmacol Exp Ther* (1992) 263: 569-78; Moody, et al., *Brain Res* (1993) 615: 101-6; Harris, et al., *J Pharmacol Exp Ther* (1993) 265: 1392-8; Jones, et al., *J Physiol* (1992) 449: 279-93; Hall, et al., *Br J Pharmacol* (1994) 112: 906-10). It is possible that these agents are not specific ligands for any anesthetic-sensitive receptor that is relevant to immobility; thus they may rely only on nonspecific protein-ligand interactions that, in turn, may be reflected in the higher aqueous phase concentrations of these agents required for anesthesia (Table 1).

BRIEF SUMMARY OF THE INVENTION

In one aspect, the invention provides methods of inducing anesthesia in a subject. In some embodiments, the methods comprise administering to the subject via the respiratory system an effective amount of a compound or a mixture of compounds of Formula I:

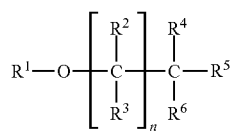

wherein:
n is 0-4,
$R^1$ is H;
$R^2, R^3, R^4, R^5$ and $R^6$ independently are selected from H, X, $CX_3$, $CHX_2$, $CH_2X$ and $C_2X_5$; and
wherein X is a halogen, the compound having vapor pressure of at least 0.1 atmospheres (76 mmHg) at 25° C., and the number of hydrogen atoms in Formula I do not exceed the number of carbon atoms, thereby inducing anesthesia in the subject. In various embodiments, X is a halogen selected from the group consisting of F, Cl, Br and I. In some embodiments, X is F. In some embodiments, $R^1$ is selected from H, $CH_2OH$, CHFOH and $CF_2OH$, CHClOH, $CCl_2OH$ and CFClOH. In some embodiments, $R^2, R^3, R^4, R^5$ and $R^6$ independently are selected from H, F, Cl, Br, I, $CF_3$, $CHF_2$, $CH_2F$, $C_2F_5$, $CCl_3$, $CHCl_2$, $CH_2Cl$, $C_2Cl_5$, $CCl_2F$, $CClF_2$, CHClF, $C_2ClF_4$, $C_2Cl_2F_3$, $C_2Cl_3F_2$, and $C_2Cl_4F$. In some embodiments, the compound is selected from the group consisting of:
a) Methanol, 1-fluoro-1-[2,2,2-trifluoro-1-(trifluoromethyl) ethoxy]- (CAS#1351959-82-4);
b) 1-Butanol, 4,4,4-trifluoro-3,3-bis(trifluoromethyl)- (CAS#14115-49-2);
c) 1-Butanol, 1,1,2,2,3,3,4,4,4-nonafluoro- (CAS#3056-01-7);
d) 1-Butanol, 2,2,3,4,4,4-hexafluoro-3-(trifluoromethyl)- (CAS#782390-93-6);
e) 1-Butanol, 3,4,4,4-tetrafluoro-3-(trifluoromethyl)- (CAS#90999-87-4);
f) 1-Pentanol, 1,1,4,4,5,5,5-heptafluoro- (CAS#313503-66-1); and
g) 1-Pentanol, 1,1,2,2,3,3,4,4,5,5,5-undecafluoro- (CAS#57911-98-5).

In a further aspect, the invention provides methods of inducing anesthesia in a subject. In some embodiments, the methods comprise administering to the subject via the respiratory system an effective amount of a compound or a mixture of compounds of Formula II:

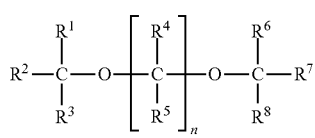

wherein:
n is 1-3,
$R^1, R^2, R^3, R^4, R^5, R^6, R^7$ and $R^8$ independently are selected from H, X, $CX_3$, $CHX_2$, $CH_2X$ and $C_2X_5$; and
wherein X is a halogen, the compound having vapor pressure of at least 0.1 atmospheres (76 mmHg) at 25° C., and the number of hydrogen atoms in Formula II do not exceed the number of carbon atoms, thereby inducing anesthesia in the subject. In various embodiments, X is a halogen selected from the group consisting of F, Cl, Br and I. In some embodiments, X is F. In some embodiments, $R^1, R^2, R^3, R^4, R^5, R^6, R^7$ and $R^8$ independently are selected from H, F, Cl, Br, I, $CF_3$, $CHF_2$, $CH_2F$, $C_2F_5$, $CCl_3$, $CHCl_2$, $CH_2Cl$, $C_2Cl_5$, $CCl_2F$, $CClF_2$, CHClF, $C_2ClF_4$, $C_2Cl_2F_3$, $C_2Cl_3F_2$, and $C_2Cl_4F$. In some embodiments, the compound is selected from the group consisting of:
a) Ethane, 1,1,2-trifluoro-1,2-bis(trifluoromethoxy)- (CAS#362631-92-3);
b) Ethane, 1,1,1,2-tetrafluoro-2,2-bis(trifluoromethoxy)- (CAS#115395-39-6);
c) Ethane, 1-(difluoromethoxy)-1,1,2,2-tetrafluoro-2-(trifluoromethoxy)- (CAS#40891-98-3);
d) Ethane, 1,1,2,2-tetrafluoro-1,2-bis(trifluoromethoxy)- (CAS#378-11-0);
e) Ethane, 1,2-difluoro-1,2-bis(trifluoromethoxy)- (CAS#362631-95-6);
f) Ethane, 1,2-bis(trifluoromethoxy)-(CAS#1683-90-5);
g) Propane, 1,1,3,3-tetrafluoro-1,3-bis(trifluoromethoxy)- (CAS#870715-97-2);
h) Propane, 2,2-difluoro-1,3-bis(trifluoromethoxy)- (CAS#156833-18-0);
i) Propane, 1,1,1,3,3-pentafluoro-3-methoxy-2-(trifluoromethoxy)- (CAS#133640-19-4;
j) Propane, 1,1,1,3,3,3-hexafluoro-2-(fluoromethoxymethyl)- (CAS#124992-92-3); and
k) Propane, 1,1,1,2,3,3-hexafluoro-3-methoxy-2-(trifluoromethoxy)- (CAS#104159-55-9).

In another aspect, the invention provides methods of inducing anesthesia in a subject. In some embodiments, the methods comprise administering to the subject via the respiratory system an effective amount of a compound or a mixture of compounds of Formula III:

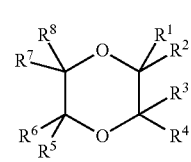

wherein:
$R^1, R^2, R^3, R^4, R^5, R^6, R^7$ and $R^8$ independently are selected from H, X, $CX_3$, $CHX_2$, $CH_2X$ and $C_2X_5$; and
wherein X is a halogen, the compound has a vapor pressure of at least 0.1 atmospheres (76 mmHg) at 25° C., and the number of hydrogen atoms of Formula III do not exceed the number of carbon atoms, thereby inducing anesthesia in the subject. In various embodiments, X is a halogen selected from the group consisting of F, Cl, Br and I. In some embodiments, X is F. In some embodiments, $R^1, R^2, R^3, R^4, R^5, R^6, R^7$ and $R^8$ independently are selected from H, F, Cl, Br, I, $CF_3$, $CHF_2$, $CH_2F$, $C_2F_5$, $CCl_3$, $CHCl_2$, $CH_2Cl$, $C_2Cl_5$, $CCl_2F$, $CClF_2$, CHClF, $C_2ClF_4$, $C_2Cl_2F_3$, $C_2Cl_3F_2$, and C₂Cl₄F. In some embodiments, the compound is selected from the group consisting of:
a) 1,4-Dioxane, 2,2,3,3,5,6-hexafluoro- (CAS#362631-99-0);
b) 1,4-Dioxane, 2,3-dichloro-2,3,5,5,6,6-hexafluoro- (CAS#135871-00-0);
c) 1,4-Dioxane, 2,3-dichloro-2,3,5,5,6,6-hexafluoro-, trans- (9CI) (CAS#56625-45-7);
d) 1,4-Dioxane, 2,3-dichloro-2,3,5,5,6,6-hexafluoro-, cis- (9CI) (CAS#56625-44-6);
e) 1,4-Dioxane, 2,2,3,5,6,6-hexafluoro- (CAS#56269-26-2);
f) 1,4-Dioxane, 2,2,3,5,5,6-hexafluoro- (CAS#56269-25-1);
g) 1,4-Dioxane, 2,2,3,3,5,6-hexafluoro-, trans- (9CI) (CAS#34206-83-2);
h) 1,4-Dioxane, 2,2,3,5,5,6-hexafluoro-, cis- (9CI) (CAS#34181-52-7);
i) p-Dioxane, 2,2,3,5,5,6-hexafluoro-, trans- (8CI) (CAS#34181-51-6);
j) 1,4-Dioxane, 2,2,3,5,5,6-hexafluoro-, cis- (9CI) (CAS#34181-50-5);
k) p-Dioxane, 2,2,3,5,5,6-hexafluoro-, trans- (8CI) (CAS#34181-49-2);
l) 1,4-Dioxane, 2,2,3,3,5,6-hexafluoro-, (5R,6S)-rel- (CAS#34181-48-1);
m) 1,4-Dioxane, 2,2,3,3,5,5,6-heptafluoro- (CAS#34118-18-8); and
n) 1,4-Dioxane, 2,2,3,3,5,5,6,6-octafluoro- (CAS#32981-22-9).

In another aspect, the invention provides methods of inducing anesthesia in a subject. In some embodiments, the methods comprise administering to the subject via the respiratory system an effective amount of a compound or a mixture of compounds of Formula IV:

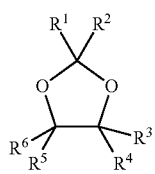

IV wherein:
$R^1$, $R^2$, $R^3$, $R^4$, $R^5$ and $R^6$ independently are selected from H, X, $CX_3$, $CHX_2$, $CH_2X$ and $C_2X_5$; and
wherein X is a halogen, the compound has a vapor pressure of at least 0.1 atmospheres (76 mmHg) at 25° C., and the number of hydrogen atoms of Formula IV do not exceed the number of carbon atoms, thereby inducing anesthesia in the subject. In various embodiments, X is a halogen selected from the group consisting of F, Cl, Br and I. In some embodiments, X is F. In some embodiments, $R^1$, $R^2$, $R^3$, $R^4$, $R^5$ and $R^6$ independently are selected from H, F, Cl, Br, I, $CF_3$, $CHF_2$, $CH_2F$, $C_2F_5$, $CCl_3$, $CHCl_2$, $CH_2Cl$, $C_2Cl_5$, $CCl_2F$, $CClF_2$, $CHClF$, $C_2ClF_4$, $C_2Cl_2F_3$, $C_2Cl_3F_2$, and $C_2Cl_4F$. In some embodiments, the compound is selected from the group consisting of:
a) 1,3-Dioxolane, 2,4,4,5-tetrafluoro-5-(trifluoromethyl)- (CAS#344303-08-8);
b) 1,3-Dioxolane, 2-chloro-4,4,5-trifluoro-5-(trifluoromethyl)- (CAS#344303-05-5);
c) 1,3-Dioxolane, 4,4,5,5-tetrafluoro-2-(trifluoromethyl)- (CAS#269716-57-6);
d) 1,3-Dioxolane, 4-chloro-2,2,4-trifluoro-5-(trifluoromethyl)- (CAS#238754-29-5);
e) 1,3-Dioxolane, 4,5-dichloro-2,2,4,5-tetrafluoro-, trans- (9CI) (CAS#162970-78-7);
f) 1,3-Dioxolane, 4,5-dichloro-2,2,4,5-tetrafluoro-, cis- (9CI) (CAS#162970-76-5);
g) 1,3-Dioxolane, 4-chloro-2,2,4,5,5-pentafluoro- (CAS#139139-68-7);
h) 1,3-Dioxolane, 4,5-dichloro-2,2,4,5-tetrafluoro- (CAS#87075-00-1);
i) 1,3-Dioxolane, 2,4,4,5-tetrafluoro-5-(trifluoromethyl)-, trans- (9CI) (CAS#85036-66-4);
j) 1,3-Dioxolane, 2,4,4,5-tetrafluoro-5-(trifluoromethyl)-, cis- (9CI) (CAS#85036-65-3);
k) 1,3-Dioxolane, 2-chloro-4,4,5-trifluoro-5-(trifluoromethyl)-, trans- (9CI) (CAS#85036-60-8);
l) 1,3-Dioxolane, 2-chloro-4,4,5-trifluoro-5-(trifluoromethyl)-, cis- (9CI) (CAS#85036-57-3);
m) 1,3-Dioxolane, 2,2-dichloro-4,4,5,5-tetrafluoro- (CAS#85036-55-1);
n) 1,3-Dioxolane, 4,4,5-trifluoro-5-(trifluoromethyl)- (CAS#76492-99-4);
o) 1,3-Dioxolane, 4,4-difluoro-2,2-bis(trifluoromethyl)- (CAS#64499-86-1);
p) 1,3-Dioxolane, 4,5-difluoro-2,2-bis(trifluoromethyl)-, cis- (9CI) (CAS#64499-85-0);
q) 1,3-Dioxolane, 4,5-difluoro-2,2-bis(trifluoromethyl)-, trans- (9CI) (CAS#64499-66-7);
r) 1,3-Dioxolane, 4,4,5-trifluoro-2,2-bis(trifluoromethyl)- (CAS#64499-65-6);
s) 1,3-Dioxolane, 2,4,4,5,5-pentafluoro-2-(trifluoromethyl)- (CAS#55135-01-8);
t) 1,3-Dioxolane, 2,2,4,4,5,5-hexafluoro- (CAS#21297-65-4); and
u) 1,3-Dioxolane, 2,2,4,4,5-pentafluoro-5-(trifluoromethyl)- (CAS#19701-22-5).

In another aspect, the invention provides methods of inducing anesthesia in a subject. In some embodiments, the methods comprise administering to the subject via the respiratory system an effective amount of a compound or a mixture of compounds of Formula V:

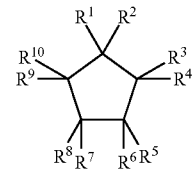

V wherein:
$R^1$, $R^2$, $R^3$, $R^4$, $R^5$, $R^6$, $R^7$, $R^8$, $R^9$ and $R^{10}$ independently are selected from H, X, $CX_3$, $CHX_2$, $CH_2X$ and $C_2X_5$; and
wherein X is a halogen, the compound has a vapor pressure of at least 0.1 atmospheres (76 mmHg) at 25° C., and the number of hydrogen atoms of Formula V do not exceed the number of carbon atoms, thereby inducing anesthesia in the subject. In various embodiments, X is a halogen selected from the group consisting of F, Cl, Br and I. In some embodiments, X is F. In some embodiments, $R^1$, $R^2$, $R^3$, $R^4$, $R^5$, $R^6$, $R^7$, $R^8$, $R^9$ and $R^{10}$ independently are selected from H, F, Cl, Br, I, $CF_3$, $CHF_2$, $CH_2F$, $C_2F_5$, $CCl_3$, $CHCl_2$, $CH_2Cl$, $C_2Cl_5$, $CCl_2F$, $CClF_2$, $CHClF$, $C_2ClF_4$, $C_2Cl_2F_3$, $C_2Cl_3F_2$, and C₂Cl₄F. In some embodiments, the compound is selected from the group consisting of:
a) Cyclopentane, 5-chloro-1,1,2,2,3,3,4,4-octafluoro- (CAS#362014-70-8);
b) Cyclopentane, 1,1,2,2,3,4,4,5-octafluoro- (CAS#773-17-1);
c) Cyclopentane, 1,1,2,2,3,3,4,5-octafluoro- (CAS#828-35-3);
d) Cyclopentane, 1,1,2,3,3,4,5-heptafluoro- (CAS#3002-03-7);
e) Cyclopentane, 1,1,2,2,3,3,4,4-octafluoro- (CAS#149600-73-7);
f) Cyclopentane, 1,1,2,2,3,4,5-heptafluoro- (CAS#1765-23-7);
g) Cyclopentane, 1,1,2,3,4,5-hexafluoro- (CAS#699-38-7);
h) Cyclopentane, 1,1,2,2,3,3,4-heptafluoro- (CAS#15290-77-4);
i) Cyclopentane, 1,1,2,2,3,4-hexafluoro- (CAS#199989-36-1);
j) Cyclopentane, 1,1,2,2,3,3-hexafluoro- (CAS#123768-18-3); and
k) Cyclopentane, 1,1,2,2,3-pentafluoro- (CAS#1259529-57-1). In some embodiments, the compound is selected from the group consisting of:
c) Cyclopentane, 1,1,2,2,3,3,4,5-octafluoro- (CAS#828-35-3);
e) Cyclopentane, 1,1,2,2,3,3,4,4-octafluoro- (CAS#149600-73-7); and
h) Cyclopentane, 1,1,2,2,3,3,4-heptafluoro- (CAS#15290-77-4).

In another aspect, the invention provides methods of inducing anesthesia in a subject. In some embodiments, the methods comprise administering to the subject via the respiratory system an effective amount of 1,1,2,2,3,3,4,4-octafluoro-cyclohexane (CAS#830-15-9), thereby inducing anesthesia in the subject.

In another aspect, the invention provides methods of inducing anesthesia in a subject. In some embodiments, the methods comprise administering to the subject via the respiratory system an effective amount of a compound or a mixture of compounds of Formula VI:

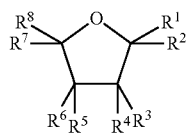

wherein:
R¹, R², R³, R⁴, R⁵, R⁶, R⁷ and R⁸ independently are selected from H, X, CX₃, CHX₂, CH₂X and C₂X₅; and
wherein X is a halogen, the compound has a vapor pressure of at least 0.1 atmospheres (76 mmHg) at 25° C., and the number of hydrogen atoms of Formula VI do not exceed the number of carbon atoms, thereby inducing anesthesia in the subject. In various embodiments, X is a halogen selected from the group consisting of F, Cl, Br and I. In some embodiments, X is F. In some embodiments, R¹, R², R³, R⁴, R⁵, R⁶, R⁷ and R⁸ independently are selected from H, F, Cl, Br, I, CF₃, CHF₂, CH₂F, C₂F₅, CCl₃, CHCl₂, CH₂Cl, C₂Cl₅, CCl₂F, CClF₂, CHClF, C₂ClF₄, C₂Cl₂F₃, C₂Cl₃F₂, and C₂Cl₄F. In some embodiments, the compound is selected from the group consisting of:
a) Furan, 2,3,4,4-tetrafluorotetrahydro-2,3-bis(trifluoromethyl)- (CAS#634191-25-6);
b) Furan, 2,2,3,3,4,4,5-heptafluorotetrahydro-5-(trifluoromethyl)- (CAS#377-83-3);
c) Furan, 2,2,3,3,4,5,5-heptafluorotetrahydro-4-(trifluoromethyl)- (CAS#374-53-8);
d) Furan, 2,2,3,4,5-pentafluorotetrahydro-5-(trifluoromethyl)-, (2a,3β,4a)- (9CI) (CAS#133618-53-8);
e) Furan, 2,2,3,4,5-pentafluorotetrahydro-5-(trifluoromethyl)-, (2a,3a,4β)- (CAS#133618-52-7);
f) Furan, 2,2,3,4,5-pentafluorotetrahydro-5-(trifluoromethyl)-, (2α,3β,4α)- (9CI) (CAS#133618-53-8);
g) Furan, 2,2,3,4,5-pentafluorotetrahydro-5-(trifluoromethyl)-, (2α,3α,4β)- (9CI) (CAS#133618-52-7);
h) Furan, 2,2,3,3,5,5-hexafluorotetrahydro-4-(trifluoromethyl)- (CAS#61340-70-3);
i) Furan, 2,3-difluorotetrahydro-2,3-bis(trifluoromethyl)- (CAS#634191-26-7);
j) Furan, 2-chloro-2,3,3,4,4,5,5-heptafluorotetrahydro- (CAS#1026470-51-8);
k) Furan, 2,2,3,3,4,4,5-heptafluorotetrahydro-5-methyl- (CAS#179017-83-5);
l) Furan, 2,2,3,3,4,5-hexafluorotetrahydro-5-(trifluoromethyl)-, trans- (9CI) (CAS#133618-59-4); and
m) Furan, 2,2,3,3,4,5-hexafluorotetrahydro-5-(trifluoromethyl)-, cis- (9CI) (CAS#133618-49-2).

In another aspect, the invention provides methods of inducing anesthesia in a subject. In some embodiments, the methods comprise administering to the subject via the respiratory system an effective amount of a compound or mixture of compounds of Formula VII:

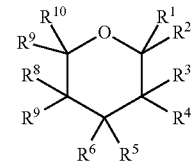

wherein:
R¹, R², R³, R⁴, R⁵, R⁶, R⁷, R⁸, R⁹ and R¹⁰ independently are selected from H, X, CX₃, CHX₂, CH₂X, and C₂X₅; and
wherein X is a halogen, the compound has a vapor pressure of at least 0.1 atmospheres (76 mmHg) at 25° C., and the number of hydrogen atoms of Formula VII do not exceed the number of carbon atoms, thereby inducing anesthesia in the subject. In various embodiments, X is a halogen selected from the group consisting of F, Cl, Br and I. In some embodiments, X is F. In some embodiments, R¹, R², R³, R⁴, R⁵, R⁶, R⁷, R⁸, R⁹ and R¹⁰ independently are selected from H, F, Cl, Br, I, CF₃, CHF₂, CH₂F, C₂F₅, CCl₃, CHCl₂, CH₂Cl, C₂Cl₅, CCl₂F, CClF₂, CHClF, C₂ClF₄, C₂Cl₂F₃, C₂Cl₃F₂, and C₂Cl₄F. In some embodiments, the compound is selected from the group consisting of:
a) 2H-Pyran, 2,2,3,3,4,4,5,5,6,6-nonafluorotetrahydro-4- (CAS#71546-79-7);
b) 2H-Pyran, 2,2,3,3,4,4,5,5,6-nonafluorotetrahydro-6-(trifluoromethyl)- (CAS#356-47-8);
c) 2H-Pyran, 2,2,3,3,4,4,6,6-nonafluorotetrahydro-5-(trifluoromethyl)- (CAS#61340-74-7);
d) 2H-Pyran, 2,2,6,6-tetrafluorotetrahydro-4-(trifluoromethyl)- (CAS#657-48-7);

e) 2H-Pyran, 2,2,3,3,4,4,5,5,6-nonafluorotetrahydro-6-methyl- (CAS#874634-55-6);
f) Perfluorotetrahydropyran (CAS#355-79-3);
g) 2H-Pyran, 2,2,3,3,4,5,5,6-octafluorotetrahydro-, (4R,6S)-rel- (CAS#362631-93-4); and
h) 2H-Pyran, 2,2,3,3,4,4,5,5,6-nonafluorotetrahydro- (CAS#65601-69-6).

In various embodiments, the compound has a molar water solubility of less than about 1.1 mM and greater than about 0.016 mM. In various embodiments, the compound potentiates $GABA_A$ receptors, but does not inhibit NMDA receptors.

In some embodiments, the subject is a mammal. In some embodiments, the subject is a human.

In a further aspect, the invention provides compositions comprising a compound or a mixture of compounds used in the above and herein described methods, wherein the composition is formulated for inhalational or pulmonary delivery of the compound or mixture of compounds.

In a further aspect, the invention provides methods of selecting an anesthetic that preferentially activates or potentiates $GABA_A$ receptors without inhibiting NMDA receptors. In some embodiments, the methods comprise:
  a) determining the molar water solubility of the anesthetic; and
  b) selecting an anesthetic with a molar water solubility below about 1.1 mM,
wherein the anesthetic selectively potentiates $GABA_A$ receptors and does not inhibit NMDA receptors, whereby an anesthetic that preferentially activates or potentiates $GABA_A$ receptors without inhibiting NMDA receptors is selected. In various embodiments, the anesthetic is an inhalational anesthetic. In some embodiments, the anesthetic is selected from the group consisting of halogenated alcohols, halogenated diethers, halogenated dioxanes, halogenated dioxolanes, halogenated cyclopentanes, halogenated cyclohexanes, halogenated tetrahydrofurans and halogenated tetrahydropyrans, wherein the anesthetic has a vapor pressure of at least 0.1 atmospheres (76 mmHg) at 25° C., and the number of hydrogen atoms do not exceed the number of carbon atoms. In some embodiments, the anesthetic is selected from the compounds administered in the methods described above and herein. In some embodiments, the anesthetic is selected from the group consisting of nonane, midazolam, diazepam, undecanol, etomidate, 1,2 dichlorohexafluorocyclobutane, and analogs thereof.

In a related aspect, the invention provides methods of selecting an anesthetic that both potentiates $GABA_A$ receptors and inhibits NMDA receptors. In some embodiments, the methods comprise:
  a) determining the molar water solubility of the anesthetic; and
  b) selecting an anesthetic with a molar water solubility above about 1.1 mM,
wherein the anesthetic both potentiates $GABA_A$ receptors and inhibits NMDA receptors, whereby an anesthetic that both potentiates $GABA_A$ receptors and inhibits NMDA receptors is selected. In various embodiments, the anesthetic is an inhalational anesthetic. In some embodiments, the anesthetic is selected from the group consisting of halogenated alcohols, halogenated diethers, halogenated dioxanes, halogenated dioxolanes, halogenated cyclopentanes, halogenated cyclohexanes, halogenated tetrahydrofurans and halogenated tetrahydropyrans, wherein the anesthetic has a vapor pressure of at least 0.1 atmospheres (76 mmHg) at 25° C., and the number of hydrogen atoms do not exceed the number of carbon atoms. In some embodiments, the anesthetic is selected from the compounds administered in the methods described above and herein. In some embodiments, the anesthetic is selected from the group consisting of sevoflurane, propofol, ketamine, isoflurane, enflurane, dizocilpine, desflurane, halothane, cyclopropane, chloroform, 2,6-dimethylphenol, methoxyflurane, diethyl ether, nitrous oxide, ethanol, and analogs thereof.

In another aspect, the invention of determining the specificity of an anesthetic for an anesthetic-sensitive receptor comprising determining whether the molar water solubility of the anesthetic is above or below a predetermined solubility threshold concentration for an anesthetic-sensitive receptor,
  wherein an anesthetic with a molar water solubility below about 1.2 mM does not inhibit $Na_v$ channels, but can inhibit NMDA receptors, potentiate two-pore domain potassium channels ($K_{2P}$), potentiate glycine receptors and potentiate $GABA_A$ receptors;
  wherein an anesthetic with a molar water solubility below about 1.1 mM does not inhibit $Na_v$ channels or inhibit NMDA receptors, but can potentiate two-pore domain potassium channels ($K_{2P}$), potentiate glycine receptors and potentiate $GABA_A$ receptors; wherein an anesthetic with a molar water solubility below about 0.26 mM does not inhibit $Na_v$ channels, inhibit NMDA receptors or potentiate two-pore domain potassium channel ($K_{2P}$) currents, but can potentiate glycine receptors and potentiate $GABA_A$ receptors; and
  wherein an anesthetic with a molar water solubility below about 68 µM does not inhibit $Na_v$ channels, inhibit NMDA receptors, potentiate two-pore domain potassium channel ($K_{2P}$) currents, or potentiate $GABA_A$ receptors but can potentiate glycine receptors; thereby determining the specificity of an anesthetic for an anesthetic-sensitive receptor. In various embodiments, the anesthetic is an inhalational anesthetic. In some embodiments, the anesthetic is selected from the group consisting of halogenated alcohols, halogenated diethers, halogenated dioxanes, halogenated dioxolanes, halogenated cyclopentanes, halogenated cyclohexanes, halogenated tetrahydrofurans and halogenated tetrahydropyrans, wherein the anesthetic has a vapor pressure of at least 0.1 atmospheres (76 mmHg) at 25° C., and the number of hydrogen atoms do not exceed the number of carbon atoms. In some embodiments, the anesthetic is selected from the compounds administered in the methods described above and herein.

In another aspect, the invention provides methods of modulating the specificity of an anesthetic for an anesthetic-sensitive receptor. In some embodiments, the methods comprise adjusting the molar water solubility of the anesthetic to be above a predetermined water solubility threshold concentration for an anesthetic-sensitive receptor that the anesthetic can modulate or adjusting the molar water solubility of the anesthetic to be below a predetermined molar water solubility threshold concentration for an anesthetic-sensitive receptor that the anesthetic cannot modulate;
  wherein an anesthetic with a molar water solubility below about 1.2 mM does not inhibit $Na_v$ channels, but can inhibit NMDA receptors, potentiate two-pore domain potassium channels ($K_{2P}$), potentiate glycine receptors and potentiate $GABA_A$ receptors;
  wherein an anesthetic with a molar water solubility below about 1.1 mM does not inhibit $Na_v$ channels or inhibit NMDA receptors, but can potentiate two-pore domain potassium channels ($K_{2P}$), potentiate glycine receptors and potentiate $GABA_A$ receptors;
  wherein an anesthetic with a molar water solubility below about 0.26 mM does not inhibit $Na_v$ channels, inhibit NMDA receptors or potentiate two-pore domain potassium channel ($K_{2P}$) currents, but can potentiate glycine receptors and potentiate $GABA_A$ receptors; and wherein an anesthetic with a molar water solubility below about 68 µM does not inhibit $Na_v$ channels, inhibit NMDA receptors, potentiate two-pore domain potassium channel ($K_{2P}$) currents, or potentiate $GABA_A$ receptors but can potentiate glycine receptors; thereby determining the specificity of an anesthetic for an anesthetic-sensitive receptor. In various embodiments, the anesthetic is an inhalational anesthetic or an analog thereof. In some embodiments, the anesthetic is selected from the group consisting of halogenated alcohols, halogenated diethers, halogenated dioxanes, halogenated dioxolanes, halogenated cyclopentanes, halogenated cyclohexanes, halogenated tetrahydrofurans and halogenated tetrahydropyrans, wherein the anesthetic has a vapor pressure of at least 0.1 atmospheres (76 mmHg) at 25° C., and the number of hydrogen atoms do not exceed the number of carbon atoms. In some embodiments, the anesthetic is selected from the compounds administered in the methods described above and herein. In some embodiments, the anesthetic is selected from the group consisting of nonane, midazolam, diazepam, undecanol, etomidate, 1,2-dichlorohexafluorocyclobutane, and analogs thereof. In some embodiments, the anesthetic is selected from the group consisting of sevoflurane, propofol, ketamine, isoflurane, enflurane, dizocilpine, desflurane, halothane, cyclopropane, chloroform, 2,6-dimethylphenol, methoxyflurane, diethyl ether, nitrous oxide, ethanol, and analogs thereof. In some embodiments, the anesthetic is adjusted to have a molar water solubility of less than about 1.1 mM and potentiates $GABA_A$ receptors but does not inhibit NMDA receptors. In some embodiments, the anesthetic is adjusted to have a molar water solubility of greater than about 1.1 mM and both potentiates $GABA_A$ receptors and inhibits NMDA receptors.

DEFINITIONS

The term "inhalational anesthetic" refers to gases or vapors that possess anesthetic qualities that are administered by breathing through an anesthesia mask or ET tube connected to an anesthetic machine. Exemplary inhalational anesthetics include without limitation volatile anesthetics (halothane, isoflurane, sevoflurane and desflurane) and the gases (ethylene, nitrous oxide and xenon).

The term "injectable anesthetic or sedative drug" refers to anesthetics or sedatives that can be injected under the skin via a hypodermic needle and syringe and that through actions on nerves in the brain or spinal cord can either render an individual insensible to painful stimuli, or decrease an individual's perceived sensation of painful stimuli, or induce within an individual an amnestic and/or calming effect.

The term "anesthetic-sensitive receptor" refers to a cell membrane protein that binds to an anesthetic agent and whose function is modulated by the binding of that anesthetic agent. Anesthetic-sensitive receptors are usually ion channels or cell membrane that are indirectly linked to ion channels via second messenger systems (such as G-proteins and tyrosine kinases) and can have 2, 3, 4, or 7 transmembrane regions. Such receptors can be comprised of 2 or more subunits and function as part of a protein complex. Activation or inhibition of these receptors results in either a direct change in ion permeability across the cell membrane that alters the cell resting membrane potential, or alters the response of the cell receptor to its endogenous ligand in such a way that the change in ion permeability and cell membrane potential normally elicited by the endogenous ligand is changed. Exemplary anesthetic-sensitive receptors include gamma-aminobutyric acid (GABA) receptors, N-methyl-D-aspartate (NMDA) receptors, voltage-gated sodium ion channels, voltage-gated potassium ion channels, two-pore domain potassium channels, adrenergic receptors, acetylcholine receptors, glycine and opioid receptors.

The term "effective amount" or "pharmaceutically effective amount" refer to the amount and/or dosage, and/or dosage regime of one or more compounds necessary to bring about the desired result e.g., an amount sufficient to effect anesthesia, render the subject unconscious and/or immobilize the subject.

As used herein, the term "pharmaceutically acceptable" refers to a material, such as a carrier or diluent, which does not abrogate the biological activity or properties of the compound useful within the invention, and is relatively non-toxic, i.e., the material may be administered to an individual without causing undesirable biological effects or interacting in a deleterious manner with any of the components of the composition in which it is contained.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof.

As used herein, the term "composition" or "pharmaceutical composition" refers to a mixture of at least one compound useful within the invention with a pharmaceutically acceptable carrier. The pharmaceutical composition facilitates administration of the compound to a subject.

The phrase "cause to be administered" refers to the actions taken by a medical professional (e.g., a physician), or a person controlling medical care of a subject, that control and/or permit the administration of the agent(s)/compound(s) at issue to the subject. Causing to be administered can involve diagnosis and/or determination of an appropriate therapeutic or prophylactic regimen, and/or prescribing particular agent(s)/compounds for a subject. Such prescribing can include, for example, drafting a prescription form, annotating a medical record, and the like.

The terms "patient," "individual," "subject" interchangeably refer to any mammal, e.g., a human or non-human mammal, e.g., a non-human primate, a domesticated mammal (e.g., canine, feline), an agricultural mammal (e.g., equine, bovine, ovine, porcine), or a laboratory mammal (e.g., rattus, murine, lagomorpha, hamster).

The term "molar water solubility" refers to the calculated or measured number of moles per liter of a compound present at a saturated concentration in pure water at 25° C. and at pH=7.0.

The term "solubility cut-off value" refers to the threshold water solubility concentration of an anesthetic compound that can activate a particular anesthetic-sensitive receptor. If the water solubility of the anesthetic agent is below the solubility cut-off value for a particular anesthetic-sensitive receptor, then the agent will not activate that receptor. If the water solubility of the anesthetic agent is above the solubility cut-off value for a particular anesthetic-sensitive receptor, then the agent can, but need not, activate that receptor.

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. For each of the definitions herein (e.g., alkyl, alkoxy, alkylamino, alkylthio, alkylene, haloalkyl), when a prefix is not included to indicate the number of main chain carbon atoms in an alkyl portion, the radical or portion thereof will have 24 or fewer, for example, 20, 18, 16, 14, 12, 10, 8, 6 or fewer, main chain carbon atoms.

The term "alkylene" by itself or as part of another substituent means an unsaturated hydrocarbon chain containing 1 or more carbon-carbon double bonds. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms.

The term "cycloalkyl" refers to hydrocarbon rings having the indicated number of ring atoms (e.g., $C_{3-6}$cycloalkyl) and being fully saturated or having no more than one double bond between ring vertices. One or two C atoms may optionally be replaced by a carbonyl. "Cycloalkyl" is also meant to refer to bicyclic and polycyclic hydrocarbon rings such as, for example, bicyclo[2.2.1]heptane, bicyclo[2.2.2] octane, etc. When a prefix is not included to indicate the number of ring carbon atoms in a cycloalkyl, the radical or portion thereof will have 8 or fewer ring carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3 to 8 membered ring with the nitrogen atom to which each is attached. Accordingly, a group represented as —NR$^{aRb}$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means a monovalent monocyclic, bicyclic or polycyclic aromatic hydrocarbon radical of 5 to 14 ring atoms which is unsubstituted or substituted independently with one to four substituents, preferably one, two, or three substituents selected from alkyl, cycloalkyl, cycloalkyl-alkyl, halo, cyano, hydroxy, alkoxy, amino, acylamino, mono-alkylamino, di-alkylamino, haloalkyl, haloalkoxy, heteroalkyl, COR (where R is hydrogen, alkyl, cycloalkyl, cycloalkyl-alkyl cut, phenyl or phenylalkyl, aryl or arylalkyl), —(CR'R")$_n$—COOR (where n is an integer from 0 to 5, R' and R" are independently hydrogen or alkyl, and R is hydrogen, alkyl, cycloalkyl, cycloalkylalkyl cut, phenyl or phenylalkyl aryl or arylalkyl) or —(CR'R")$_n$— CONR$^{aRb}$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl, aryl or arylalkyl). More specifically the term aryl includes, but is not limited to, phenyl, biphenyl, 1-naphthyl, and 2-naphthyl, and the substituted forms thereof. Similarly, the term "heteroaryl" refers to those aryl groups wherein one to five heteroatoms or heteroatom functional groups have replaced a ring carbon, while retaining aromatic properties, e.g., pyridyl, quinolinyl, quinazolinyl, thienyl, and the like. The heteroatoms are selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. For brevity, the term aryl, when used in combination with other radicals (e.g., aryloxy, arylalkyl) is meant to include both aryl groups and heteroaryl groups as described above.

Substituents for the aryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R''', —NH—C(NH$_2$) =NH, —NR'C(NH$_2$)=NH, —NH—C(NH$_2$)=NR', —S(O)R', —S(O)$_2$R', —S(O)$_2$NR'R", —NR'S(O)$_2$R", —N$_3$, perfluoro($C_{1-4}$)alkoxy, and perfluoro($C_{1-4}$)alkyl, in a number ranging from zero to the total number of open valences on the aromatic ring system; and where R', R" and R''' are independently selected from hydrogen, $C_{1-8}$ alkyl, $C_{3-6}$ cycloalkyl, $C_{2-8}$ alkenyl, $C_{2-8}$ alkynyl unsubstituted aryl and heteroaryl, (unsubstituted aryl)-$C_{1-4}$ alkyl, and unsubstituted aryloxy-$C_{1-4}$ alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X— (CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted $C_{1-6}$ alkyl.

As used herein, the term "heteroatom" is meant to include oxygen (O), nitrogen (N), sulfur (S) and silicon (Si).

DETAILED DESCRIPTION

I. Introduction

The present invention is based, in part, on the surprising discovery that the specificity of an anesthetic for an anesthetic-sensitive receptor can be modulated (e.g., increased or decreased) by altering the water solubility of the anesthetic. Based on the threshold solubility cut-off values for different families of anesthetic-sensitive receptors, anesthetics can be designed to activate subsets of receptors with a water solubility cut-off value that is less than the water solubility of the anesthetic, while not activating receptors with a water solubility cut-off value that is greater than the water solubility of the anesthetic. Generally, anesthetics with a relatively higher water solubility activate a larger number of anesthetic-sensitive receptors; anesthetics with a relatively lower water solubility activate fewer anesthetic-sensitive receptors. The present discovery finds use in determining the specificity of a particular anesthetic for different anesthetic-sensitive receptors, e.g., by comparing the water solubility of the anesthetic with the threshold solubility cut-off values of different anesthetic-sensitive receptors. The present discovery also finds use in guiding the rational chemical modification or derivitization of an anesthetic to adjust its water solubility and specificity for different anesthetic-sensitive receptors.

Figure 1:
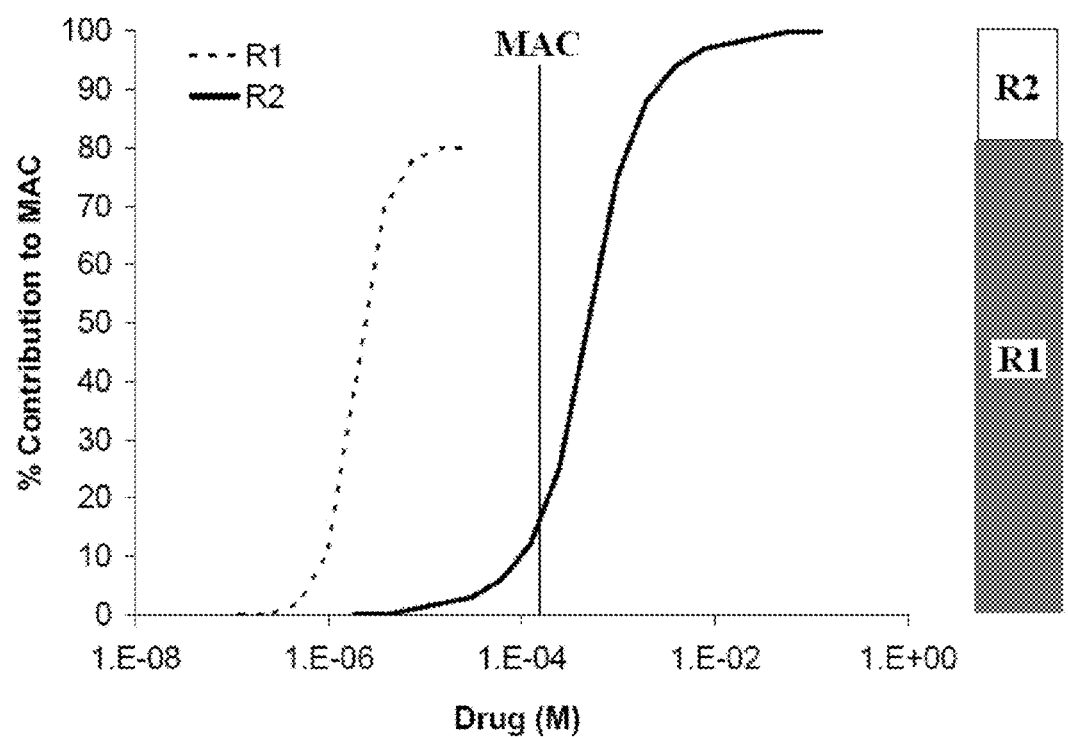
FIG. 1 illustrates a diagram showing the effect of drug dose on the percent contribution to MAC of 2 anesthetic-sensitive receptors (R1 and R2). The drug shows high-affinity for R1, but is unable to produce an anesthetic effect by itself. A small contribution from low-affinity interactions with R2 is necessary to produce a 100% anesthetic effect (MAC).
Figure 2:
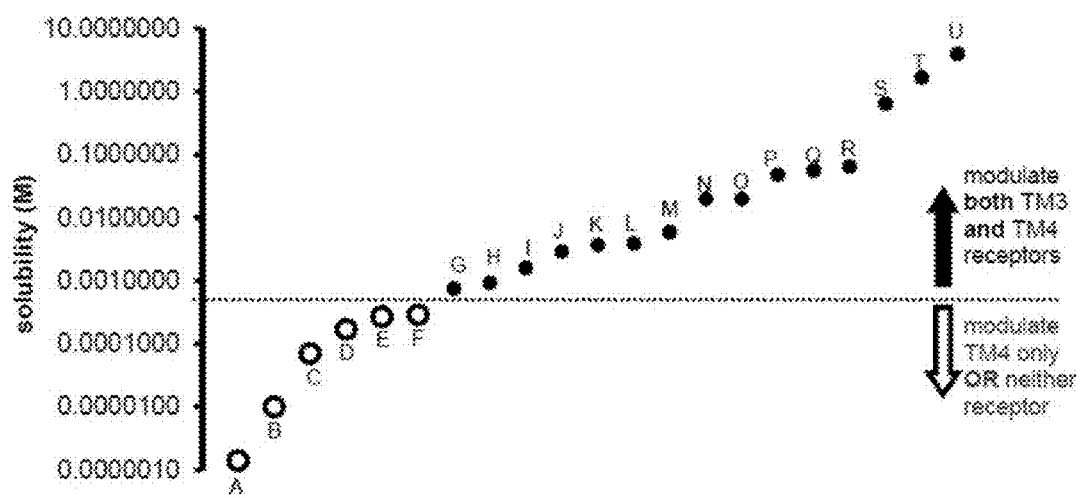
FIG. 2 illustrates a summary of ion channel modulation as a function of calculated anesthetic molar solubility in unbuffered water at 25° C. (values from SciFinder Scholar). Drugs that modulate 4-transmembrane receptors (TM4) or neither receptor type are shown as open circles (○, A-F) below the dotted horizontal solubility line. Drugs that modulate both 3-transmembrane (TM3) and TM4 receptors are shown as small black circles (●, G-U) above the dotted horizontal solubility line. A=nonane, B=midazolam (Nistri, et al., *Neurosci Lett* (1983) 39:199-204), C=diazepam (Macdonald, et al., *Nature* (1978) 271:563-564), D=undecanol (Dildy-Mayfield, et al., *Br J Pharmacol* (1996) 118:378-384), E=etomidate (Flood, et al., *Anesthesiology* (2000) 92:1418-1425), F=1,2-dichlorohexafluorocyclobutane (Kendig, et al., *Eur J Pharmacol* (1994) 264:427-436), G=sevoflurane (Jenkins, et al., *Anesthesiology* 1999; 90:484-491; Krasowski, *Br J Pharmacol* (2000) 129:731-743; Hollmann, *Anesth Analg* (2001) 92:1182-1191, Nishikawa, et al., *Anesthesiology* (2003) 99:678-684), H=propofol (Yamakura, et al., *Neurosci Lett* (1995) 188:187-190; Hales, et al., *Br J Pharmacol* (1991) 104:619-628), I=ketamine (Flood, et al., *Anesthesiology* (2000) 92:1418-1425; Hollmann, *Anesth Analg* (2001) 92:1182-1191; Yamakura, et al., *Anesthesiology* (2000) 92:1144-1153), J=isoflurane (Jenkins, et al., *Anesthesiology* (1999) 90:484-491; Krasowski, et al., *Br J Pharmacol* (2000) 129:731-743; Hollmann, et al., *Anesth Analg* (2001) 92:1182-1191; Yamakura, et al., *Anesthesiology* (2000) 93:1095-1101; Ogata, et al., *J Pharmacol Exp Ther* (2006) 318:434-443), K=enflurane (Krasowski, et al., *Br J Pharmacol* (2000) 129:731-743; Martin, et al. *Biochem Pharmacol* (1995) 49:809-817), L=dizocilpine (Yamakura, et al., *Anesthesiology* (2000) 92:1144-1153; Wong, et al., *Proc Natl Acad Sci USA* (1986) 83:7104-7108), M=desflurane (Hollmann, et al., *Anesth Analg* (2001) 92:1182-1191; Nishikawa, et al., *Anesthesiology* (2003) 99:678-684), N=halothane (Jenkins, et al., *Anesthesiology* (1999) 90:484-491; Ogata, et al., *J Pharmacol Exp Ther* (2006) 318:434-443; Martin, et al., *Biochem Pharmacol* (1995) 49:809-817), O=cyclopropane (Ogata, et al., *J Pharmacol Exp Ther* (2006) 318:434-443; Hara, et al., *Anesthesiology* (2002) 97:1512-1520.), P-chloroform, 61 Q=2,6-dimethylphenol, 65 R=methoxyflurane (Jenkins, et al., *Anesthesiology* (1999) 90:484-491; Krasowski, et al., *Br J Pharmacol* (2000) 129:731-743; Martin, et al. *Biochem Pharmacol* (1995) 49:809-817), S=diethyl ether (Krasowski, et al., *Br J Pharmacol* (2000) 129:731-743; Martin, et al. *Biochem Pharmacol* (1995) 49:809-817), T=nitrous oxide (Yamakura, et al., *Anesthesiology* (2000) 93:1095-1101; Ogata, et al., *J Pharmacol Exp Ther* (2006) 318:434-443), U=ethanol (Yamakura, et al., *Anesthesiology* (2000) 93:1095-1101). Most conventional and experimental agents modulate members of 4-transmembrane ion channels (e.g., γ-aminobutyric acid Type A or $GABA_A$ receptors, glycine receptors, and nicotinic acetylcholine receptors) and 3-transmembrane ion channels (e.g., N-methyl-d-aspartate or NMDA receptors). However, agents with low molar water solubility fail to modulate 3-transmembrane receptors.

Some anesthetics bind with high affinity (low EC50) to either 4-transmembrane receptors (i.e., $GABA_A$) or 3-transmembrane receptors (i.e., NMDA), but not to members of both receptor superfamilies. However, drugs with sufficient amphipathic properties can modulate members of both receptor superfamilies; this is true not only for ketamine and propofol, but for many conventional and experimental anesthetics (FIG. 2). Based the information in FIG. 2, sufficient water solubility appears sufficient to allow modulation of phylogenetically unrelated receptor superfamilies. Further, FIG. 2 would suggest that compounds with a molar solubility less than approximately 1 mM exhibit receptor superfamily specificity, but compounds with greater molar aqueous solubility can modulate 3- and 4-transmembrane receptors, if applied in sufficient concentrations. The importance of aqueous anesthetic concentration to mediate low-affinity ion channel effects explains why receptor point mutations near water cavities in proteins or near the plasma membrane-extracellular interface can dramatically affect sensitivity to volatile anesthetics (Lobo, et al., *Neuropharmacology* (2006) 50: 174-81). In addition, the anesthetic cut-off effect with increasing hydrocarbon chain length may be due to an insufficient molar water solubility of large hydrophobic molecules (Katz, et al., *J Theor Biol* (2003) 225: 341-9). In effect, this may not be a size cut-off, but a solubility cut-off.

Anesthetics do not distribute equally throughout the lipid bilayer. Halothane shows a preference for the phospholipid headgroup interface (Vemparala, et al., *Biophys J* (2006) 91: 2815-25). Xenon atoms prefer regions at the lipid-water interface and the central region of the bilayer (Stimson, et al., *Cell Mol Biol Lett* (2005) 10: 563-9). The anesthetics cyclopropane, nitrous oxide, desflurane, isoflurane, and 1,1, 2-trifluoroethane (TFE) all preferentially concentrate at the interface between water and hexane (Pohorille et al., *Toxicol Lett* (1998) 100-101: 421-30). However, perfluoroethane, a compound structurally similar to TFE, does not exhibit an hydrophilic-hydrophobic interfacial maxima, and it is both poorly soluble in water and a nonimmobilizer (Pohorille, supra). It has been hypothesized that accumulation of amphipathic anesthetics at the lipid-water interface may decrease surface tension (Wustneck, et al., *Langmuir* (2007) 23: 1815-23) and reduce the lateral pressure profile of the membrane phospholipids (Terama, et al., *J Phys Chem B* (2008) 112: 4131-9). This could alter the hydration status of membrane proteins (Ho, et al., *Biophys J* (1992) 63: 897-902), and thus alter conduction through ion channels. It is possible that the "anesthetic sensitivity" of certain channels may simply be a marker of receptors that are subject to modulation by interfacial hydrophilic interactions.

However, there is no reason to presume that the same number of hydrophilic or hydrophobic anesthetic interactions should be identical for dissimilar ion channels. The 2-transmembrane (e.g., P2X, P2Z receptors), 3-transmembrane (e.g., AMPA, kainite, and NMDA receptors), 4-transmembrane (nACh, 5-HT$_3$, GABA$_A$, GABA$_C$, and glycine receptors), and 7-transmembrane (G-protein coupled receptors) superfamilies are phylogenetically unrelated (Foreman J C, Johansen T: Textbook of Receptor Pharmacology, 2nd Edition. Boca Raton, CRC Press, 2003). Hence, it seems likely that the number of anesthetic molecules at the lipid water interface necessary to modulate a receptor should be different for members of different superfamilies, but more similar for channels within the same superfamily since these share greater sequence homology.

If non-specific interactions of anesthetics at the lipid-water interface are important for low-affinity and promiscuous ion channel modulations, then at least two predictions can be made.

First, sufficient water solubility should be important for interfacial interactions, and thus any amphipathic molecule with sufficient water solubility should be able to modulate anesthetic-sensitive channels. This statement is supported by numerous studies that show GABA$_A$, glycine, NMDA, two-pore domain potassium channels, and other anesthetic-sensitive channels can be modulated by conventional and nonconventional anesthetics, including carbon dioxide, ammonia, ketone bodies, and detergents (Yang, et al, *Anesth Analg* (2008) 107: 868-74; Yang, et al., *Anesth Analg* (2008) 106: 838-45; Eger, et al., *Anesth Analg* (2006) 102: 1397-406; Solt, et al., *Anesth Analg* (2006) 102: 1407-11; Krasowski, et al., *J Pharmacol Exp Ther* (2001) 297: 338-51; Brosnan, et al., *Anesth Analg* (2007) 104: 1430-3; Brosnan, et al., *Br J Anaesth* (2008) 101: 673-9; Mohammadi, et al., *Eur J Pharmacol* (2001) 421: 85-91; Anderson, et al., *J Med Chem* (1997) 40: 1668-81; Brosnan, et al., *Anesth Analg* (2006) 103: 86-91). 87-96). Moreover, receptor mutations that decrease ion channel sensitivity to conventional anesthetics can also decrease sensitivity to nonconventional ones as well (Yang, et al., *Anesth Analg* (2008) 106: 838-45), suggesting these disparate compounds all share a common nonspecific mechanism for interacting with unrelated ion channels.

Second, the number of non-specific interfacial interactions should be different between non-homologous channels. Hence, a prime determinant of the cut-off effect for ion channel modulation should be the water solubility of a drug, and this threshold solubility cut-off concentration should differ between ion channels from unrelated superfamilies (e.g., 3-vs. 4-transmembrane receptors). Preliminary data supports this contention (FIG. 9). In these studies, whole cell currents of oocytes expressing either GABA$_A$ (human $\alpha_1\beta_2\gamma_{2s}$) receptors or NMDA (human NR1/rat NR2A) receptors were measured in the presence and absence of saturated hydrocarbons with differing functional groups. For a given homologous hydrocarbon series (with an identical functional group), the agent solubility was varied by increasing the hydrocarbon chain length at the $\Omega$-position. For example, the alkane series consisted of n-butane, n-pentane, and n-hexane; the alcohol series consisted of 1-decanol and 1-dodecanol; the amines consisted of 1-octadecamine and 1-eicosanamine; the ethers consisted of dipentylether and dihexylether; etc. All compounds studied were positive modulators (>10% increase over baseline) of GABA$_A$ receptors, but only compounds with a molar water solubility greater than approximately 1 mM were also able to modulate NMDA receptors (>10% decrease from baseline), as shown in FIG. 9. Hence, water solubility correlated with specificity for GABA$_A$ versus NMDA receptors. This correlation is remarkably good since solubility values are calculated—not measured—for compounds in unbuffered pure water instead of the polyionic buffered solutions in which whole cell currents were actually measured. Although increasing chain length increases molecular volume, the specificity cut-off was not associated with any particular hydrocarbon chain length. In addition, increasing chain length also changes the activity of a hydrocarbon in solution; but there was no correlation between saturated vapor pressure and the receptor specificity cut-off.

Inhaled anesthetics enjoy widespread clinical use in general anesthesia in animals and humans, even though these drugs pose patient risks in terms of cardiovascular and respiratory depression. Continued drug development is important to improving anesthetic safety. However, all volatile anesthetics in clinical use were developed in the 1970s or before (Terrell, *Anesthesiology* (2008) 108: 531-3).

Creating newer and safer anesthetics requires knowledge of properties that predict which receptors or receptor superfamilies are likely to be modulated (Solt, et al., *Curr Opin Anaesthesiol* 2007; 20: 300-6). Data are provided herein that demonstrate a threshold solubility related to NMDA versus GABA$_A$ receptor specificity; analogous threshold solubility-specificity "cut-off" values exist for other receptors as well. This is important, because actions at various receptors and ion channels determine the pharmacologic profile of a drug. An inhaled agent that selectively acts on NMDA receptors can offer increased analgesia and autonomic quiescence, as do other injectable NMDA antagonists (Cahusac, et al.,

*Neuropharmacology* (1984) 23: 719-24; Bovill, et al., *Br J Anaesth* (1971) 43: 496-9; Sanders, *Br Med Bull* (2004) 71: 115-35; France, et al., *J Pharmacol Exp Ther* (1989) 250: 197-201; Janig, et al., *J Auton Nerv Syst* (1980) 2: 1-14; and Ness, et al., *Brain Res* 1988; 450: 153-69). Drugs that act predominantly through certain GABA receptors can offer excellent amnesia (Clark, et al., *Arch Neurol* (1979) 36: 296-300; Bonin, et al., *Pharmacol Biochem Behav* (2008) 90: 105-12; Cheng, et al., *J Neurosci* 2006; 26: 3713-20; Sonner, et al., *Mol Pharmacol* (2005) 68: 61-8; Vanini, et al., *Anesthesiology* (2008) 109: 978-88), but may also contribute to significant respiratory depression (Harrison, et al., *Br J Pharmacol* 1985; 84: 381-91; Hedner, et al., *J Neural Transm* (1980) 49: 179-86; Yamada, et al., *Brain Res* 1982; 248: 71-8; Taveira da Silva, et al., *J Appl Physiol* (1987) 62: 2264-72; Delpierre, et al., *Neurosci Lett* (1997) 226: 83-6; Li, et al., *J Physiol* (2006) 577: 307-18; Yang, *J Appl Physiol* (2007) 102: 350-7). Other cut-off values may exist for receptors that cause negative inotropy and vasodilation, leading to cardiovascular instability in anesthetized patients.

Knowledge of threshold cut-off values, and the means to easily predict them through calculated estimates of a physical property facilitates the rational design of new agents with an improved safety profile. For example, a good analgesic with poor immobilizing effects can be turned into a good general anesthetic by increasing the water solubility of the agent, such as by addition of an alcohol group or halogen, or by removal of long aliphatic chains that are not involved with high-affinity binding interactions. Conversely, a good immobilizer could be altered to reduce water solubility in order eliminate certain side effects caused by receptor modulation above that cut-off value. It is also possible to alter activity at high affinity sites to make drugs less potent, thereby increasing the drug ED50 and adding potentially desirable pharmacodynamic effects from low-affinity sites at these higher concentrations.

The discovery of threshold solubility-specificity cut-off values allows one to make predictions regarding anesthetic mechanisms. For example, since receptors with the same superfamily share sequence homology, their solubility cut-off values should be more similar to each other than receptors from different superfamilies.

II. Compounds for Effecting Anesthesia or Sedation a. Properties of the Present Inhalational Anesthetics and Sedatives Using the water solubility threshold values to predict the efficacy and pharmacological activity of candidate compounds on anesthetic-sensitive receptors, compounds for effecting anesthesia or sedation via delivery through the respiratory passages have been identified. Some of the compounds potentiate $GABA_A$ receptors without inhibiting NMDA receptors. Candidate compounds are selected based on their molar water solubility, vapor pressure, saline-gas partition coefficient, carbon-to-halogen ratio, odor (or lack thereof), stability, e.g., in formulations for inhalational or pulmonary delivery, pharmacological activity on different anesthetic-sensitive receptors, and toxicity.

i. Molar Water Solubility and Channel Cut-Off Values

Inhaled agents produce anesthesia via a summation of ion channel and cell membrane receptor effects that serve to decrease neuronal excitability within the central nervous system. Anesthetic efficacy at specific ion channels and cell membrane receptors is predicted by molar water solubility. Hydrocarbons that have a molar water solubility greater than approximately 1.1 mM will modulate NMDA receptors whereas less soluble anesthetics will generally not, although there is small variability about this cut-off number with alcohols continuing to modulate NMDA receptors at slightly lower solubility values and ethers exhibiting a cut-off effect at slightly higher solubility values. Conversely, inhaled hydrocarbons that cannot potentiate $GABA_A$ receptors are not anesthetics. The water solubility cut-off for $GABA_A$ receptor modulation is around 0.068 mM, but current data from our laboratory shows a 95% confidence interval that extends from 0.3 mM to 0.016. These $GABA_A$ solubility cut-off values provide an absolute molar water solubility lower-limit for rapid database screening of potential anesthetic candidates. Inhaled agents less soluble than 0.068 mM are unlikely to exhibit an anesthetic effect. Non-gaseous volatile compounds more soluble than 100 mM are unlikely to have desirable pharmacokinetic properties, and this value serves as an upper solubility limit for database screening.

ii. Vapor Pressure

Inhaled anesthetics are administered via the respiratory system and thus need a sufficiently high vapor pressure to facilitate rapid agent delivery to a patient. The vapor pressure also must exceed anesthetic potency (a function of water and lipid solubility) for the agent to be delivered via inhalation at 1 atmosphere pressure. For database screening, we selected a minimum vapor pressure of 0.1 atmospheres (76 mmHg) at 25° C.

Inhaled sedatives are administered via the respiratory system and thus need a vapor pressure to facilitate rapid agent delivery to a patient. For database screening for sedatives, we selected a minimum vapor pressure of 0.005 atmospheres (4 mmHg) at 25° C.

iii. Saline-gas Partition Coefficient

Inhaled anesthetics with low Ostwald saline-gas partition coefficients exhibit desirable and rapid washin and washout kinetics. These values can be estimated using previously published QSPR correlations, or by identifying within a chemical family those compounds that exhibit high vapor pressure and low aqueous solubility which together suggest a low Ostwald saline-gas partition coefficient. Compounds should have a saline-gas partition coefficient ≤0.8 at 37° C.

iv. Carbon-to-Halogen Ratio

Modern anesthetics must be non-flammable in order to be clinically useful. Halogenation reduces flammability. Compounds for which the number of hydrogen atoms did not exceed the number of carbon atoms are preferred.

v. Parent Compound Properties

1. Odor

Malodorous compounds will not be tolerated by patients or perioperative personnel. Compounds containing thiols or sulfide linkages and primary and secondary amine compounds have unpleasant odors, and so volatile compounds containing these groups were excluded from screening.

2. Stability

Divalent bases (and sometimes monovalent bases) are used for $CO_2$ absorption in anesthetic circuits; clinically-useful agents must therefore be stable in the presence of strong bases. Compounds containing aldehyde, ketone, or carboxillic acid groups were unstable in soda lime are not preferred. Anesthetics should also be resistant to hydrolysis and redox reactions in vivo. Compounds with ester linkages can be thermally unstable or hydrolysed by plasma and tissue cholinesterases; and those compounds resistant to hydrolysis may likely cause undesirable inhibition of these enzymes (which are essential for metabolism of other drugs). Therefore, compounds with ester linkages are not preferred. Anesthetics with non-aromatic unsaturated carbon linkages have been used historically (fluroxene, isopropenyl vinyl ether, trichloroethylene, vinethylene, ethylene) and shown to undergo extensive metabolism that for some agents was associated with toxicity. Agents containing double or triple carbon bonds are not preferred.

3. Anesthetic-sensitive Channel and Receptor Effects

Clinically-relevant anesthetics should inhibit excitatory ion channels and cell receptors and potentiate inhibitory ion channels and cell receptors. However, tests with unhalogenated compounds containing tertiary amines (4-methylmorpholine, N-methylpiperadine) caused direct activation of NMDA receptors which would be expected to antagonize anesthetic effects and potentially cause neuronal injury at high concentrations. Accordingly, compounds containing tertiary amines are not preferred.

4. In Vitro and In Vivo Toxicity

Some parent structures (such as pyrrolidine) caused cytotoxicity during oocyte electrophysiology studies. These compounds are not preferred. Other structures previously known to be highly toxic to animals or humans (such as silanes and boranes) are not preferred.

b. Illustrative Anesthetics

Illustrative anesthetic compounds having the foregoing criteria include without limitation halogenated alcohol derivatives, halogenated diether (polyether) derivatives, halogenated dioxane derivatives, halogenated dioxolane derivatives, halogenated cyclopentane derivatives, halogenated cyclohexane derivatives, halogenated tetrahydrofuran derivatives, and halogenated tetrahydropyran derivatives. The compounds can be formulated for delivery to a subject via the respiratory pathways, e.g., for inhalational or pulmonary delivery.

The compounds described herein may form salts with acids, and such salts are included in the present invention. In one embodiment, the salts are pharmaceutically acceptable salts. The term "salts" embraces addition salts of free acids that are useful within the methods of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate), Appropriate organic acids may be selected from aliphatic, cycloaliphatic, aromatic, aralphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts, pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

Some of the compounds set forth herein include chiral centers. Chiral centers generally refer to a carbon atom that is attached to four unique substituents. With respect to these chiral-center containing compounds, the present invention provides for methods that include the use of, and administration of, these chiral-center containing compounds as either pure enantiomers, as mixtures of enantiomers, as well as mixtures of diastereoisomers or as a purified diastereomer. In some embodiments, the R configuration of a particular enantiomer is preferred for a particular method. In yet other embodiments, the S configuration of a particular enantiomer is preferred for a particular method. The present invention includes methods of administering racemic mixtures of compounds having chiral centers. The present invention includes methods of administering one particular stereoisomer of a compound. In certain embodiments, a particular ratio of one enantiomer to another enantiomer is preferred for use with a method described herein. In other embodiments, a particular ratio of one diastereomer to other diastereomers is preferred for use with a method described herein.

i. Halogenated Alcohol Derivatives

Illustrative halogenated alcohol derivatives include without limitation a compound or a mixture of compounds of Formula I:

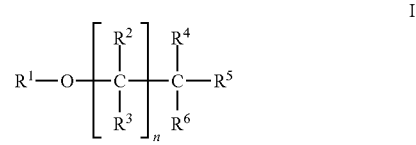

I wherein:
n is 0-4,
R$^1$ is H;
R$^2$, R$^3$, R$^4$, R$^5$ and R$^6$ independently are selected from H, X, CX$_3$, CHX$_2$, CH$_2$X and C$_2$X$_5$; and
wherein X is a halogen, the compound having vapor pressure of less than 0.1 atmospheres (76 mmHg) at 25° C., and the number of hydrogen atoms in Formula I do not exceed the number of carbon atoms, thereby inducing anesthesia in the subject. In various embodiments, X is a halogen selected from the group consisting of F, Cl, Br and I. In some embodiments, X is F. In some embodiments, R$^1$ is selected from H, CH$_2$OH, CHFOH and CF$_2$OH, CHClOH, CCl$_2$OH and CFClOH. In some embodiments, R$^2$, R$^3$, R$^4$, R$^5$ and R$^6$ independently are selected from H, F, Cl, Br, I, CF$_3$, CHF$_2$, CH$_2$F, C$_2$F$_5$, CCl$_3$, CHCl$_2$, CH$_2$Cl, C$_2$Cl$_5$, CCl$_2$F, CClF$_2$, CHClF, C$_2$ClF$_4$, C$_2$Cl$_2$F$_3$, C$_2$Cl$_3$F$_2$, and C$_2$Cl$_4$F.

In some embodiments, the halogenated alcohol derivatives are selected from the group consisting of:

a) Methanol, 1-fluoro-1-[2,2,2-trifluoro-1-(trifluoromethyl)ethyl)ethoxy]- (CAS #1351959-82-4);

b) 1-Butanol, 4,4,4-trifluoro-3,3-bis(trifluoromethyl)- (CAS#14115-49-2);

c) 1-Butanol, 1,1,2,2,3,3,4,4,4-nonafluoro- (CAS#3056-01-7);

d) 1-Butanol, 2,2,3,4,4,4-hexafluoro-3-(trifluoromethyl)- (CAS#782390-93-6);

e) 1-Butanol, 3,4,4,4-tetrafluoro-3-(trifluoromethyl)- (CAS#90999-87-4);

f) 1-Pentanol, 1,1,4,4,5,5,5-heptafluoro- (CAS#313503-66-1); and g) 1-Pentanol, 1,1,2,2,3,3,4,4,5,5,5-undecafluoro- (CAS#57911-98-5).

In some other embodiments, the halogenated alcohol derivatives are selected from the group consisting of:

a) 2-Pentanol, 1,1,1,3,3,5,5,5-octafluoro-2-(trifluoromethyl)- (CAS#144475-50-3);

b) 2-Pentanol, 1,1,1,3,4,5,5,5-octafluoro-4-(trifluoromethyl)-(2R,3S)- (CAS#126529-27-9);

c) 2-Pentanol, 1,1,1,3,4,4,5,5,5-nonafluoro-, (2R,3S)-rel- (CAS#126529-24-6);

d) 2-Pentanol, 1,1,1,3,4,5,5,5-octafluoro-4-(trifluoromethyl)-(2R,3R)- (CAS#126529-17-7);

e) 2-Pentanol, 1,1,1,3,4,4,5,5,5-nonafluoro-, (2R,3R)-rel- (CAS#126529-14-4);

f) 1-Butanol, 1,1,2,2,3,3,4,4-octafluoro- (CAS#119420-27-8);

g) 1-Butanol, 2,3,3,4,4,4-hexafluoro-2-(trifluoromethyl)- (CAS#111736-92-6);

h) 2-Pentanol, 1,1,1,3,3,4,5,5,5-nonafluoro-, (R*,S*)-(9CI) (CAS#99390-96-2);

i) 2-Pentanol, 1,1,1,3,3,4,5,5,5-nonafluoro-, (R*,R*)-(9CI) (CAS#99390-90-6);

j) 2-Pentanol, 1,1,1,3,3,4,4,5,5,5-decafluoro-2-(trifluoromethyl)- (CAS#67728-22-7);

k) 1-Pentanol, 1,1,2,2,3,3,4,4,5,5,5-undecafluoro- (CAS#57911-98-5);

l) 2-Pentanol, 1,1,1,3,3,4,4,5,5,5-decafluoro- (CAS#377-53-7);

m) 1-Pentanol, 2,2,3,4,4,5,5,5-octafluoro- (CAS#357-35-7);

n) 1-Butanol, 2,3,4,4,4-pentafluoro-2-(trifluoromethyl)- (CAS#357-14-2);

o) 1-Pentanol, 2,2,3,3,4,4,5,5,5-nonafluoro (CAS#355-28-2);

p) 1-Butanol, 2,3,4,4,4-pentafluoro-2-(trifluoromethyl)-(R*,S*)- (9CI) (CAS#180068-23-9);

q) 1-Butanol, 2,3,4,4,4-pentafluoro-2-(trifluoromethyl)-(R*,R*)- (9CI) (CAS#180068-22-8);

r) 2-Butanol, 1,1,1,3,3-pentafluoro-2-(trifluoromethyl)- (CAS#144444-16-6);

s) 2-Butanol, 1,1,1,3,3,4,4,4-octafluoro (CAS#127256-73-9);

t) 1-Butanol, 2,2,3,4,4,4-hexafluoro-3-(trifluoromethyl)- (CAS#782390-93-6);

u) 2-Propanol, 1,1,1,3,3,3-hexafluoro-2-(trifluoromethyl)- (CAS#2378-02-01);

v) 1-Hexanol, 1,1,2,2,3,3,4,4,5,5-decafluoro (CAS#1118030-44-6);

w) 1-Hexanol, 1,1,2,2,3,3,4,4,5,5,6,6-dodecafluoro- (CAS#119420-28-9);

x) 1-Hexanol, 1,1,2,2,3,3,4,4,5,5,6,6,6-tridecafluoro- (CAS#7057-81-0);

y) 1-Hexanol, 3,3,4,4,5,5,6,6,6-nonafluoro- (CAS#2043-47-2);

z) 1-Hexanol, 2,2,3,3,4,4,5,5,6,6,6-undecafluoro- (CAS#423-46-1);

aa) 1-Hexanol, 2,2,3,4,4,5,5,6,6,6-decafluoro- (CAS#356-25-2);

ab) 1-Heptanol, 3,3,4,4,5,5,6,6,7,7,7-undecafluoro- (CAS#185689-57-0);

ac) 1-Hexanol, 2,2,3,3,4,4,5,6,6,6-decafluoro-5-(trifluoromethyl)- (CAS#849819-50-7);

ad) 1-Hexanol, 2,2,3,3,4,4,5,6,6,6-decafluoro-5-(trifluoromethyl)- (CAS#89076-11-9);

ae) 1-Hexanol, 2,2,3,4,4,6,6,6-octafluoro-3,5,5-tris(trifluoromethyl)- (CAS#232267-34-4);

af) 1-Hexanol, 2,2,3,4,4,5,6,6,6-nonafluoro-3-(trifluoromethyl)- (CAS#402592-21-6);

ag) 1-Hexanol, 4,5,5,6,6,6-hexafluoro-4-(trifluoromethyl)- (CAS#239463-96-8); and ah) 1-Hexanol, 4,4,5,5,6,6,6-heptafluoro-3,3-bis(trifluoromethyl)- (CAS#161261-12-7).

In some embodiments, the above-described halogenated alcohol derivatives are useful as inhaled sedatives, also as inhaled tranquilizers, also as inhaled analgesics, and also as inhaled hypnotics. In some embodiments, the halogenated alcohol derivatives set forth herein are useful as inhaled sedatives. In some embodiments, the halogenated alcohol derivatives set forth herein are useful as inhaled tranquiliers. In some embodiments, the halogenated alcohol derivatives set forth herein are useful as inhaled analgesics. In some embodiments, the halogenated alcohol derivatives set forth herein are useful as inhaled hypnotics. In some embodiments, the halogenated alcohol derivatives set forth herein are useful as tranquiliers. In some embodiments, the halogenated alcohol derivatives set forth herein are useful as analgesics. In some embodiments, the halogenated alcohol derivatives set forth herein are useful as hypnotics.

Some of the above-described anesthetics, when administered at a vapor pressure of less than 0.1 atm (76 mm Hg), also induce sedation. The present invention provides methods, as described herein for inducing anesthesia, for inducing sedation wherein the methods include administering an anesthetic, as described herein and above, at a vapor pressure less than 0.1 atm (76 mm Hg).

In some specific embodiments, the halogenated alcohol derivative is selected from 1-Hexanol, 2,2,3,3,4,4,5,6,6,6-decafluoro-5-(trifluoromethyl)- (CAS#89076-11-9). 1-Hexanol, 2,2,3,3,4,4,5,6,6,6-decafluoro-5-(trifluoromethyl)- was observed to be useful as a GABA-A receptor agonist and a weak NMDA receptor antagonist at saturating aqueous phase concentrations. The present invention includes methods of administering 1-Hexanol, 2,2,3,3,4,4,5,6,6,6-decafluoro-5-(trifluoromethyl)- in order to induce sedative or hypnotic states in a subject or patient. In some instances, the method of administering 1-Hexanol, 2,2,3,3,4,4,5,6,6,6-decafluoro-5-(trifluoromethyl)- in order to induce sedation includes administering 1-Hexanol, 2,2,3,3,4,4,5,6,6,6-decafluoro-5-(trifluoromethyl)- at a vapor pressure of less than 0.1 atm.

ii. Halogenated Diether (Polyether) Derivatives

Illustrative halogenated diether (polyether derivatives) include without limitation a compound or a mixture of compounds of Formula II:

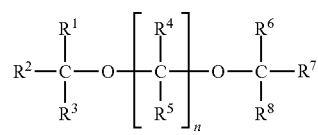

wherein:

n is 1-3, $R^1$, $R^2$, $R^3$, $R^4$, $R^5$, $R^6$, $R^7$ and $R^8$ independently are selected from H, X, $CX_3$, $CHX_2$, $CH_2X$ and $C_2X_5$; and wherein X is a halogen, the compound having vapor pressure of less than 0.1 atmospheres (76 mmHg) at 25°

C., and the number of hydrogen atoms in Formula II do not exceed the number of carbon atoms. In various embodiments, X is a halogen selected from the group consisting of F, Cl, Br and I. In some embodiments, X is F. In some embodiments, $R^1$, $R^2$, $R^3$, $R^4$, $R^5$, $R^6$, $R^7$ and $R^8$ independently are selected from H, F, Cl, Br, I, $CF_3$, $CHF_2$, $CH_2F$, $C_2F_5$, $CCl_3$, $CHCl_2$, $CH_2Cl$, $C_2Cl_5$, $CCl_2F$, $CClF_2$, $CHClF$, $C_2ClF_4$, $C_2Cl_2F_3$, $C_2Cl_3F_2$, and $C_2Cl_4F$.

In some embodiments, the halogenated diether (polyether derivatives) are selected from the group consisting of:
a) Ethane, 1,1,2-trifluoro-1,2-bis(trifluoromethoxy)- (CAS#362631-92-3);
b) Ethane, 1,1,1,2-tetrafluoro-2,2-bis(trifluoromethoxy)- (CAS#115395-39-6);
c) Ethane, 1-(difluoromethoxy)-1,1,2,2-tetrafluoro-2-(trifluoromethoxy)- (CAS#40891-98-3);
d) Ethane, 1,1,2,2-tetrafluoro-1,2-bis(trifluoromethoxy)- (CAS#378-11-0);
e) Ethane, 1,2-difluoro-1,2-bis(trifluoromethoxy)- (CAS#362631-95-6);
f) Ethane, 1,2-bis(trifluoromethoxy)- (CAS#1683-90-5);
g) Propane, 1,1,3,3-tetrafluoro-1,3-bis(trifluoromethoxy)- (CAS#870715-97-2);
h) Propane, 2,2-difluoro-1,3-bis(trifluoromethoxy)- (CAS#156833-18-0);
i) Propane, 1,1,1,3,3-pentafluoro-3-methoxy-2-(trifluoromethoxy)- (CAS#133640-19-4;
j) Propane, 1,1,1,3,3,3-hexafluoro-2-(fluoromethoxymethoxy)- (CAS#124992-92-3); and
k) Propane, 1,1,1,2,3,3-hexafluoro-3-methoxy-2-(trifluoromethoxy)- (CAS#104159-55-9).

iii. Halogenated Dioxane Derivatives

Illustrative halogenated dioxane derivatives include without limitation a compound or a mixture of compounds of Formula III:

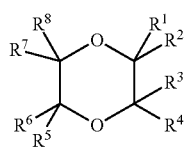

wherein:
$R^1$, $R^2$, $R^3$, $R^4$, $R^5$, $R^6$, $R^7$ and $R^8$ independently are selected from H, X, $CX_3$, $CHX_2$, $CH_2X$ and $C_2X_5$; and
wherein X is a halogen, the compound has a vapor pressure of less than 0.1 atmospheres (76 mmHg) at 25° C., and the number of hydrogen atoms of Formula III do not exceed the number of carbon atoms. In various embodiments, X is a halogen selected from the group consisting of F, Cl, Br and I. In some embodiments, X is F. In some embodiments, $R^1$, $R^2$, $R^3$, $R^4$, $R^5$, $R^6$, $R^7$ and $R^8$ independently are selected from H, F, Cl, Br, I, $CF_3$, $CHF_2$, $CH_2F$, $C_2F_5$, $CCl_3$, $CHCl_2$, $CH_2Cl$, $C_2Cl_5$, $CCl_2F$, $CClF_2$, $CHClF$, $C_2ClF_4$, $C_2Cl_2F_3$, $C_2Cl_3F_2$, and $C_2Cl_4F$.

In some embodiments, the halogenated dioxane derivatives are selected from the group consisting of:
a) 1,4-Dioxane, 2,2,3,3,5,6-hexafluoro- (CAS#362631-99-0);
b) 1,4-Dioxane, 2,3-dichloro-2,3,5,5,6,6-hexafluoro- (CAS#135871-00-0);
c) 1,4-Dioxane, 2,3-dichloro-2,3,5,5,6,6-hexafluoro-, trans- (9CI) (CAS#56625-45-7);
d) 1,4-Dioxane, 2,3-dichloro-2,3,5,5,6,6-hexafluoro-, cis- (9CI) (CAS#56625-44-6);
e) 1,4-Dioxane, 2,2,3,5,6,6-hexafluoro- (CAS#56269-26-2);
f) 1,4-Dioxane, 2,2,3,5,5,6-hexafluoro- (CAS#56269-25-1);
g) 1,4-Dioxane, 2,2,3,3,5,6-hexafluoro-, trans- (9CI) (CAS#34206-83-2);
h) 1,4-Dioxane, 2,2,3,5,5,6-hexafluoro-, cis- (9CI) (CAS#34181-52-7);
i) p-Dioxane, 2,2,3,5,5,6-hexafluoro-, trans- (8CI) (CAS#34181-51-6);
j) 1,4-Dioxane, 2,2,3,5,6,6-hexafluoro-, cis- (9CI) (CAS#34181-50-5);
k) p-Dioxane, 2,2,3,5,6,6-hexafluoro-, trans- (8CI) (CAS#34181-49-2);
l) 1,4-Dioxane, 2,2,3,3,5,6-hexafluoro-, (5R,6S)-rel- (CAS#34181-48-1);
m) 1,4-Dioxane, 2,2,3,3,5,5,6-heptafluoro- (CAS#34118-18-8); and
n) 1,4-Dioxane, 2,2,3,3,5,5,6,6-octafluoro- (CAS#32981-22-9).

iv. Halogenated Dioxolane Derivatives

Illustrative halogenated dioxolane derivatives include without limitation a compound or a mixture of compounds of Formula IV:

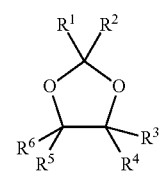

wherein:
$R^1$, $R^2$, $R^3$, $R^4$, $R^5$ and $R^6$ independently are selected from H, X, $CX_3$, $CHX_2$, $CH_2X$ and $C_2X_5$; and
wherein X is a halogen, the compound has a vapor pressure of less than 0.1 atmospheres (76 mmHg) at 25° C., and the number of hydrogen atoms of Formula IV do not exceed the number of carbon atoms. In various embodiments, X is a halogen selected from the group consisting of F, Cl, Br and I. In some embodiments, X is F. In some embodiments, $R^1$, $R^2$, $R^3$, $R^4$, $R^5$ and $R^6$ independently are selected from H, F, Cl, Br, I, $CF_3$, $CHF_2$, $CH_2F$, $C_2F_5$, $CCl_3$, $CHCl_2$, $CH_2Cl$, $C_2Cl_5$, $CCl_2F$, $CClF_2$, $CHClF$, $C_2ClF_4$, $C_2Cl_2F_3$, $C_2Cl_3F_2$, and $C_2Cl_4F$.

In some embodiments, the halogenated dioxolane derivatives are selected from the group consisting of:
a) 1,3-Dioxolane, 2,4,4,5-tetrafluoro-5-(trifluoromethyl)- (CAS#344303-08-8);
b) 1,3-Dioxolane, 2-chloro-4,4,5-trifluoro-5-(trifluoromethyl)- (CAS#344303-05-5);
c) 1,3-Dioxolane, 4,4,5,5-tetrafluoro-2-(trifluoromethyl)- (CAS#269716-57-6);
d) 1,3-Dioxolane, 4-chloro-2,2,4-trifluoro-5-(trifluoromethyl)- (CAS#238754-29-5);
e) 1,3-Dioxolane, 4,5-dichloro-2,2,4,5-tetrafluoro-, trans- (9CI) (CAS#162970-78-7);
f) 1,3-Dioxolane, 4,5-dichloro-2,2,4,5-tetrafluoro-, cis- (9CI) (CAS#162970-76-5);

g) 1,3-Dioxolane, 4-chloro-2,2,4,5,5-pentafluoro- (CAS#139139-68-7);

h) 1,3-Dioxolane, 4,5-dichloro-2,2,4,5-tetrafluoro- (CAS#87075-00-1);

i) 1,3-Dioxolane, 2,4,4,5-tetrafluoro-5-(trifluoromethyl)-, trans- (9CI) (CAS#85036-66-4);

j) 1,3-Dioxolane, 2,4,4,5-tetrafluoro-5-(trifluoromethyl)-, cis- (9CI) (CAS#85036-65-3);

k) 1,3-Dioxolane, 2-chloro-4,4,5-trifluoro-5-(trifluoromethyl)-, trans- (9CI) (CAS#85036-60-8);

l) 1,3-Dioxolane, 2-chloro-4,4,5-trifluoro-5-(trifluoromethyl)-, cis- (9CI) (CAS#85036-57-3);

m) 1,3-Dioxolane, 2,2-dichloro-4,4,5,5-tetrafluoro- (CAS#85036-55-1);

n) 1,3-Dioxolane, 4,4,5-trifluoro-5-(trifluoromethyl)- (CAS#76492-99-4);

o) 1,3-Dioxolane, 4,4-difluoro-2,2-bis(trifluoromethyl)- (CAS#64499-86-1);

p) 1,3-Dioxolane, 4,5-difluoro-2,2-bis(trifluoromethyl)-, cis- (9CI) (CAS#64499-85-0);

q) 1,3-Dioxolane, 4,5-difluoro-2,2-bis(trifluoromethyl)-, trans- (9CI) (CAS#64499-66-7);

r) 1,3-Dioxolane, 4,4,5-trifluoro-2,2-bis(trifluoromethyl)- (CAS#64499-65-6);

s) 1,3-Dioxolane, 2,4,4,5,5-pentafluoro-2-(trifluoromethyl)- (CAS#55135-01-8);

t) 1,3-Dioxolane, 2,2,4,4,5,5-hexafluoro- (CAS#21297-65-4); and u) 1,3-Dioxolane, 2,2,4,4,5-pentafluoro-5-(trifluoromethyl)- (CAS#19701-22-5).

v. Halogenated Cyclopentane Derivatives

Illustrative halogenated cyclopentane derivatives include without limitation a compound or a mixture of compounds of Formula V:

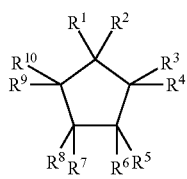

V wherein:

$R^1$, $R^2$, $R^3$, $R^4$, $R^5$, $R^6$, $R^7$, $R^8$, $R^9$ and $R^{10}$ independently are selected from H, X, $CX_3$, $CHX_2$, $CH_2X$ and $C_2X_5$; and wherein X is a halogen, the compound has a vapor pressure of less than 0.1 atmospheres (76 mmHg) at 25° C., and the number of hydrogen atoms of Formula V do not exceed the number of carbon atoms. In various embodiments, X is a halogen selected from the group consisting of F, Cl, Br and I. In some embodiments, X is F. In some embodiments, $R^1$, $R^2$, $R^3$, $R^4$, $R^5$, $R^6$, $R^7$, $R^8$, $R^9$ and $R^{10}$ independently are selected from H, F, Cl, Br, I, $CF_3$, $CHF_2$, $CH_2F$, $C_2F_5$, $CCl_3$, $CHCl_2$, $CH_2Cl$, $C_2Cl_5$, $CCl_2F$, $CClF_2$, $CHClF$, $C_2ClF_4$, $C_2Cl_2F_3$, $C_2Cl_3F_2$, and $C_2Cl_4F$.

In some embodiments, the halogenated cyclopentane derivatives are selected from the group consisting of:

a) Cyclopentane, 5-chloro-1,1,2,2,3,3,4,4-octafluoro- (CAS#362014-70-8); b) Cyclopentane, 1,1,2,2,3,4,4,5-octafluoro- (CAS#773-17-1);

c) Cyclopentane, 1,1,2,2,3,3,4,5-octafluoro- (CAS#828-35-3);

d) Cyclopentane, 1,1,2,3,3,4,5-heptafluoro- (CAS#3002-03-7);

e) Cyclopentane, 1,1,2,2,3,3,4,4-octafluoro- (CAS#149600-73-7);

f) Cyclopentane, 1,1,2,2,3,4,5-heptafluoro- (CAS#1765-23-7);

g) Cyclopentane, 1,1,2,3,4,5-hexafluoro- (CAS#699-38-7);

h) Cyclopentane, 1,1,2,2,3,3,4-heptafluoro- (CAS#15290-77-4);

i) Cyclopentane, 1,1,2,2,3,4-hexafluoro- (CAS#199989-36-1);

j) Cyclopentane, 1,1,2,2,3,3-hexafluoro- (CAS#123768-18-3); and k) Cyclopentane, 1,1,2,2,3-pentafluoro- (CAS#1259529-57-1).

In some embodiments, the halogenated cyclopentane derivatives are selected from the group consisting of:

c) Cyclopentane, 1,1,2,2,3,3,4,5-octafluoro- (CAS#828-35-3);

e) Cyclopentane, 1,1,2,2,3,3,4,4-octafluoro- (CAS#149600-73-7); and h) Cyclopentane, 1,1,2,2,3,3,4-heptafluoro- (CAS#15290-77-4).

In some embodiments, the compound administered, or used with any of the methods set forth herein, is 1,1,2,2,3,3,4,5-octafluorocyclopentane. In certain embodiments, the compound has the structure selected from the group consisting of

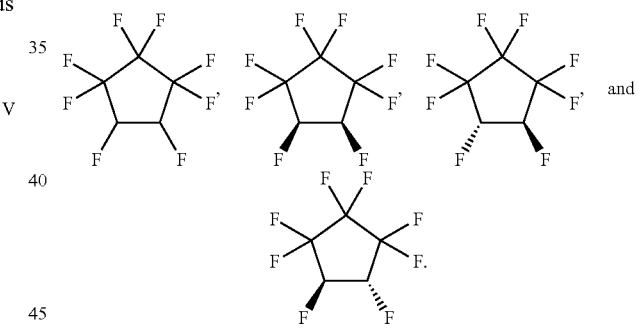

In certain embodiments, the compound administered, or used with any of the methods set forth herein, is selected from the group consisting of (4R,5S)-1,1,2,2,3,3,4,5-octafluorocyclopentane, (4S,5S)-1,1,2,2,3,3,4,5-octafluorocyclopentane, and (4R,5R)-1,1,2,2,3,3,4,5-octafluorocyclopentane. Mixtures of (4R,5S)-1,1,2,2,3,3,4,5-octafluorocyclopentane, (4S,5S)-1,1,2,2,3,3,4,5-octafluorocyclopentane, and (4R,5R)-1,1,2,2,3,3,4,5-octafluorocyclopentane may be used with the methods set forth herein. The present invention also includes administering, or using with any of the methods set forth herein, a particular stereoisomer of 1,1,2,2,3,3,4,5-octafluorocyclopentane, e.g., (4R,5S)-1,1,2,2,3,3,4,5-octafluorocyclopentane, or (4S,5S)-1,1,2,2,3,3,4,5-octafluorocyclopentane, or (4R,5R)-1,1,2,2,3,3,4,5-octafluorocyclopentane.

In some embodiments, the compound administered, or used with any of the methods set forth herein, is 1,1,2,2,3,3,4-heptafluorocyclopentane (CAS#15290-77-4). In certain embodiments, the compound has the structure selected from the group consisting of

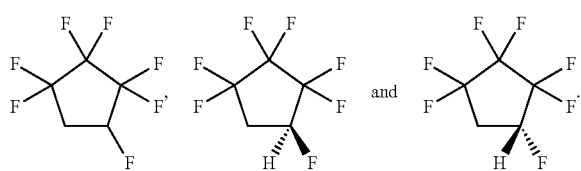

In certain embodiments, the compound administered, or used with any of the methods set forth herein, is selected from the group consisting of (R)-1,1,2,2,3,3,4-heptafluorocyclopentane and (S)-1,1,2,2,3,3,4-heptafluorocyclopentane. Mixtures, e.g., racemic mixtures, of (R)-1,1,2,2,3,3,4-heptafluorocyclopentane and (S)-1,1,2,2,3,3,4-heptafluorocyclopentane may be used with the methods set forth herein. The present invention also includes administering, or using with any of the methods set forth herein, a particular stereoisomer of 1,1,2,2,3,3,4-heptafluorocyclopentane (CAS#15290-77-4), e.g., (R)-1,1,2,2,3,3,4-heptafluorocyclopentane or (S)-1,1,2,2,3,3,4-heptafluorocyclopentane.

vi. Halogenated Cyclohexane Derivatives

An illustrative halogenated cyclohexane derivative includes without limitation 1,1,2,2,3,3,4,4-octafluoro-cyclohexane (CAS#830-15-9).

vii. Halogenated Tetrahydrofuran Derivatives

Illustrative halogenated tetrahydrofuran derivatives include without limitation a compound or a mixture of compounds of Formula VI:

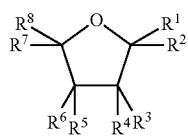

VI wherein:
$R^1$, $R^2$, $R^3$, $R^4$, $R^5$, $R^6$, $R^7$ and $R^8$ independently are selected from H, X, $CX_3$, $CHX_2$, $CH_2X$ and $C_2X_5$; and
wherein X is a halogen, the compound has a vapor pressure of less than 0.1 atmospheres (76 mmHg) at 25° C., and the number of hydrogen atoms of Formula VI do not exceed the number of carbon atoms. In various embodiments, X is a halogen selected from the group consisting of F, Cl, Br and I. In some embodiments, X is F. In some embodiments, $R^1$, $R^2$, $R^3$, $R^4$, $R^5$, $R^6$, $R^7$ and $R^8$ independently are selected from H, F, Cl, Br, I, $CF_3$, $CHF_2$, $CH_2F$, $C_2F_5$, $CCl_3$, $CHCl_2$, $CH_2Cl$, $C_2Cl_5$, $CCl_2F$, $CClF_2$, $CHClF$, $C_2ClF_4$, $C_2Cl_2F_3$, $C_2Cl_3F_2$, and $C_2Cl_4F$.

In some embodiments, the halogenated tetrahydrofuran derivatives are selected from the group consisting of:

a) Furan, 2,3,4,4-tetrafluorotetrahydro-2,3-bis(trifluoromethyl)- (CAS#634191-25-6);
b) Furan, 2,2,3,3,4,4,5-heptafluorotetrahydro-5-(trifluoromethyl)- (CAS#377-83-3);
c) Furan, 2,2,3,3,4,5,5-heptafluorotetrahydro-4-(trifluoromethyl)- (CAS#374-53-8);
d) Furan, 2,2,3,4,5-pentafluorotetrahydro-5-(trifluoromethyl)-, (2a,3β,4a)- (9CI) (CAS#133618-53-8);
e) Furan, 2,2,3,4,5-pentafluorotetrahydro-5-(trifluoromethyl)-, (2a,3a,4a)- (CAS#133618-52-7);
f) Furan, 2,2,3,4,5-pentafluorotetrahydro-5-(trifluoromethyl)-, (2α,3β,4α)- (9CI) (CAS#133618-53-8);
g) Furan, 2,2,3,4,5-pentafluorotetrahydro-5-(trifluoromethyl)-, (2α,3α,4β)- (9CI) (CAS#133618-52-7);
h) Furan, 2,2,3,3,5,5-hexafluorotetrahydro-4-(trifluoromethyl)- (CAS#61340-70-3);
i) Furan, 2,3-difluorotetrahydro-2,3-bis(trifluoromethyl)- (CAS#634191-26-7);
j) Furan, 2-chloro-2,3,3,4,4,5,5-heptafluorotetrahydro- (CAS#1026470-51-8);
k) Furan, 2,2,3,3,4,4,5-heptafluorotetrahydro-5-methyl- (CAS#179017-83-5);
l) Furan, 2,2,3,3,4,5-hexafluorotetrahydro-5-(trifluoromethyl)-, trans- (9CI) (CAS#133618-59-4); and
m) Furan, 2,2,3,3,4,5-hexafluorotetrahydro-5-(trifluoromethyl)-, cis- (9CI) (CAS#133618-49-2).

viii. Halogenated Tetrahydropyran Derivatives

Illustrative halogenated tetrahydropyran derivatives include without limitation a compound or a mixture of compounds of Formula VII:

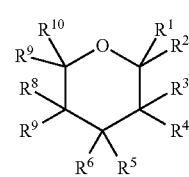

VII wherein:
$R^1$, $R^2$, $R^3$, $R^4$, $R^5$, $R^6$, $R^7$, $R^8$, $R^9$ and $R^{10}$ independently are selected from H, X, $CX_3$, $CHX_2$, $CH_2X$, and $C_2X_5$; and
wherein X is a halogen, the compound has a vapor pressure of less than 0.1 atmospheres (76 mmHg) at 25° C., and the number of hydrogen atoms of Formula VII do not exceed the number of carbon atoms. In various embodiments, X is a halogen selected from the group consisting of F, Cl, Br and I. In some embodiments, X is F. In some embodiments, $R^1$, $R^2$, $R^3$, $R^4$, $R^5$, $R^6$, $R^7$, $R^8$, $R^9$ and $R^{10}$ independently are selected from H, F, Cl, Br, I, $CF_3$, $CHF_2$, $CH_2F$, $C_2F_5$, $CCl_3$, $CHCl_2$, $CH_2Cl$, $C_2Cl_5$, $CCl_2F$, $CClF_2$, $CHClF$, $C_2ClF_4$, $C_2Cl_2F_3$, $C_2Cl_3F_2$, and $C_2Cl_4F$.

In some embodiments, the halogenated tetrahydropyran derivatives are selected from the group consisting of:

a) 2H-Pyran, 2,2,3,3,4,5,5,6,6-nonafluorotetrahydro-4- (CAS#71546-79-7);
b) 2H-Pyran, 2,2,3,3,4,4,5,5,6-nonafluorotetrahydro-6-(trifluoromethyl)- (CAS#356-47-8);
c) 2H-Pyran, 2,2,3,3,4,4,5,6,6-nonafluorotetrahydro-5-(trifluoromethyl)- (CAS#61340-74-7);
d) 2H-Pyran, 2,2,6,6-tetrafluorotetrahydro-4-(trifluoromethyl)- (CAS#657-48-7);
e) 2H-Pyran, 2,2,3,3,4,4,5,5,6-nonafluorotetrahydro-6-methyl- (CAS#874634-55-6);
f) Perfluorotetrahydropyran (CAS#355-79-3);
g) 2H-Pyran, 2,2,3,3,4,5,5,6-octafluorotetrahydro-, (4R,6S)-rel- (CAS#362631-93-4); and
h) 2H-Pyran, 2,2,3,3,4,4,5,5,6-nonafluorotetrahydro- (CAS#65601-69-6).

III. Subjects Who May Benefit

The anesthetic compounds and methods described herein find use for inducing anesthesia in any subject in need thereof. For example, the subject may be undergoing a surgical procedure that requires the induction of temporary unconsciousness and/or immobility.

The sedative compounds and methods described herein find use for inducing sedation in any subject in need thereof. For example, the subject may be undergoing a surgical procedure that requires a reduction in the patient's anxiety or the induction of a temporary calm or tranquil state in the subject.

The patient receiving the anesthetic may have been selected for having or at risk of having a sensitivity or adverse reaction to an anesthetic that activates a particular anesthetic-sensitive receptor or subset of anesthetic-receptors. For example, the patient may have or be at risk of having a sensitivity or adverse reaction to an anesthetic that activates one or more of NMDA receptors, two-pore potassium channels, voltage-gated ion channels, GABA receptors, glycine receptors, or another anesthetic-sensitive receptor. In such cases, the anesthetic administered to the patient has a water solubility that is less than the solubility threshold concentration for the receptor for which it is sought to avoid modulating.

In various embodiments, it may be desirable to induce in the subject amnesia and/or immobility by potentiating $GABA_A$ receptors, but minimize or avoid inducing possible respiratory or neurologic side-effects that may be associated with inhibition of NMDA receptors.

IV. Formulation and Administration a. Formulation

The invention also encompasses the use of pharmaceutical compositions comprising a compound or a mixture of compounds (e.g., of Formula I, Formula II, Formula III, Formula IV, Formula V, Formula VI, Formula VII and/or Formula VIII, as described herein), or salts thereof, to induce anesthesia in a subject.

The invention also encompasses the use of pharmaceutical compositions comprising a compound or a mixture of compounds (e.g., of Formula I, Formula II, Formula III, Formula IV, Formula V, Formula VI, Formula VII and/or Formula VIII, as described herein), or salts thereof, to induce sedation in a subject, wherein the compound has a vapor pressure less than 0.1 atm (76 mm Hg).

Such a pharmaceutical composition may consist of at least one compound of the invention or a salt thereof, in a form suitable for administration to a subject, or the pharmaceutical composition may comprise at least one compound of the invention or a salt thereof, and one or more pharmaceutically acceptable carriers, one or more additional ingredients, or some combination of these. The at least one compound of the invention may be present in the pharmaceutical composition in the form of a physiologically acceptable salt, such as in combination with a physiologically acceptable cation or anion, as is well known in the art.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the subject. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington: The Science and Practice of Pharmacy (Remington: The Science & Practice of Pharmacy), $21^{st}$ Edition, 2011, Pharmaceutical Press, and Ansel's Pharmaceutical Dosage Forms and Drug Delivery Systems, Allen, et al., eds., $9^{th}$ Edition, 2010, Lippincott Williams & Wilkins, which are incorporated herein by reference.

In various embodiments, the compounds are formulated for delivery via a respiratory pathway, e.g., suitably developed for inhalational, pulmonary, intranasal, delivery. In various embodiments, the compound or mixture of compounds is vaporized into or directly mixed or diluted with a carrier gas, e.g., oxygen, air, or helium, or a mixture thereof. A preservative may be further included in the vaporized formulations, as appropriate. Other contemplated formulations include projected nanoparticles, and liposomal preparations. The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals including agricultural mammals (e.g., cattle, pigs, horses, sheep), domesticated mammals (e.g., cats, and dogs), and laboratory mammals (e.g., rats, mice, rabbits, hamsters).

b. Administration

In some embodiments, the methods further comprise administering the selected anesthetic (e.g., a compound or mixture of compounds of Formula I, Formula II, Formula III, Formula IV, Formula V, Formula VI, Formula VII and/or Formula VIII, as described herein) to a patient. The anesthetic can be administered by any route sufficient to achieve a desired anesthetic, amnestic, analgesic, or sedative effect. For example, the anesthetic can be administered intravenously, inhalationally, subcutaneously, intramuscularly, transdermally, topically, or by any other route to achieve an efficacious effect.

The anesthetic is administered at a dose sufficient to achieve a desired anesthetic endpoint, for example, immobility, amnesia, analgesia, unconsciousness or autonomic quiescence.

Administered dosages for anesthetic agents are in accordance with dosages and scheduling regimens practiced by those of skill in the art. General guidance for appropriate dosages of pharmacological agents used in the present methods is provided in *Goodman and Gilman's The Pharmacological Basis of Therapeutics*, 12th Edition, 2010, supra, and in a Physicians' Desk Reference (PDR), for example, in the $65^{th}$ (2011) or $66^{th}$ (2012) Eds., PDR Network, each of which is hereby incorporated herein by reference.

The appropriate dosage of anesthetic agents will vary according to several factors, including the chosen route of administration, the formulation of the composition, patient response, the severity of the condition, the subject's weight, and the judgment of the prescribing physician. The dosage can be increased or decreased over time, as required by an individual patient. Usually, a patient initially is given a low dose, which is then increased to an efficacious dosage tolerable to the patient.

Determination of an effective amount is well within the capability of those skilled in the art, especially in light of the detailed disclosure provided herein. Generally, an efficacious or effective amount of a combination of one or more anesthetic agents is determined by first administering a low dose or small amount of the anesthetic, and then incrementally increasing the administered dose or dosages, adding a second or third medication as needed, until a desired effect is observed in the treated subject with minimal or no toxic side effects. Applicable methods for determining an appropriate dose and dosing schedule for administration of anesthetics are described, for example, in *Goodman and Gilman's The Pharmacological Basis of Therapeutics*, 12th Edition, 2010, supra; in a Physicians' Desk Reference (PDR), supra; in *Remington: The Science and Practice of Pharmacy* (*Remington: The Science & Practice of Pharmacy*). 21st Edition, 2011, Pharmaceutical Press, and *Ansel's Pharmaceutical Dosage Forms and Drug Delivery Systems*. Allen, et al., eds., 9th Edition, 2010, Lippincott Williams & Wilkins; and in *Martindale: The Complete Drug Reference*, Sweetman, 2005, London: Pharmaceutical Press., and in Martindale, *Martindale: The Extra Pharmacopoeia*, 31 st Edition., 1996, Amer Pharmaceutical Assn, each of which are hereby incorporated herein by reference.

Dosage amount and interval can be adjusted individually to provide plasma levels of the active compounds which are sufficient to maintain a desired therapeutic effect. Preferably, therapeutically effective serum levels will be achieved by administering a single dose, but efficacious multiple dose schedules are included in the invention. In cases of local administration or selective uptake, the effective local concentration of the drug may not be related to plasma concentration. One having skill in the art will be able to optimize therapeutically effective local dosages without undue experimentation.

The dosing of analog compounds can be based on the parent compound, at least as a starting point.

In various embodiments, the compositions are delivered to the subject via a respiratory pathway, e.g., via inhalational, pulmonary and/or intranasal delivery.

Technologies and devices for inhalational anesthetic drug dosing are known in the art and described, e.g., in MILLER'S ANESTHESIA, Edited by Ronald D. Miller, et al., 2 vols, 7th ed, Philadelphia, Pa., Churchill Livingstone/Elsevier, 2010; and Meyer, et al., *Handb Exp Pharmacol*. (2008) (182):451-70. In one embodiment, the pharmaceutical compositions useful for inducing anesthesia can be administered to deliver a dose of between about 0.1-10.0 percent of 1 atmosphere (1 atm), e.g., 0.5-5.0 percent of 1 atm, e.g., about 1.0-3.5 of 1 atm, e.g., about 0.1, 0.2, 0.3, 0.4. 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5 or 10.0 percent of 1 atm, e.g., delivered over the period of time of desired anesthesia. The dose used will be dependent upon the drug potency, and the compound or mixture of compounds administered.

In a second embodiment, the pharmaceutical compositions useful for inducing sedation can be administered to deliver a dose of between about 0.005-0.1 atmosphere. The dose used will be dependent upon the drug potency, and the compound or mixture of compounds administered.

Detailed information about the delivery of therapeutically active agents in the form of vapors or gases is available in the art. The compound will typically be vaporized using a vaporizer using a carrier gas such as oxygen, air, or helium, or a mixture thereof, to achieve a desired drug concentration suitable for inhalation by use of a semi-open or semi-closed anesthetic circuit, as is known to individuals familiar with the art of anesthesia. The compound in a gaseous form may also be directly mixed with a carrier gas such as oxygen, air, or helium, or a mixture thereof, to achieve a desired drug concentration suitable for inhalation by use of a semi-open or semi-closed anesthetic circuit, as is known to individuals familiar with the art of anesthesia. The drug may also be administered by direct application of onto or through a breathing mask, also termed an open circuit, as is known to individuals familiar with the art of anesthesia. In animals, the drug may also be administered into a closed chamber or container containing the animal subject whereby the drug is delivered by the respiratory tract as the animal breathes, as is known to individuals familiar with animal anesthesia.

In some aspects of the invention, the anesthetic compound or mixture of compounds, is dissolved or suspended in a suitable solvent, such as water, ethanol, or saline, and administered by nebulization. A nebulizer produces an aerosol of fine particles by breaking a fluid into fine droplets and dispersing them into a flowing stream of gas. Medical nebulizers are designed to convert water or aqueous solutions or colloidal suspensions to aerosols of fine, inhalable droplets that can enter the lungs of a patient during inhalation and deposit on the surface of the respiratory airways. Typical pneumatic (compressed gas) medical nebulizers develop approximately 15 to 30 microliters of aerosol per liter of gas in finely divided droplets with volume or mass median diameters in the respirable range of 2 to 4 micrometers. Predominantly, water or saline solutions are used with low solute concentrations, typically ranging from 1.0 to 5.0 mg/mL.

Nebulizers for delivering an aerosolized solution to the lungs are commercially available from a number of sources, including the AERx™ (Aradigm Corp., Hayward, Calif.) and the Acorn II* (Vital Signs Inc., Totowa, N.J.).

Metered dose inhalers are also known and available. Breath actuated inhalers typically contain a pressurized propellant and provide a metered dose automatically when the patient's inspiratory effort either moves a mechanical lever or the detected flow rises above a preset threshold, as detected by a hot wire anemometer. See, for example, U.S. Pat. Nos. 3,187,748; 3,565,070; 3,814,297; 3,826,413; 4,592,348; 4,648,393; 4,803,978; and 4,896,832.

In some embodiments, the present invention provides methods for producing analgesia in a subject, comprising administering to the subject via the respiratory system an effective amount of a compound or a mixture of compounds which are described herein. In some embodiments, the analgesia includes tranquilization. In some embodiments, the analgesia includes sedation. In some embodiments, the analgesia includes amnesia. In some embodiments, the analgesia includes a hypnotic state. In some embodiments, the analgesia includes a state of insensitivity to noxious stimulation.

In some embodiments, the present invention provides methods of producing tranquilization or sedation in a subject, comprising administering to the subject via the respiratory system an effective amount of a compound or a mixture of compounds which are described herein. In certain embodiments, the present invention provides methods of producing tranquilization in a subject, comprising administering to the subject via the respiratory system an effective amount of a compound or a mixture of compounds which are described herein. In some other embodiments, the present invention provides methods of producing amnesia in a subject, comprising administering to the subject via the respiratory system an effective amount of a compound or a mixture of compounds which are described herein. Typically, the amount of a compound or a mixture of compounds which are described herein that is required to produce amnesia in a subject is larger than the amount required to produce tranquilization in a subject. In yet other embodiments, the present invention provides methods of producing a hypnotic state in a subject, comprising administering to the subject via the respiratory system an effective amount of a compound or a mixture of compounds which are described herein. Typically, the amount of a compound or a mixture of compounds which are described herein that is required to produce a hypnotic state in a subject is larger than the amount required to produce amnesia in a subject. In still other embodiments, the present invention provides methods of producing a state of insensitivity to noxious stimulation in a subject, comprising administering to the subject via the respiratory system an effective amount of a compound or a mixture of compounds which are described herein. Typically, the amount of a compound or a mixture of compounds which are described herein that is required to produce a state of insensitivity to noxious stimulation in a subject is larger than the amount required to produce a hypnotic state in a subject.

In some embodiments, the present invention provides methods of inducing tranquilization or sedation in a subject, comprising administering to the subject via the respiratory system an effective amount of a compound or a mixture of compounds which are described herein. In certain embodiments, the present invention provides methods of inducing tranquilization in a subject, comprising administering to the subject via the respiratory system an effective amount of a compound or a mixture of compounds which are described herein. In some other embodiments, the present invention provides methods of inducing amnesia in a subject, comprising administering to the subject via the respiratory system an effective amount of a compound or a mixture of compounds which are described herein. Typically, the amount of a compound or a mixture of compounds which are described herein that is required to induce amnesia in a subject is larger than the amount required to induce tranquilization in a subject. In yet other embodiments, the present invention provides methods of inducing a hypnotic state in a subject, comprising administering to the subject via the respiratory system an effective amount of a compound or a mixture of compounds which are described herein. Typically, the amount of a compound or a mixture of compounds which are described herein that is required to induce a hypnotic state in a subject is larger than the amount required to induce amnesia in a subject. In still other embodiments, the present invention provides methods of inducing a state of insensitivity to noxious stimulation in a subject, comprising administering to the subject via the respiratory system an effective amount of a compound or a mixture of compounds which are described herein. Typically, the amount of a compound or a mixture of compounds which are described herein that is required to induce a state of insensitivity to noxious stimulation in a subject is larger than the amount required to induce a hypnotic state in a subject.

The present invention includes methods of inducing a spectrum of states of anesthesia in a subject as a function of the administered dosage of a compound or a mixture of compounds which are described herein. In some embodiments, the methods include administering low dosages of a compound or a mixture of compounds which are described herein to induce tranquilization or sedation in a subject. In some other embodiments, the methods include administering higher dosages than that required to induce tranquilization of a compound or a mixture of compounds which are described herein to induce amnesia in a subject. In yet other embodiments, the methods include administering even higher dosages than that required to induce amnesia in a subject of a compound or a mixture of compounds which are described herein to induce a hypnotic state in a subject. In still other embodiments, the methods include administering yet even higher dosages than that required to induce a hypnotic state in a subject of a compound or a mixture of compounds which are described herein to induce a state of insensitivity to noxious stimulation in a subject.

V. Methods of Determining the Specificity of an Anesthetic for an Anesthetic Sensitive Receptor The present invention provides methods for determining the specificity or selective activation of an anesthetic for an anesthetic-sensitive receptor by determining the water solubility of the anesthetic and comparing the water solubility of the anesthetic with a water solubility cut-off or threshold value for the anesthetic-sensitive receptor. An anesthetic with a water solubility that is below the water solubility cut-off or threshold value for the anesthetic-sensitive receptor will not activate that receptor. An anesthetic with a water solubility that is above the water solubility cut-off or threshold value for the anesthetic-sensitive receptor can activate that receptor.

a. Anesthetics

The anesthetic can be any compound with anesthetic properties when administered to a patient. Generally, increasing doses of an anesthetic causes immobility, amnesia, analgesia, unconsciousness and autonomic quiescence in a patient. The anesthetics are general anesthetics (e.g., systemic) and can be inhalational or injectable.

In some embodiments, the anesthetic is an inhalational anesthetic. For example, in some embodiments, the anesthetic is selected from the group consisting of ethers and halogenated ethers (including, e.g., desflurane, enflurane, halothane, isoflurane, methoxyflurane, sevoflurane, diethyl ether, methyl propyl ether, and analogues thereof); alkanes and halogenated alkanes (including, e.g., halothane, chloroform, ethyl chloride, and analogues thereof), cycloalkanes and cyclohaloalkanes (including, e.g., cyclopropane and analogues thereof), alkenes and haloalkenes (including, e.g., trichloroethylene, ethylene, and analogues thereof), alkynes and haloalkynes and their analogues, vinyl ethers (including, e.g., ethyl vinyl ether, divinyl ether, fluoroxine, and analogues thereof). In some embodiments, the anesthetic is selected from the group consisting of desflurane, enflurane, halothane, isoflurane, methoxyflurane, nitrous oxide, sevoflurane, xenon, and analogs thereof. In some embodiments, the anesthetic is selected from the group consisting of halogenated alcohols, halogenated diethers, halogenated dioxanes, halogenated dioxolanes, halogenated cyclopentanes, halogenated cyclohexanes, halogenated tetrahydrofurans and halogenated tetrahydropyrans, as described herein. In various embodiments, the inhalational anesthetic is a compound or mixture of compounds of Formula I, Formula II, Formula III, Formula IV, Formula V, Formula VI, Formula VII and/or Formula VIII, as described herein.

In some embodiments, the anesthetic is an injectable anesthetic or sedative drug. For example, in some embodiments, the anesthetic is selected from the group consisting of alkyl phenols (including, e.g., propofol and analogues thereof), imidazole derivatives (including, e.g., etomidate, metomidate, clonidine, detomidine, medetomidine, dexmedetomidine, and analogues thereof), barbiturates and analogues thereof, benzodiazepines and analogues thereof, cyclohexylamines (including, e.g., ketamine, tiletamine, and analogues thereof), steroid anesthetics (including, e.g., alphaxalone and analogues thereof), opioids and opioid-like compounds (including, e.g., natural morphine and derivatives, codeine and derivatives, papaverine and derivatives, thebaine and derivatives, morphinans and derivatives, diphenylpropylamines and derivatives, benzmorphans and derivatives, phenylpiperadines and derivatives), phenothiazines and halogenated phenothiazine compounds and analogues thereof, buterophenones and halogenated buterophenone compounds and analogues thereof, guaicols and halogenated guaicols (including, e.g., eugenol and analogues thereof), and substituted benzoates and halobenzoate derivatives (including, e.g., tricaine and analogues thereof). In some embodiments, the anesthetic is selected from the group consisting of propofol, etomidate, barbiturates, benzodiazepines, ketamine, and analogs thereof.

Anesthetic compounds are generally known in the art and are described in, e.g., *Goodman and Gilman's The Pharmacological Basis of Therapeutics,* 12th Edition, 2010, supra, and in a Physicians' Desk Reference (PDR), for example, in the $65^{th}$ (2011) or $66^{th}$ (2012) Eds., PDR Network.

b. Anesthetic-Sensitive Receptors

Anesthetic-sensitive receptors are receptors and ion channels that bind to and are activated by anesthetics. Anesthetic-sensitive receptors include 2-, 3-, 4-, and 7-transmembrane receptor proteins. Exemplary anesthetic-sensitive receptors include glycine receptors, GABA receptors, two-pore domain potassium channels ($K_{2P}$), voltage-gated sodium channels ($Na_v$), NMDA receptors, opioid receptors and subtypes of such receptors. Anesthetic-sensitive receptors are well-known in the art. Their sequences are well characterized.

N-methyl-D-aspartate (NMDA) receptor channels are heteromers composed of three different subunits: NR1 (GRIN1), NR2 (GRIN2A, GRIN2B, GRIN2C, or GRIN2D) and NR3 (GRIN3A or GRIN3B). The NR2 subunit acts as the agonist binding site for glutamate. This receptor is the predominant excitatory neurotransmitter receptor in the mammalian brain. NMDA receptors are reviewed, e.g., in Albensi, Curr Pharm Des (2007) 13(31):3185-94: Paoletti and Neyton, Curr Opin Pharmacol (2007) 7(1):39-47; Cull-Candy, et al., Curr Opin Neurobiol (2001) 11(3):327-35. The GenBank Accession Nos. for isoforms of human NMDA NR1 (NMDAR1, GRIN1) include NM_000832.6→NP_000823.4 (NR1-1), NM_021569.3→NP_067544.1 (NR1-2), NM_007327.3→NP_015566.1 (NR1-3), NM_001185090.1→NP_001172019.1 (NR1-4); NM_001185091.1→NP_001172020.1 (NR1-5); the GenBank Accession Nos. for isoforms of human NMDA NR2A (NMDAR2A, GRIN2A) include NM_000833.3→NP_000824.1 (isoform 1), NM_001134407.1→NP_001127879.1 (isoform 1), NM_001134408.1→NP_001127880.1 (isoform 2); the GenBank Accession No. for human NMDA NR2B (NMDAR2B, GRIN2B) includes NM_000834.3→NP_000825.2; the GenBank Accession No. for human NMDA NR2C (NMDAR2C, GRIN2C) includes NM_000835.3→NP_000826.2; the GenBank Accession No. for human NMDA NR2D (NMDAR2D, GRIN2D) includes NM_000836.2→NP_000827.2; the GenBank Accession No. for human NMDA NR3A (NMDAR3A, GRIN3A) includes NM_133445.2→NP_597702.2; the GenBank Accession No. for human NMDA NR3B (NMDAR3B, GRIN3B) includes NM_138690.1→NP_619635.1. NMDA receptor sequences are also well-characterized for non-human mammals.

Gamma-aminobutyric acid (GABA)-A receptors are pentameric, consisting of proteins from several subunit classes: alpha, beta, gamma, delta and rho. GABA receptors are reviewed, e.g., in Belelli, et al., J Neurosci (2009) 29(41): 12757-63; and Munro, et al., Trends Pharmacol Sci (2009) 30(9):453-9. GenBank Accession Nos. for variants of human GABA-A receptor, alpha 1 (GABRA1) include NM_000806.5→NP_000797.2 (variant 1), NM_001127643.1→NP_001121115.1 (variant 2), NM_001127644.1→NP_001121116.1 (variant 3), NM_001127645.1→NP_001121117.1 (variant 4), NM_001127646.1→NP_001121118.1 (variant 5), NM_001127647.1→NP_001121119.1 (variant 6), NM_001127648.1→NP_001121120.1 (variant 7). GenBank Accession Nos. for variants of human GABA-A receptor, alpha 2 (GABRA2) include NM_000807.2→NP_000798.2 (variant 1), NM_001114175.1→NP_001107647.1 (variant 2). GenBank Accession No. for human GABA-A receptor, alpha 3 (GABRA3) includes NM_000808.3→NP_000799.1. GenBank Accession Nos. for variants of human GABA-A receptor, alpha 4 (GABRA4) include NM_000809.3→NP_000800.2 (variant 1), NM_001204266.1→NP_001191195.1 (variant 2), NM_001204267.1→NP_001191196.1 (variant 3). GenBank Accession Nos. for variants of human GABA-A receptor, alpha 5 (GABRA5) include NM_000810.3→NP_000801.1 (variant 1), NM_001165037.1→NP_001158509.1 (variant 2). GenBank Accession No. for human GABA-A receptor, alpha 6 (GABRA6) includes NM_000811.2→NP_000802.2. GenBank Accession No. for human GABA-A receptor, beta 1 (GABRB1) includes NM_000812.3→NP_000803.2. GenBank Accession Nos. for variants of human GABA-A receptor, beta 2 (GABRB2) include NM_021911.2→NP_068711.1 (variant 1), NM_000813.2→NP_000804.1 (variant 2). GenBank Accession Nos. for variants of human GABA-A receptor, beta 3 (GABRB3) include NM_000814.5→NP_000805.1 (variant 1), NM_021912.4→NP_068712.1 (variant 2), NM_001191320.1→NP_001178249.1 (variant 3), NM_001191321.1→NP_001178250.1 (variant 4). GenBank Accession No. for human GABA-A receptor, gamma 1 (GABRG1) includes NM_173536.3→NP_775807.2. GenBank Accession Nos. for variants of human GABA-A receptor, gamma 2 (GABRG2) include NM_198904.2→NP_944494.1 (variant 1), NM_000816.3→NP_000807.2 (variant 2), NM_198903.2→NP_944493.2 (variant 3). GenBank Accession No. for human GABA-A receptor, gamma 3 (GABRG3) includes NM_033223.4→NP_150092.2. GenBank Accession Nos. for variants of human GABA-A receptor, rho 1 (GABRR1) include NM_002042.4→NP_002033.2 (variant 1), NM_001256703.1→NP_001243632.1 (variant 2), NM_001256704.1→NP_001243633.1 (variant 3), NM_001267582.1→NP_001254511.1 (variant 4). GenBank Accession No. for human GABA-A receptor, rho 2 (GABRR2) includes NM_002043.2→NP_002034.2. GenBank Accession No. for human GABA-A receptor, rho 3 (GABRR3) includes NM_001105580.2→NP_001099050.1.

Voltage-sensitive sodium channels are heteromeric complexes consisting of a large central pore-forming glycosylated alpha subunit, and two smaller auxiliary beta subunits. Voltage-gated sodium channels are reviewed, e.g., in French and Zamponi, IEEE Trans Nanobioscience (2005) 4(1):58-69; Bezanilla, IEEE Trans Nanobioscience (2005) 4(1):34-48; Doherty and Farmer, Handb Exp Pharmacol (2009) 194:519-61; England, Expert Opin Investig Drugs (2008) 17(12): 1849-64; and Marban, et al., J Physiol (1998) 508(3):647-57. GenBank Accession Nos. for variants of sodium channel, voltage-gated, type I, alpha subunit (SCN1A, Nav1.1) include NM_001165963.1→NP_001159435.1 (variant 1), NM_006920.4→NP_008851.3 (variant 2), NM_001165964.1→NP_001159436.1 (variant 3), NM_001202435.1→NP_001189364.1 (variant 4). GenBank Accession Nos. for variants of sodium channel, voltage-gated, type II, alpha subunit (SCN2A, Nav1.2) include NM_021007.2→NP_066287.2 (variant 1), NM_001040142.1→NP_001035232.1 (variant 2), NM_001040143.1→NP_001035233.1 (variant 3). GenBank Accession Nos. for variants of sodium channel, voltage-gated, type III, alpha subunit (SCN3A, Nav1.3) include NM_006922.3→NP_008853.3 (variant 1), NM_001081676.1→NP_001075145.1 (variant 2), NM_001081677.1→NP_001075146.1 (variant 3). GenBank Accession No. for sodium channel, voltage-gated, type IV, alpha subunit (SCN4A, Nav1.4) includes NM_000334.4→NP_000325.4. GenBank Accession Nos. for variants of sodium channel, voltage-gated, type V, alpha subunit (SCN5A, Nav1.5) include NM_198056.2→NP_932173.1 (variant 1), NM_000335.4→NP_000326.2 (variant 2), NM_001099404.1→NP_001092874.1 (variant 3), NM_001099405.1→NP_001092875.1 (variant 4), NM_001160160.1→NP_001153632.1 (variant 5), NM_001160161.1→NP_001153633.1 (variant 6). GenBank Accession No. for sodium channel, voltage-gated, type VII, alpha subunit (SCN6A, SCN7A, Nav2.1, Nav2.2) includes NM_002976.3→NP_002967.2. GenBank Accession Nos. for variants of sodium channel, voltage-gated, type VIII, alpha subunit (SCN8A, Nav1.6) include NM_014191.3→NP_055006.1 (variant 1), NM_001177984.2→NP_001171455.1 (variant 2). GenBank Accession No. for sodium channel, voltage-gated, type IX, alpha subunit (SCN9A, Nav1.7) includes NM_002977.3→NP_002968.1. GenBank Accession No. for sodium channel, voltage-gated, type X, alpha subunit (SCN10A, Nav1.8) includes NM_006514.2→NP_006505.2. GenBank Accession No. for sodium channel, voltage-gated, type XI, alpha subunit (SCN11A, Nav1.9) includes NM_014139.2→NP_054858.2. GenBank Accession Nos. for variants of sodium channel, voltage-gated, type I, beta subunit (SCN1B) include NM_001037.4→NP_001028.1 (variant a), NM_199037.3→NP_950238.1 (variant b). GenBank Accession No. for sodium channel, voltage-gated, type II, beta subunit (SCN2B) includes NM_004588.4→NP_004579.1. GenBank Accession Nos. for variants of sodium channel, voltage-gated, type III, beta subunit (SCN3B) include NM_018400.3→NP_060870.1 (variant 1), NM_001040151.1→NP_001035241.1 (variant 2). GenBank Accession Nos. for variants of sodium channel, voltage-gated, type IV, beta subunit (SCN4B) include NM_174934.3→NP_777594.1 (variant 1), NM_001142348.1→NP_001135820.1 (variant 2), NM_001142349.1→NP_001135821.1 (variant 3).

Glycine receptors are pentamers composed of alpha and beta subunits. Glycine receptors are reviewed, e.g., in Kuhse, et al., Curr Opin Neurobiol (1995) 5(3):318-23; Betz, et al., Ann NY Acad Sci (1999) 868:667-76; Colquhoun and Sivilotti, Trends Neurosci (2004) 27(6):337-44; and Cascio, J Biol Chem (2004) 279(19): 19383-6. GenBank Accession Nos. for variants of glycine receptor, alpha 1 (GLRA1) include NM_001146040.1→NP_001139512.1 (variant 1), NM_000171.3→NP_000162.2 (variant 2). GenBank Accession Nos. for variants of glycine receptor, alpha 2 (GLRA2) include NM_002063.3→NP_002054.1 (variant 1), NM_001118885.1→NP_001112357.1 (variant 2), NM_001118886.1→NP_001112358.1 (variant 3), NM_001171942.1→NP_001165413.1 (variant 4). GenBank Accession Nos. for variants of glycine receptor, alpha 3 (GLRA3) include NM_006529.3→NP_006520.2 (isoform a), NM_001042543.1→NP_001036008.1 (isoform b). GenBank Accession Nos. for variants of glycine receptor, alpha 4 (GLRA4) include NM_001024452.2→NP_001019623.2

(variant 1), NM_001172285.1→NP_001165756.1 (variant 2). GenBank Accession Nos. for variants of glycine receptor, beta (GLRB) include NM_000824.4→NP_000815.1 (variant 1), NM_001166060.1→NP_001159532.1 (variant 2), NM_001166061.1→NP_001159533.1 (variant 3).

Two-pore potassium channels are reviewed, e.g., in Besana, et al., Prostaglandins Other Lipid Mediat (2005) 77(1-4): 103-10; Lesage and Lazdunski, Am J Physiol Renal Physiol (2000) 279(5):F793-801; Bayliss and Barrett, Trends Pharmacol Sci (2008) 29(11):566-75; Reyes, et al., J Biol Chem (1998) 273(47):30863-9; and Kang and Kim, Am J Physiol Cell Physiol (2006) 291(1):C138-46. GenBank Accession Nos. for variants of potassium channel, subfamily K, member 2 (KCNK2, TREK1, K2p2.1) include NM_001017424.2→NP_001017424.1 (variant 1), NM_014217.3→NP_055032.1 (variant 2), NM_001017425.2→NP_001017425.2 (variant 3). GenBank Accession No. for potassium channel, subfamily K, member 3 (KCNK3, TASK; TBAK1; K2p3.1) includes NM_002246.2→NP_002237.1. GenBank Accession No. for potassium channel, subfamily K, member 6 (KCNK6, KCNK8; TWIK2; K2p6.1) includes 1.NM_004823.1→NP_004814.1.

c. Determining Water Solubility of the Anesthetic

The water solubility of the anesthetic can be determined using any method known in the art. For example, the water solubility can be determined using a computer implemented algorithm. One such algorithm is available through Sci-Finder Scholar provided by the American Chemical Society and available on the worldwide web at scifinder.cas.org. Water solubility values using SciFinder Scholar are calculated using Advanced Chemistry Development (ACD/Labs) Software V9.04 for Solaris (1994-2009 ACD/Labs). Solubility values are calculated at pH=7 in pure water at 25° C. Other computer-implemented algorithms for determining the water solubility of an anesthetic find use and are known in the art. For example, software for calculating water solubility is also commercially available from Advanced Chemistry Development of Toronto, Ontario, Canada (on the worldwide web at acdlabs.com). Chemix software is available without charge and can be downloaded from the internet at home.c2i.net/astandne.

Alternatively, the water solubility of a compound can be empirically determined. For example, the conditions in which anesthetic effects are measured in a biological system are usually at pH (7.4), in a buffered electrolyte solution at 22-23° C. These differences likely account for the small variation in the NMDA solubility cutoff for different hydrocarbon groups shown in FIG. 4.

d. Determining the Specificity of the Anesthetic for the Anesthetic-Sensitive Receptor The water solubility of the anesthetic is compared with the solubility cut-off or threshold concentration of an anesthetic-sensitive receptor. If the molar water solubility of the anesthetic is less than the solubility cut-off or threshold concentration of an anesthetic-sensitive receptor, then the anesthetic will not activate that anesthetic-sensitive receptor. If the water solubility of the anesthetic is greater than the solubility cut-off or threshold concentration of an anesthetic-sensitive receptor, then the anesthetic can activate that anesthetic-sensitive receptor.

For example, in some embodiments, an anesthetic with a molar water solubility below a predetermined solubility threshold concentration for $Na_v$ channels does not inhibit $Na_v$ channels, but can inhibit NMDA receptors, potentiate two-pore domain potassium channels ($K_{2P}$), potentiate glycine receptors and potentiate $GABA_A$ receptors.

In some embodiments, an anesthetic with a molar water solubility below a predetermined solubility threshold concentration for NMDA receptors does not inhibit $Na_v$ channels or inhibit NMDA receptors, but can potentiate two-pore domain potassium channels ($K_{2P}$), potentiate glycine receptors and potentiate $GABA_A$ receptors.

In some embodiments, an anesthetic with a molar water solubility below a predetermined solubility threshold concentration for two-pore domain potassium channels ($K_{2P}$) does not inhibit $Na_v$ channels, inhibit NMDA receptors or potentiate two-pore domain potassium channel ($K_{2P}$) currents, but can potentiate glycine receptors and potentiate $GABA_A$ receptors.

In some embodiments, an anesthetic with a molar water solubility below a predetermined solubility threshold concentration for $GABA_A$ receptors does not inhibit $Na_v$ channels, inhibit NMDA receptors, potentiate two-pore domain potassium channel ($K_{2P}$) currents, or potentiate $GABA_A$ receptors but can potentiate glycine receptors.

In some embodiments, the anesthetic has a molar water solubility below a predetermined solubility threshold concentration for NMDA receptors (e.g., below about 1.1 mM) and potentiates $GABA_A$ receptors but does not inhibit NMDA receptors. In some embodiments, the anesthetic has a water solubility greater than a predetermined solubility threshold concentration for NMDA receptors (e.g., greater than about 1.1 mM) and both potentiates $GABA_A$ receptors and inhibits NMDA receptors.

In various embodiments, the solubility threshold concentration for NMDA receptors is in the range of between about 0.45 mM and about 2.8 mM, for example between about 1 mM and about 2 mM, for example, about, 0.1 mM, 0.2 mM, 0.3 mM, 0.4 mM, 0.5 mM, 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM or 2.0 mM. In some embodiments, the predetermined solubility threshold concentration for NMDA receptors is about 1.1 mM. In some embodiments, the predetermined solubility threshold concentration for NMDA receptors is about 2 mM. In some embodiments, the anesthetic has a molar water solubility that is below the threshold water solubility cut-off concentration of an NMDA receptor, and therefore does not inhibit the NMDA receptor. In some embodiments, the anesthetic has a water solubility that is below about 2 mM, for example, below about 2.0 mM, 1.9 mM, 1.8 mM, 1.7 mM, 1.6 mM, 1.5 mM, 1.4 mM, 1.3 mM, 1.2 mM, 1.1 mM or 1.0 mM. In some embodiments, the anesthetic has a water solubility that is above the threshold water solubility cut-off concentration of an NMDA receptor, and therefore can inhibit the NMDA receptor. In some embodiments, the anesthetic has a molar water solubility that is above about 1.0 mM, for example, above about 1.1 mM, 1.2 mM, 1.3 mM, 1.4 mM, 1.5 mM, 1.6 mM, 1.7 mM, 1.8 mM, 1.9 mM or 2.0 mM.

In various embodiments, the solubility threshold concentration for two-pore domain potassium channels ($K_{2P}$) receptors is in the range of about 0.10-1.0 mM, for example, about 0.10 mM, 0.20 mM, 0.26 mM, 0.30 mM, 0.35 mM, 0.40 mM, 0.45 mM, 0.50 mM, 0.55 mM, 0.60 mM, 0.65 mM, 0.70 mM, 0.75 mM, 0.80 mM, 0.85 mM, 0.90 mM, 0.95 mM or 1.0 mM. In some embodiments, the predetermined solubility threshold concentration for two-pore domain potassium channels ($K_{2P}$) receptors is about 0.26 mM. In some embodiments, two-pore domain potassium channels ($K_{2P}$) receptor is a TREK or a TRESK receptor. In some embodiments, the anesthetic has a molar water solubility that is below the threshold water solubility cut-off concentration of a two-pore domain potassium channels ($K_{2P}$) receptor (e.g., below about 0.26 mM), and therefore does not potentiate the two-pore domain potassium channels ($K_{2P}$) receptor. In some embodiments, the anesthetic has a molar water solubility that is above the threshold water solubility cut-off concentration of a two-pore domain potassium channels ($K_{2P}$) receptor (e.g., above about 0.26 mM), and therefore can potentiate the two-pore domain potassium channels ($K_{2P}$) receptor.

In various embodiments, the solubility threshold concentration for voltage-gated sodium channels ($Na_v$) is in the range of about 1.2 to about 1.9 mM, for example, about 1.2 mM, 1.3 mM, 1.4 mM, 1.5 mM, 1.6 mM, 1.7 mM, 1.8 mM or 1.9 mM. In some embodiments, the predetermined solubility threshold concentration for voltage-gated sodium channels ($Na_v$) is about 1.2 mM. In some embodiments, the predetermined solubility threshold concentration for voltage-gated sodium channels ($Na_v$) is about 1.9 mM. In some embodiments, the anesthetic has a molar water solubility that is below the threshold water solubility cut-off concentration of a voltage-gated sodium channel ($Na_v$) (e.g., below about 1.2 mM), and therefore does not inhibit the voltage-gated sodium channel ($Na_v$). In some embodiments, the anesthetic has a water solubility that is above the threshold water solubility cut-off concentration of a voltage-gated sodium channel ($Na_v$) (e.g., above about 1.9 mM) and therefore can inhibit the voltage-gated sodium channel ($Na_v$).

In various embodiments, the solubility threshold concentration for $GABA_A$ receptors is in the range of about 50-100 µM, for example, about 50 µM, 60 µM, 65 µM, 68 µM, 70 µM, 75 µM, 80 µM, 85 µM, 90 µM, 95 µM or 100 µM. In some embodiments, the predetermined solubility threshold concentration for $GABA_A$ receptors is about 68 µM. In some embodiments, the anesthetic has a molar water solubility that is below the threshold water solubility cut-off concentration of a $GABA_A$ receptor (e.g., below about 68 µM), and therefore does not potentiate the $GABA_A$ receptor. In some embodiments, the anesthetic has a water solubility that is above the threshold water solubility cut-off concentration of a $GABA_A$ receptor (e.g., above about 68 µM), and therefore can potentiate the $GABA_A$ receptor.

In certain other embodiments, the solubility threshold concentration for $GABA_A$ receptors is in the range of about 37-100 µM, for example, about 37 µM, 39 µM, 40 µM, 45 µM, 50 µM, 60 µM, 65 µM, 68 M, 70 µM, 75 µM, 80 µM, 85 µM, 90 µM, 95 µM or 100 µM. In some embodiments, the predetermined solubility threshold concentration for $GABA_A$ receptors is about 68 µM. In some embodiments, the anesthetic has a molar water solubility that is below the threshold water solubility cut-off concentration of a $GABA_A$ receptor (e.g., below about 68 µM), and therefore does not potentiate the $GABA_A$ receptor. In some embodiments, the anesthetic has a water solubility that is above the threshold water solubility cut-off concentration of a $GABA_A$ receptor (e.g., above about 68 µM), and therefore can potentiate the $GABA_A$ receptor.

In various embodiments, the solubility threshold concentration for glycine receptors is in the range of about 0.7-to-89 µM, for example, about 0.7 µM, 3.9 µM, 7.8 µM, 17 µM, 31 µM, 62 µM, or 89 µM. In some embodiments, the predetermined solubility threshold concentration for glycine receptors is about 7.8 µM. In some embodiments, the anesthetic has a molar water solubility that is below the threshold water solubility cut-off concentration of a glycine receptor, and therefore does not activate the glycine receptor. In some embodiments, the anesthetic has a water solubility that is above the threshold water solubility cut-off concentration of a glycine receptor.

In certain embodiments, the solubility threshold concentration for glycine receptors is in the range of about 0.19 to 0.4 µM, for example, about 0.19 µM, 0.2 µM, 0.25 µM, 0.3 µM, 31 µM, 62 µM, or 89 µM. In some embodiments, the predetermined solubility threshold concentration for glycine receptors is about 7.8 µM. In some embodiments, the anesthetic has a molar water solubility that is below the threshold water solubility cut-off concentration of a glycine receptor, and therefore does not activate the glycine receptor. In some embodiments, the anesthetic has a water solubility that is above the threshold water solubility cut-off concentration of a glycine receptor.

In certain embodiments, the solubility threshold concentration for TREK channels is in the range of about 170-330 µM, for example, about 170 µM, 180 µM, 190 µM, 200 µM, 210 µM, 230 µM, 240 µM, 250 µM, 260 µM, 270 µM, 280 µM, 290 µM, 300 µM, 310 µM, 320 µM, or 330 µM. In some embodiments, the anesthetic has a molar water solubility that is below the threshold water solubility cut-off concentration of a TREK channel, and therefore does not activate the TREK channel. In some embodiments, the anesthetic has a water solubility that is above the threshold water solubility cut-off concentration of a TREK channel.

In certain embodiments, the solubility threshold concentration for TRESK channels is in the range of about 280-780 µM, for example, about 280 µM, 320 µM, 340 µM, 360 µM, 380 µM, 400 µM, 420 µM, 440 µM, 460 µM, 480 µM, 500 µM, 520 µM, 540 µM, 560 µM, 580 µM, 600 µM, 620 µM, 640 µM, 660 µM, 680 µM, 700 µM, 720 µM, 740 µM, 760 µM, or 780 µM. In some embodiments, the anesthetic has a molar water solubility that is below the threshold water solubility cut-off concentration of a TRESK channel, and therefore does not activate the TRESK channel. In some embodiments, the anesthetic has a water solubility that is above the threshold water solubility cut-off concentration of a TRESK channel.

In certain embodiments, the solubility threshold concentration for $Na_v1.2$ channels is in the range of about 690-1200 µM, for example, about 690 µM, 710 µM, 730 µM, 750 µM, 770 µM, 790 µM, 810 µM, 820 µM, 840 µM, 860 µM, 880 µM, 900 µM, 910 µM, 930 µM, 940 µM, 960 µM, 980 µM, 1000 µM, 1050 µM, 1100 µM, 1150 µM, 1170 µM, 1190 µM, or 1200 µM. In some embodiments, the anesthetic has a molar water solubility that is below the threshold water solubility cut-off concentration of a $Na_v$ 1.2 channel, and therefore does not activate the $Na_v1.2$ channel. In some embodiments, the anesthetic has a water solubility that is above the threshold water solubility cut-off concentration of a $Na_v1.2$ channel.

In certain embodiments, the solubility threshold concentration for $Na_v1.4$ channels is in the range of about 510-1000 µM, for example, about 510 µM, 530 µM, 550 µM, 570 µM, 590 µM, 610 µM, 620 µM, 740 µM, 760 µM, 780 µM, 880 µM, 900 µM, 930 µM, 940 µM, 960 µM, 980 µM, or 1000 µM. In some embodiments, the anesthetic has a molar water solubility that is below the threshold water solubility cut-off concentration of a $Na_v$ 1.4 channel, and therefore does not activate the $Na_v1.4$ channel. In some embodiments, the anesthetic has a water solubility that is above the threshold water solubility cut-off concentration of a $Na_v1.4$ channel.

e. Selecting the Desired Anesthetic

In some embodiments, the methods further comprise the step of selecting an appropriate or desired anesthetic, e.g., based on the subset of anesthetic-sensitive receptors that can be activated by the anesthetic.

For example, the selected anesthetic can have a water solubility below a predetermined solubility threshold concentration for $Na_v$ channels (e.g., below about 1.2 mM), such that the anesthetic does not inhibit $Na_v$ channels, but can inhibit NMDA receptors, potentiate two-pore domain potassium channels ($K_{2P}$), potentiate glycine receptors and potentiate $GABA_A$ receptors.

In some embodiments, the selected anesthetic can have a water solubility below a predetermined solubility threshold concentration for NMDA receptors (e.g., below about 1.1 mM) such that the anesthetic does not inhibit $Na_v$ channels or inhibit NMDA receptors, but can potentiate two-pore domain potassium channels ($K_{2P}$), potentiate glycine receptors and potentiate $GABA_A$ receptors.

In some embodiments, the selected anesthetic can have a water solubility below a predetermined solubility threshold concentration for two-pore domain potassium channels ($K_{2P}$) (e.g., below about 0.26 mM) such that the anesthetic does not inhibit $Na_v$ channels, inhibit NMDA receptors or potentiate two-pore domain potassium channel ($K_{2P}$) currents, but can potentiate glycine receptors and potentiate $GABA_A$ receptors.

In some embodiments, the selected anesthetic can have a water solubility below a predetermined solubility threshold concentration for $GABA_A$ receptors (e.g., below about 68 µM) such that the anesthetic does not inhibit $Na_v$ channels, inhibit NMDA receptors, potentiate two-pore domain potassium channel ($K_{2P}$) currents, or potentiate $GABA_A$ receptors but can potentiate glycine receptors.

In some embodiments, the selected anesthetic can have a water solubility below a predetermined solubility threshold concentration for NMDA receptors (e.g., below about 1.1 mM) such that the anesthetic potentiates $GABA_A$ receptors but does not inhibit NMDA receptors. In some embodiments, the anesthetic has a water solubility greater than a predetermined solubility threshold concentration for NMDA receptors (e.g., greater than about 1.1 mM) and both potentiates $GABA_A$ receptors and inhibits NMDA receptors.

In some embodiments, the selected anesthetic has a water solubility such that the anesthetic does not activate NMDA receptors, two-pore domain potassium channels (K2P), voltage-gated sodium channels (Nav), or GABAA receptors, but can activate glycine receptors. The anesthetic may have a water solubility that is less than about 7.8 µM.

The selected anesthetics usually have a water solubility that is greater than 7.8 µM.

VI. Methods of Modulating the Specificity of an Anesthetic for an Anesthetic-Sensitive Receptor by Altering the Water Solubility of the Anesthetic The invention also provides methods for modulating (i.e., increasing or decreasing) the specificity of an anesthetic for an anesthetic-sensitive receptor or a subset of anesthetic-sensitive receptors by adjusting the water solubility of the anesthetic. The anesthetic can be chemically modified or altered to increase or decrease the water solubility and hence the specificity of the anesthetic for the anesthetic-sensitive receptor or the subset of anesthetic-sensitive receptors.

In various embodiments, this method can be performed by determining the water solubility of the parent anesthetic and then comparing the water solubility of the parent anesthetic threshold cut-off value of an anesthetic-sensitive receptor, as described above. If the water solubility of the anesthetic is below the water solubility threshold cut-off concentration of the anesthetic-sensitive receptor, then the anesthetic will not modulate the receptor. If the capacity to modulate the anesthetic-sensitive receptor is desired, the water solubility of the anesthetic can be sufficiently increased, e.g., by chemically modifying the parent anesthetic, such that the analog of the parent anesthetic has a water solubility above the water solubility threshold cut-off concentration of the receptor or the subset of receptors of interest. In this case, the analog of the parent anesthetic can modulate the anesthetic-sensitive receptor or a subset of anesthetic-sensitive receptors of interest.

Conversely, if the water solubility of the anesthetic is above the water solubility threshold cut-off concentration of the anesthetic-sensitive receptor, then the anesthetic can modulate the receptor. If the capacity to modulate the anesthetic-sensitive receptor is not desired, then the water solubility of the anesthetic can be sufficiently decreased, e.g., by chemically modifying the parent anesthetic, such that the analog of the parent anesthetic has a water solubility below the water solubility threshold cut-off concentration of the anesthetic-sensitive receptor or the subset of receptors of interest. In this case, the analog of the parent anesthetic does not modulate the receptors or subset of receptors of interest.

The water solubility of the parent anesthetic can be adjusted using methods well known in the art. For example, the parent anesthetic can be chemically modified. Substituents on the parent anesthetic can be added, removed or changed, to increase or decrease the water solubility of the compound, as desired. The resulting analogs of the parent anesthetic either gain or lose the functional ability to activate the anesthetic-sensitive receptor, as desired, and have an increased or decreased water solubility, respectively, in comparison to the parent anesthetic. The anesthetic analogs of use retain the functional ability to effect anesthesia. The potency and/or efficacy of the anesthetic analogs, however, may be increased or decreased in comparison to the parent anesthetic.

For example, to decrease the water solubility of the anesthetic, polar or heteroatom substituents, e.g., hydroxyl or amino groups, can be removed or substituted with more hydrophobic substituents, e.g., a halogen or an alkyl group. Water solubility can also be decreased, e.g., by increasing the number of carbons on alkyl substituents, e.g., alkane, alkene, alkyne, alkoxy, etc. One, two, three, four, or more carbons can be added to the alkyl substituent, as needed, to decrease the water solubility of the anesthetic, as desired.

Conversely, to increase the water solubility of the anesthetic, hydrophobic substituents, e.g., a halogen or an alkyl group, can be removed or substituted with polar or heteroatom substituents, e.g., hydroxyl or amino groups. Water solubility can also be increased, e.g., by decreasing the number of carbons on alkyl substituents, e.g., alkane, alkene, alkyne, alkoxy, etc. One, two, three, four, or more carbons can be removed from the alkyl substituent, as needed, to increase the water solubility of the anesthetic, as desired.

For example, in some embodiments, the anesthetic is adjusted to have a water solubility below a predetermined solubility threshold concentration for NMDA receptors (e.g., below about 1.1 mM) such that the anesthetic does not inhibit $Na_v$ channels or inhibit NMDA receptors, but can potentiate two-pore domain potassium channels ($K_{2P}$), potentiate glycine receptors and potentiate $GABA_A$ receptors. The water solubility threshold concentrations for the different anesthetic-sensitive receptors are as described above and herein.

In some embodiments, the anesthetic is adjusted to have a water solubility below a predetermined solubility threshold concentration for two-pore domain potassium channels ($K_{2P}$) (e.g., below about 0.26 mM) such that the anesthetic does not inhibit $Na_v$ channels, inhibit NMDA receptors or potentiate two-pore domain potassium channel ($K_{2P}$) currents, but can potentiate glycine receptors and potentiate $GABA_A$ receptors.

In some embodiments, the anesthetic is adjusted to have a water solubility below a predetermined solubility threshold concentration for voltage-gated sodium channels ($Na_v$) (e.g., below about 1.2 mM) such that the anesthetic does not inhibit $Na_v$ channels, but can inhibit NMDA receptors, potentiate two-pore domain potassium channels ($K_{2P}$), potentiate glycine receptors and potentiate $GABA_A$ receptors.

In some embodiments, the anesthetic is adjusted to have a water solubility above a predetermined solubility threshold concentration for NMDA receptors (e.g., above about 1.1 mM) such that the anesthetic can both potentiate $GABA_A$ receptors and inhibit NMDA receptors.

In various embodiments, the anesthetic is adjusted to have a water solubility that is below the threshold water solubility cut-off concentration of an NMDA receptor, and therefore does not activate the NMDA receptor. In some embodiments, an anesthetic is adjusted to have a water solubility that is below about 2 mM, for example, below about 2.0 mM, 1.9 mM, 1.8 mM, 1.7 mM, 1.6 mM, 1.5 mM, 1.4 mM, 1.3 mM, 1.2 mM, 1.1 mM or 1.0 mM. In some embodiments, an anesthetic is adjusted to have a water solubility that is below about 1.1 mM. In some embodiments, the anesthetic is adjusted to have a water solubility that is above the threshold water solubility cut-off concentration of an NMDA receptor. In some embodiments, an anesthetic is adjusted to have a water solubility that is above about 1.0 mM, for example, above about 1.1 mM, 1.2 mM, 1.3 mM, 1.4 mM, 1.5 mM, 1.6 mM, 1.7 mM, 1.8 mM, 1.9 mM or 2.0 mM. In some embodiments, an anesthetic is adjusted to have a water solubility that is above about 1.1 mM.

In some embodiments, the anesthetic is adjusted to have a water solubility that is below the threshold water solubility cut-off concentration of a two-pore domain potassium channels ($K_{2P}$) receptor, and therefore does not potentiate the two-pore domain potassium channels ($K_{2P}$) receptor. In some embodiments, the anesthetic is adjusted to have a water solubility that is below about 0.10 mM, 0.20 mM, 0.26 mM, 0.30 mM, 0.35 mM, 0.40 mM, 0.45 mM, 0.50 mM, 0.55 mM, 0.60 mM, 0.65 mM, 0.70 mM, 0.75 mM, 0.80 mM, 0.85 mM, 0.90 mM, 0.95 mM or 1.0 mM. In some embodiments, the anesthetic is adjusted to have a water solubility that is below about 0.26 mM. In some embodiments, the anesthetic is adjusted to have a water solubility that is above the threshold water solubility cut-off concentration of a two-pore domain potassium channels ($K_{2P}$) receptor, and therefore can potentiate the two-pore domain potassium channels ($K_{2P}$) receptor. In some embodiments, the anesthetic is adjusted to have a water solubility that is above about 0.10 mM, 0.20 mM, 0.26 mM, 0.30 mM, 0.35 mM, 0.40 mM, 0.45 mM, 0.50 mM, 0.55 mM, 0.60 mM, 0.65 mM, 0.70 mM, 0.75 mM, 0.80 mM, 0.85 mM, 0.90 mM, 0.95 mM or 1.0 mM. In some embodiments, the anesthetic is adjusted to have a water solubility that is above about 0.26 mM. In some embodiments, two-pore domain potassium channels ($K_{2P}$) receptor is a TREK or a TRESK receptor.

In some embodiments, the anesthetic is adjusted to have a water solubility that is below the threshold water solubility cut-off concentration of a voltage-gated sodium channel ($Na_v$), and therefore does not inhibit the voltage-gated sodium channel ($Na_v$). In some embodiments, the anesthetic is adjusted to have a water solubility that is below about 1.2 mM, 1.3 mM, 1.4 mM, 1.5 mM, 1.6 mM, 1.7 mM, 1.8 mM or 1.9 mM. In some embodiments, the anesthetic is adjusted to have a water solubility that is below about 1.2 mM. In some embodiments, the anesthetic is adjusted to have a water solubility that is above the threshold water solubility cut-off concentration of a voltage-gated sodium channel ($Na_v$), and therefore can inhibit the voltage-gated sodium channel ($Na_v$). In some embodiments, the anesthetic is adjusted to have a water solubility that is above about 1.2 mM, 1.3 mM, 1.4 mM, 1.5 mM, 1.6 mM, 1.7 mM, 1.8 mM or 1.9 mM. In some embodiments, the anesthetic is adjusted to have a water solubility that is above about 1.9 mM.

In some embodiments, the anesthetic is adjusted to have a water solubility that is below the threshold water solubility cut-off concentration of a $GABA_A$ receptor, and therefore does not potentiate the $GABA_A$ receptor. In some embodiments, the anesthetic is adjusted to have a water solubility that is below about 37 µM, 39 µM, 41 µM, 43 µM, 45 µM, 47 µM, 49 µM, 50 µM, 60 µM, 65 µM, 68 µM, 70 µM, 75 µM, 80 µM, 85 µM, 90 µM, 95 µM or 100 µM. In some embodiments, the anesthetic is adjusted to have a water solubility that is below about 68 µM. In some embodiments, the anesthetic is adjusted to have a water solubility that is above the threshold water solubility cut-off concentration of a $GABA_A$ receptor, and therefore can potentiate the $GABA_A$ receptor. In some embodiments, the anesthetic is adjusted to have a water solubility that is above about 50 µM, 60 µM, 65 µM, 68 µM, 70 µM, 75 µM, 80 µM, 85 µM, 90 µM, 95 µM or 100 µM. In some embodiments, the anesthetic is adjusted to have a water solubility that is above about 68 µM.

In some embodiments, the anesthetic is adjusted to have a water solubility that is below the threshold water solubility cut-off concentration of a glycine receptor, and therefore does not potentiate the glycine receptor. In some embodiments, the anesthetic is adjusted to have a water solubility that is above the threshold water solubility cut-off concentration of a glycine receptor, and therefore can potentiate the glycine receptor. The solubility cut-off for the glycine receptor is about 7.8 µM, but may range between 0.7 and 89 µM.

In some embodiments, the methods further comprise the step of selecting the anesthetic analog with the desired water solubility. In some embodiments, the methods further comprise the step of administering the anesthetic analog, as described above and herein.

EXAMPLES

The following examples are offered to illustrate, but not to limit the claimed invention.

Example 1

Hydrocarbon Molar Water Solubility Predicts NMDA Vs. $GABA_A$ Receptor Modulation Background: Many anesthetics modulate 3-transmembrane (such as NMDA) and 4-transmembrane (such as $GABA_A$) receptors. Clinical and experimental anesthetics exhibiting receptor family specificity often have low water solubility. We determined that the molar water solubility of a hydrocarbon could be used to predict receptor modulation in vitro.

Methods: $GABA_A$ ($\alpha_1\beta_2\gamma_{2s}$) or NMDA (NR1/NR2A) receptors were expressed in oocytes and studied using standard two-electrode voltage clamp techniques. Hydrocarbons from 14 different organic functional groups were studied at saturated concentrations, and compounds within each group differed only by the carbon number at the ω-position or within a saturated ring. An effect on GABA$_A$ or NMDA receptors was defined as a 10% or greater reversible current change from baseline that was statistically different from zero.

Results: Hydrocarbon moieties potentiated GABA$_A$ and inhibited NMDA receptor currents with at least some members from each functional group modulating both receptor types. A water solubility cut-off for NMDA receptors occurred at 1.1 mM with a 95% CI=0.45 to 2.8 mM. NMDA receptor cut-off effects were not well correlated with hydrocarbon chain length or molecular volume. No cut-off was observed for GABA$_A$ receptors within the solubility range of hydrocarbons studied.

Conclusions: Hydrocarbon modulation of NMDA receptor function exhibits a molar water solubility cut-off. Differences between unrelated receptor cut-off values suggest that the number, affinity, or efficacy of protein-hydrocarbon interactions at these sites likely differ.

Methods

Oocyte Collection and Receptor Expression. An ovary from tricaine-anesthetized *Xenopus laevis* frogs was surgically removed using a protocol approved by the Institutional Animal Care and Use Committee at the University of California, Davis. Following manual disruption of the ovarian lobule septae, the ovary was incubated in 0.2% Type I collagenase (Worthington Biochemical, Lakewood, N.J.) to defolliculate oocytes which were washed and stored in fresh and filtered modified Barth's solution composed of 88 mM NaCl, 1 mM KCl, 2.4 mM NaHCO$_3$, 20 mM HEPES, 0.82 mM MgSO$_4$, 0.33 mM Ca(NO$_3$)$_2$, 0.41 mM CaCl$_2$, 5 mM sodium pyruvate, gentamycin, penicillin, streptomycin, and corrected to pH=7.4. All salts and antibiotics were A.C.S. grade (Fisher Scientific, Pittsburgh, Pa.).

Clones used were provided as a gift from Dr. R. A. Harris (University of Texas, Austin) and were sequenced and compared to references in the National Center for Biotechnology Information database to confirm the identity of each gene. GABA$_A$ receptors were expressed using clones for the human GABA$_A$ α1 and the rat GABA$_A$ β2 and γ2s subunits in pCIS-II vectors. Approximately 0.25-1 ng total plasmid mixture containing either α1, β2, or γ2 genes in a respective ratio of 1:1:10 was injected intranuclearly through the oocyte animal pole and studied 2-4 days later. These plasmid ratios ensured incorporation of the γ-subunit into expressed receptors, as confirmed via receptor potentiation to 10 μM chlordiazepoxide or insensitivity to 10 μM zinc chloride during co-application with GABA. In separate oocytes, glutamate receptors were expressed using rat NMDA NR1 clones in a pCDNA3 vector and rat NMDA NR2A clones in a Bluescript vector. RNA encoding each subunit was prepared using a commercial transcription kit (T7 mMessage mMachine, Ambion, Austin, Tex.) was mixed in a 1:1 ratio, and 1-10 ng of total RNA was injected into oocytes and studied 1-2 days later. Oocytes injected with similar volumes of water served as controls.

GABA$_A$ Receptor Electrophysiology Studies. Oocytes were studied in a 250 μL linear-flow perfusion chamber with solutions administered by syringe pump at 1.5 ml/min with gastight glass syringes and Teflon tubing. Oocyte GABAA currents were studied using standard two-electrode voltage clamping techniques at a holding potential of 80 mV using a 250 μL channel linear-flow perfusion chamber with solutions administered by syringe pump at 1.5 mL/min.

Frog Ringer's (FR) solution composed of 115 mM NaCl, 2.5 mM KCl, 1.8 mM CaCl$_2$, and 10 mM HEPES prepared in 18.2 MΩ H$_2$O and filtered and adjusted to pH=7.4 was used to perfuse oocytes. Agonist solutions also contained an EC10-20 of 4-aminobutanoic acid (FR-GABA) (Brosnan, et al., *Anesth Analg* (2006) 103:86-91; Yang, et al., *Anesth Analg* (2007) 105:673-679; Yang, et al., *Anesth Analg* (2007) 105:393-396). After FR perfusion for 5 min, oocytes were exposed to 30 sec FR-GABA followed by another 5 min FR washout; this was repeated until stable GABA$_A$-elicited peaks were obtained. Next, FR containing a saturated solution of the study drug (Table 2)—or for gaseous study compounds a vapor pressure equal to 90% of barometric pressure with balance oxygen—was used to perfuse the oocyte chamber for 2 min followed by perfusion with a FR-GABA solution containing the identical drug concentration for 30 sec. FR was next perfused for 5 min to allow drug washout, and oocytes were finally perfused with FR-GABA for 30 sec to confirm return of currents to within 10% of the initial baseline response.

Table 2

Source, purity and physical properties of study compounds. Chemical Abstracts Service number (CAS#), molecular weight (MW), vapor pressure at 25° C. (Pvap), molar solubility in pure water at pH=7, and molecular volume are calculated estimates (rather than measured values) referenced by SciFinder Scholar.

TABLE 2

| Compound | CAS# | MW (amu) | $P_{vap}$ (mmHg) | Solubility (M) | Carbon (#) | Volume (Å$^3$) | Source | Purity (%) |
|---|---|---|---|---|---|---|---|---|
| Alcohols | | | | | | | | |
| 1-decanol | 112-30-1 | 158.28 | $1.48 \times 10^{-2}$ | $6.5 \times 10^{-4}$ | 10 | 317 | Aldrich | >99 |
| 1-undecanol | 112-42-5 | 172.31 | $5.10 \times 10^{-3}$ | $1.7 \times 10^{-4}$ | 11 | 344 | Acros | 98 |
| 1-dodecanol | 112-53-8 | 186.33 | $2.09 \times 10^{-3}$ | $4.1 \times 10^{-5}$ | 12 | 372 | TCI | 99 |
| Alkanes | | | | | | | | |
| butane | 106-97-8 | 58.12 | $1.92 \times 10^{3}$ | $1.4 \times 10^{-3}$ | 4 | 156 | Matheson | 99.99 |
| pentane | 109-66-0 | 72.15 | $5.27 \times 10^{2}$ | $4.3 \times 10^{-4}$ | 5 | 184 | Aldrich | >99 |
| hexane | 110-54-3 | 86.18 | $1.51 \times 10^{2}$ | $1.2 \times 10^{-4}$ | 6 | 211 | Acros | >99 |
| Aldehydes | | | | | | | | |
| octanal | 124-13-0 | 128.21 | $2.07 \times 10^{0}$ | $5.4 \times 10^{-3}$ | 8 | 262 | Aldrich | 99 |
| nonanal | 124-19-6 | 142.24 | $5.32 \times 10^{-1}$ | $2.3 \times 10^{-3}$ | 9 | 289 | Aldrich | 95 |
| decanal | 112-31-2 | 156.27 | $2.07 \times 10^{-1}$ | $9.8 \times 10^{-4}$ | 10 | 316 | Aldrich | 98 |
| undecanal | 112-44-7 | 170.29 | $8.32 \times 10^{-2}$ | $4.2 \times 10^{-4}$ | 11 | 344 | Aldrich | 97 |

TABLE 2-continued

| Compound | CAS# | MW (amu) | $P_{vap}$ (mmHg) | Solubility (M) | Carbon (#) | Volume (Å³) | Source | Purity (%) |
|---|---|---|---|---|---|---|---|---|
| Alkenes | | | | | | | | |
| 1-pentene | 109-67-1 | 70.13 | $6.37 \times 10^2$ | $1.4 \times 10^{-3}$ | 5 | 176 | Aldrich | 99 |
| 1-hexene | 592-41-6 | 84.16 | $1.88 \times 10^2$ | $4.2 \times 10^{-4}$ | 6 | 203 | Aldrich | >99 |
| Alkynes | | | | | | | | |
| 1-hexyne | 693-02-7 | 82.14 | $1.35 \times 10^2$ | $2.9 \times 10^{-3}$ | 6 | 184 | Aldrich | 97 |
| 1-heptyne | 628-71-7 | 96.17 | $4.35 \times 10^1$ | $6.6 \times 10^{-4}$ | 7 | 212 | Acros | 99 |
| 1-octyne | 629-05-0 | 110.2 | $1.44 \times 10^1$ | $1.9 \times 10^{-4}$ | 8 | 239 | Acros | 99 |
| Amines | | | | | | | | |
| 1-octadecanamine | 124-30-1 | 269.51 | $4.88 \times 10^{-5}$ | $1.3 \times 10^{-3}$ | 18 | 546 | TCI | 97 |
| 1-eicosanamine | 10525-37-8 | 297.56 | $8.96 \times 10^{-6}$ | $2.7 \times 10^{-4}$ | 20 | 601 | Rambus | 95 |
| Benzenes | | | | | | | | |
| 1,3-dimethylbenzene | 108-38-3 | 106.17 | $7.61 \times 10^0$ | $1.2 \times 10^{-3}$ | 8 | 202 | Aldrich | >99 |
| 1,3-diethylbenzene | 141-93-5 | 134.22 | $1.15 \times 10^0$ | $6.6 \times 10^{-5}$ | 10 | 257 | Fluka | >99 |
| Cycloalkanes | | | | | | | | |
| cyclopentane | 287-92-3 | 70.13 | $3.14 \times 10^2$ | $3.3 \times 10^{-3}$ | 5 | 147 | Aldrich | >99 |
| cyclohexane | 110-82-7 | 84.16 | $9.37 \times 10^1$ | $1.0 \times 10^{-3}$ | 6 | 176 | Aldrich | >99.7 |
| Ethers | | | | | | | | |
| dibutylether | 142-96-1 | 130.23 | $7.10 \times 10^0$ | $1.6 \times 10^{-2}$ | 8 | 277 | Aldrich | 99.3 |
| dipentylether | 693-65-2 | 158.28 | $1.00 \times 10^0$ | $3.0 \times 10^{-3}$ | 10 | 331 | Fluka | >98.5 |
| dihexylether | 112-58-3 | 186.33 | $1.48 \times 10^{-1}$ | $5.8 \times 10^{-4}$ | 12 | 386 | Aldrich | 97 |
| Esters | | | | | | | | |
| ethyl heptanoate | 106-30-9 | 158.24 | $6.02 \times 10^{-1}$ | $5.4 \times 10^{-3}$ | 9 | 299 | MP Bio | 99 |
| ethyl octanoate | 106-32-1 | 172.26 | $2.24 \times 10^{-1}$ | $2.1 \times 10^{-3}$ | 10 | 327 | Aldrich | >99 |
| ethyl decanoate | 110-38-3 | 200.32 | $3.39 \times 10^{-2}$ | $4.4 \times 10^{-4}$ | 12 | 381 | TCI | 98 |
| Haloalkanes | | | | | | | | |
| 1-fluoropentane | 592-50-7 | 90.14 | $1.84 \times 10^2$ | $3.9 \times 10^{-3}$ | 5 | 193 | Aldrich | 98 |
| 1-fluorohexane | 373-14-8 | 104.17 | $6.06 \times 10^1$ | $1.2 \times 10^{-3}$ | 6 | 220 | Acros | >99 |
| 1-fluoroctane | 463-11-6 | 132.22 | $7.09 \times 10^0$ | $1.3 \times 10^{-4}$ | 8 | 275 | Aldrich | 98 |
| Ketones | | | | | | | | |
| 2-decanone | 693-54-9 | 156.27 | $2.48 \times 10^{-1}$ | $3.2 \times 10^{-3}$ | 10 | 316 | TCI | >99 |
| 2-undecanone | 112-12-9 | 170.29 | $9.78 \times 10^{-2}$ | $1.4 \times 10^{-3}$ | 11 | 343 | Acros | 98 |
| 2-dodecanone | 6175-49-1 | 184.32 | $3.96 \times 10^{-2}$ | $5.8 \times 10^{-4}$ | 12 | 371 | TCI | 95 |
| Sulfides | | | | | | | | |
| 1-(ethylthio)-hexane | 7309-44-6 | 146.29 | $8.16 \times 10^{-1}$ | $2.8 \times 10^{-3}$ | 8 | 289 | Pfaltz | 97 |
| 1-(ethylthio)-octane | 3698-94-0 | 174.35 | $1.08 \times 10^{-1}$ | $5.0 \times 10^{-4}$ | 10 | 344 | Pfaltz | 97 |
| Thiols | | | | | | | | |
| 1-pentanethiol | 110-66-7 | 104.21 | $1.42 \times 10^1$ | $1.5 \times 10^{-3}$ | 5 | 207 | Aldrich | 98 |
| 1-hexanethiol | 111-31-9 | 118.24 | $4.50 \times 10^0$ | $5.1 \times 10^{-4}$ | 6 | 235 | TCI | 96 |

NMDA Receptor Electrophysiology Studies. Methods for measurement of whole-cell NMDA receptor currents have been described (Brosnan, et al., Br J Anaesth (2008) 101: 673-679; Brosnan, et al., Anesth Analg (2011) 112:568-573). Briefly, baseline perfusion solutions were the same as for $GABA_A$ with the substitution of equimolar $BaCl_2$ for calcium salts and the addition of 0.1 mM EGTA; this constituted barium frog Ringer's solution (BaFR). Agonist solutions for NMDA studies also contained 0.1 mM glutamate (E) and 0.01 mM glycine (G) to constitute a BaFREG solution.

The syringe pump and perfusion chamber apparatus as well as the clamp holding potential and baseline-agonist exposure protocols were identical to that described for the $GABA_A$ studies. The same test compounds, concentrations, and preparative methods were used in NMDA voltage clamp studies as in the $GABA_A$ voltage clamp studies (Table 2).

Response Calculations and Data Analysis. Modulating drug responses were calculated as the percent of the control (baseline) peak as follows:

$$100 \cdot \frac{I_D}{I_B},$$

where $I_D$ and $I_B$ were the peak currents measured during agonist+drug and agonist baseline perfusions, respectively. When present, direct receptor activation by a drug was similarly calculated as a percent of the agonist response. Average current responses for each drug and channel were described by mean±SD. A lack of receptor response (cut-off) was defined as a <10% change from baseline current that was statistically indistinguishable from zero using a two-tailed Student t-test. Hence, drug responses ≥110% of the baseline peak showed potentiation of receptor function, and drug responses ≤90% of the baseline peak showed inhibition of receptor function.

The $\log_{10}$ of the calculated solubility ($\log_{10}$ S) for compounds immediately below and above the cut-off for each hydrocarbon functional group were used to determine the receptor cut-off. For each hydrocarbon, there was a "grey area" of indeterminate solubility effect (FIG. 3) between sequentially increasing hydrocarbon chain length. Mean solubility cut-offs were calculated as the average $\log_{10} S$ for the least soluble compound that modulated receptor function and the most soluble neighboring compound for which no effect was observed. From this result, a 95% confidence interval for $\log_{10} S$ was calculated for receptor solubility cut-offs.

Results

Figure 3:
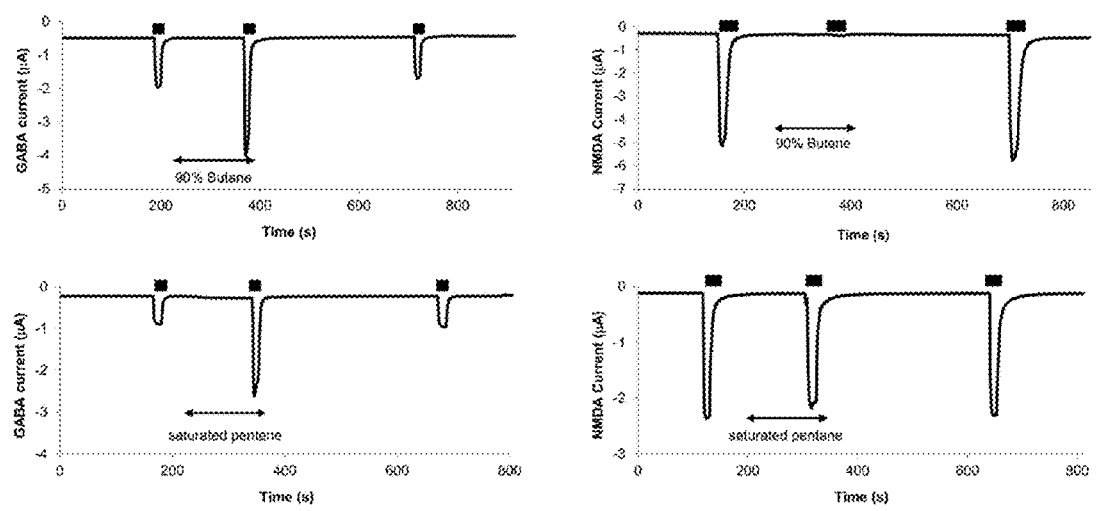
FIG. 3 illustrates sample two-electrode voltage clamp recordings from oocytes expressing either $GABA_A$ receptors (left) or NMDA receptors (right). Black bars (—) represent periods of agonist exposure, and arrows (↔) represent periods of saturated alkane exposure. Both butane and pentane positively modulate $GABA_A$ receptors. Butane negatively modulates NMDA receptors, but pentane produces no effect. Hence, NMDA receptors exhibit an alkane cut-off between butane and pentane.

Hydrocarbon effects on NMDA and $GABA_A$ receptors are summarized in Table 3, and sample recordings are presented in FIG. 3. All of the compounds tested positively modulated GABAA receptor function, and a few of the 5-to-6 carbon compounds caused mild direct GABAA receptor activation, particularly the 1-fluoroalkanes and thiols. Mild direct receptor activation also occurred with dibutylether. With the exception of the aldehydes, alkynes, and cycloalkanes, GABAA receptor inhibition tended to decrease with increasing hydrocarbon chain length. No water solubility cut-off effect was observed for GABAA receptors for the compounds tested.

Table 3

Mean responses (±SEM) produced by 14 different functional groups on NMDA and GABAA receptor modulation, expressed as a percent of the control agonist peak, using standard two-electrode voltage clamp techniques with 5-6 oocytes each. The % Direct Effect is the drug response without co-administration of the receptor agonist. The % Agonist Effect is the drug response with co-administration of agonist (glutamate and glycine for NMDA receptors; γ-aminobutyric acid for GABAA receptors). The Drug Response denotes inhibition (−) for drug+agonist responses less than the control agonist peak, potentiation (+) for drug+agonist responses greater than the control agonist peak, and no response (0) for drug+agonist responses that differ by <10% from the control agonist peak.

TABLE 3

| | NMDA | | | $GABA_A$ | | |
|---|---|---|---|---|---|---|
| Compound | % Direct Effect | % Agonist Effect | Drug Response | % Direct Effect | % Agonist Effect | Drug Response |
| Alcohols | | | | | | |
| 1-decanol | none | 70 ± 3 | — | none | 386 ± 20 | + |
| 1-undecanol | none | 101 ± 2 | 0 | none | 181 ± 13 | + |
| 1-dodecanol | none | 98 ± 1 | 0 | none | 177 ± 4 | + |
| Alkanes | | | | | | |
| butane | none | 7 ± 2 | — | none | 623 ± 68 | + |
| pentane | none | 94 ± 3 | 0 | none | 321 ± 10 | + |
| hexane | none | 100 ± 1 | 0 | none | 129 ± 5 | + |
| Aldehydes | | | | | | |
| octanal | none | 71 ± 3 | — | 6 ± 3 | 357 ± 20 | + |
| nonanal | none | 104 ± 2 | 0 | none | 219 ± 29 | + |
| decanal | none | 97 ± 3 | 0 | none | 159 ± 5 | + |
| undecanal | none | 97 ± 8 | 0 | none | 299 ± 29 | + |
| Alkenes | | | | | | |
| 1-pentene | none | 69 ± 1 | — | 2 ± 3 | 453 ± 38 | + |
| 1-hexene | none | 97 ± 0 | 0 | none | 132 ± 2 | + |
| Alkynes | | | | | | |
| 1-hexyne | none | 41 ± 6 | — | 5 ± 2 | 418 ± 21 | + |
| 1-heptyne | none | 68 ± 10 | — | none | 172 ± 8 | + |
| 1-octyne | none | 96 ± 2 | 0 | none | 259 ± 11 | + |
| Amines | | | | | | |
| 1-octadecanamine | none | 73 ± 4 | — | none | 146 ± 5 | + |
| 1-eicosanamine | none | 108 ± 1 | 0 | none | 166 ± 7 | + |
| Benzenes | | | | | | |
| 1,3-dimethylbenzene | none | 58 ± 3 | — | none | 366 ± 21 | + |
| 1,3-diethylbenzene | none | 101 ± 2 | 0 | none | 305 ± 24 | + |
| Cycloalkanes | | | | | | |
| cyclopentane | none | 83 ± 2 | — | 3 ± 2 | 196 ± 11 | + |
| cyclohexane | none | 101 ± 2 | 0 | none | 421 ± 17 | + |
| Ethers | | | | | | |
| dibutylether | none | 59 ± 4 | — | 14 ± 13 | 347 ± 33 | + |
| dipentylether | none | 97 ± 2 | 0 | none | 211 ± 9 | + |
| dihexylether | none | 112 ± 4 | 0 | none | 113 ± 1 | + |
| Esters | | | | | | |
| ethyl heptanoate | none | 78 ± 3 | — | none | 370 ± 34 | + |
| ethyl octanoate | none | 90 ± 1 | — | none | 285 ± 18 | + |
| ethyl decanoate | none | 98 ± 1 | 0 | none | 137 ± 2 | + |

TABLE 3-continued

| Compound | NMDA | | | GABA$_A$ | | |
|---|---|---|---|---|---|---|
| | % Direct Effect | % Agonist Effect | Drug Response | % Direct Effect | % Agonist Effect | Drug Response |
| Haloalkanes | | | | | | |
| 1-fluoropentane | none | 76 ± 2 | — | none | 539 ± 35 | + |
| 1-fluorohexane | none | 101 ± 1 | 0 | 11 ± 4 | 207 ± 13 | + |
| 1-fluoroctane | none | 98 ± 1 | 0 | none | 182 ± 18 | + |
| Ketones | | | | | | |
| 2-decanone | none | 81 ± 1 | — | none | 476 ± 52 | + |
| 2-undecanone | none | 98 ± 2 | 0 | none | 230 ± 16 | + |
| 2-dodecanone | none | 97 ± 3 | 0 | none | 325 ± 30 | + |
| Sulfides | | | | | | |
| 1-(ethylthio)-hexane | none | 87 ± 1 | — | none | 350 ± 57 | + |
| 1-(ethylthio)-octane | none | 101 ± 1 | 0 | none | 120 ± 3 | + |
| Thiols | | | | | | |
| 1-pentanethiol | none | 85 ± 4 | — | 22 ± 8 | 466 ± 57 | + |
| 1-hexanethiol | none | 102 ± 3 | 0 | 8 ± 2 | 290 ± 41 | + |

In contrast, NMDA receptors currents were decreased by the shorter hydrocarbons within each functional group (Table 2), but lengthening the hydrocarbon chain eventually produced a null response—a cut-off effect. No direct hydrocarbon effects on NMDA receptor function were detected in the absence of glutamate and glycine agonist.

Figure 4:
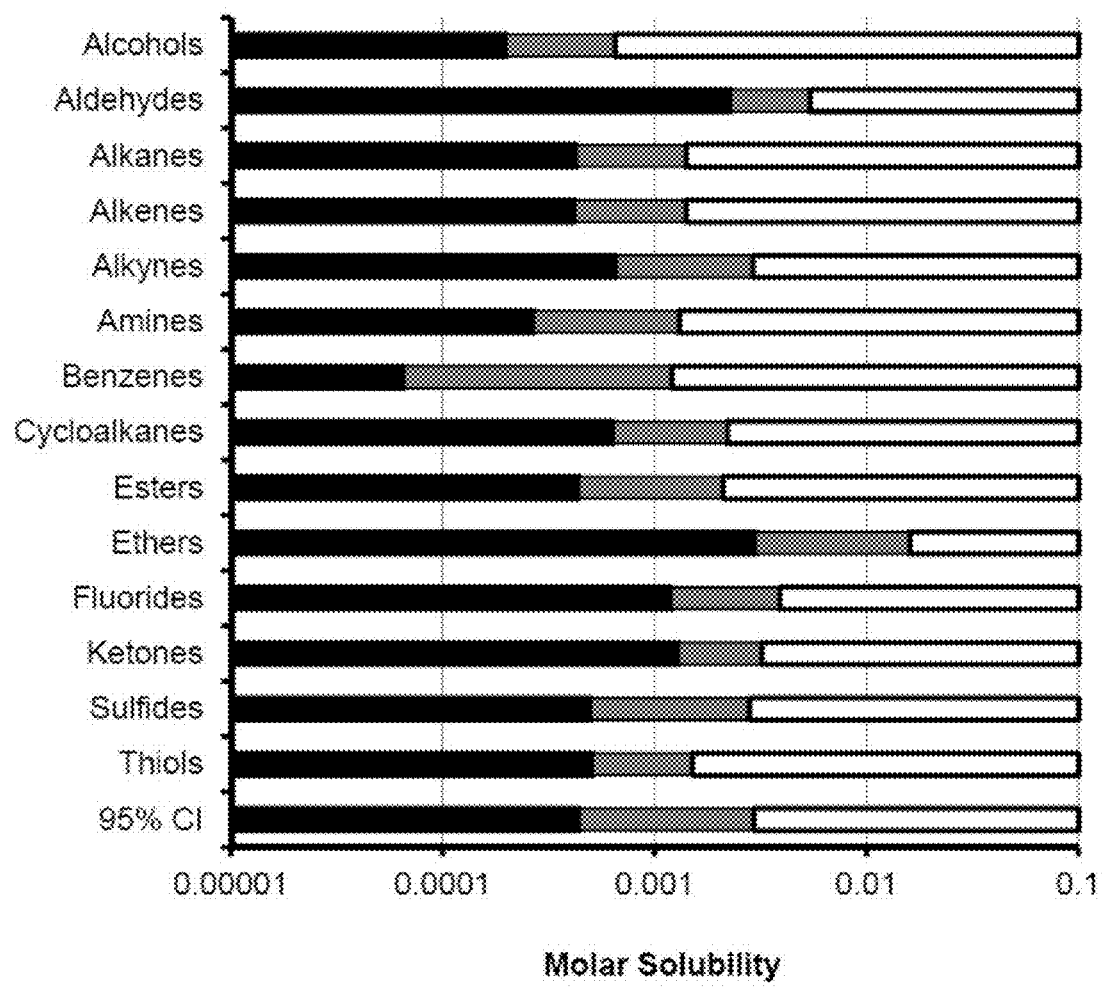
FIG. 4 illustrates a summary of receptor cut-off effects as a function of molar water solubility. For each hydrocarbon functional group, white bars represent compounds that modulate both $GABA_A$ and NMDA receptors, and black bars represent compounds that modulate $GABA_A$ receptors but have no effect on NMDA receptors at a saturating concentration. Intervening grey bars represent solubility values for which no data exist.

The cut-off effect for NMDA receptor current modulation was associated with a hydrocarbon water solubility of 1.1 mM with a 95% confidence interval between 0.45 mM and 2.8 mM (FIG. 4). More soluble hydrocarbons consistently inhibited NMDA receptor currents when applied at saturated aqueous concentrations, and hydrocarbons below this range had no appreciable effect on NMDA receptor function. Moreover, during the course of the study, water solubility was sufficiently predictive of an NMDA receptor cut-off so as to require identify and testing of only single pair of compounds bracketing this critical solubility value, as occurred with the alkenes, amines, cyclic hydrocarbons, and sulfur-containing compounds.

Figure 5:
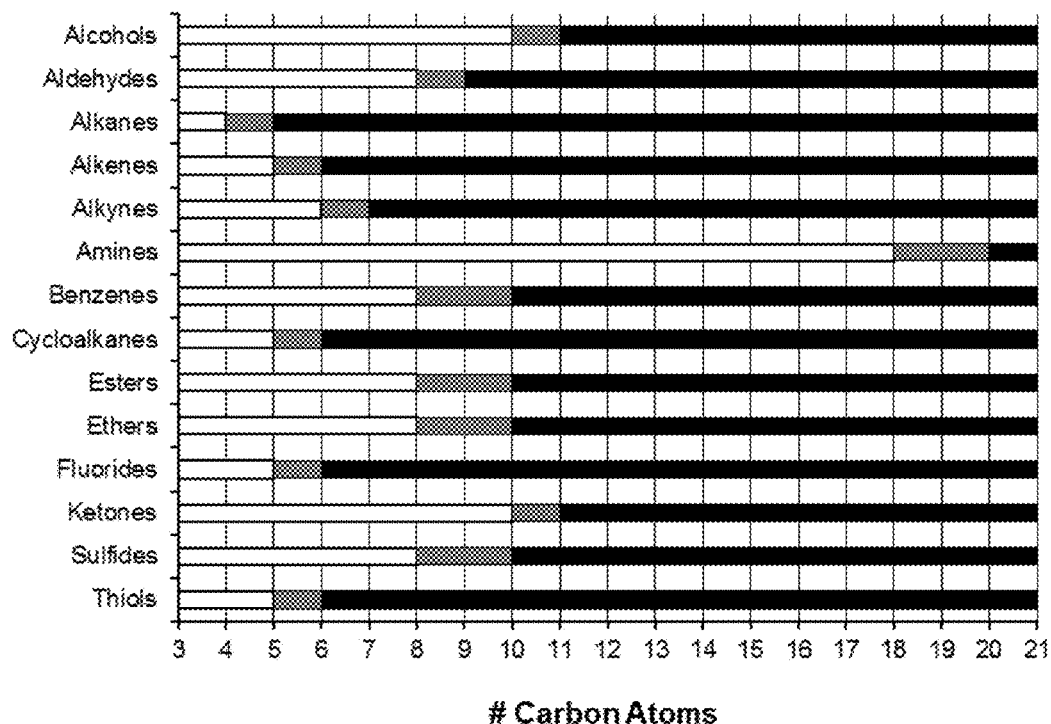
FIG. 5 illustrates a summary of receptor cut-off effects as a function of the number of drug carbon atoms. Refer to FIG. 3 for key information. No receptor cut-off pattern is evident as a function of the number of drug carbon atoms.
Figure 6:
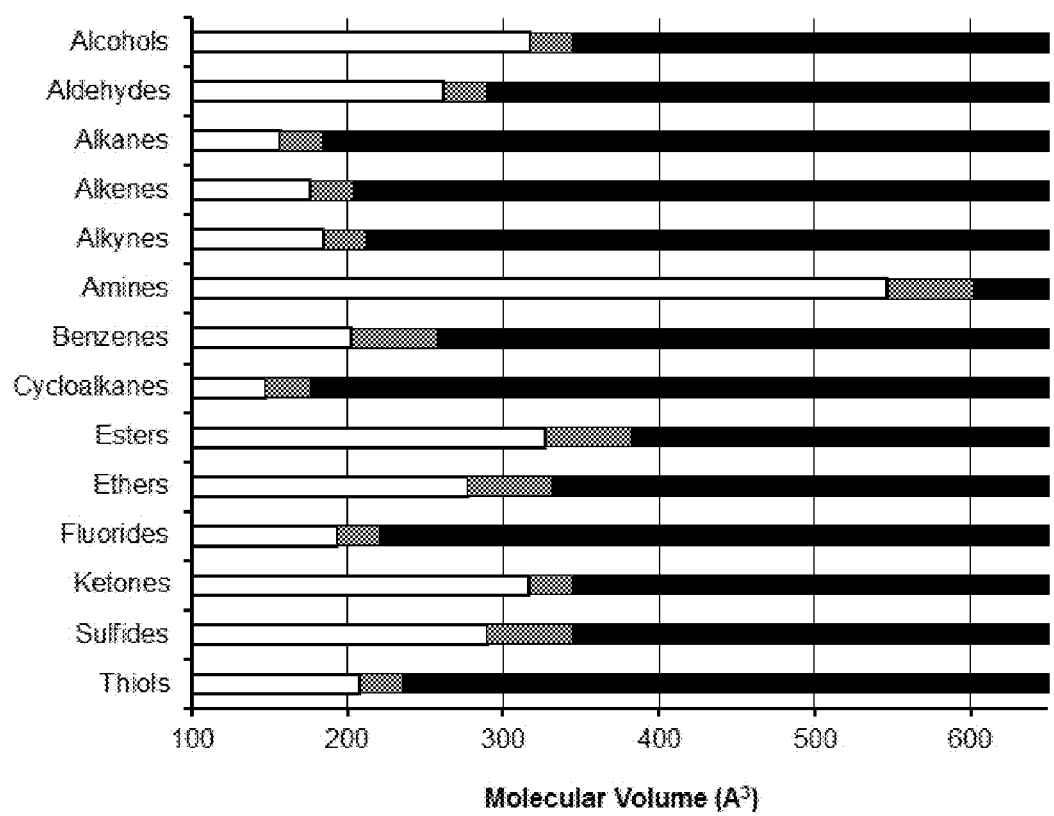
FIG. 6 illustrates a summary of receptor cut-off effects as a function of the calculated molecular volume of each drug. Refer to FIG. 3 for key information. No receptor cut-off pattern is evident as a function of molecular volume.
Figure 7:
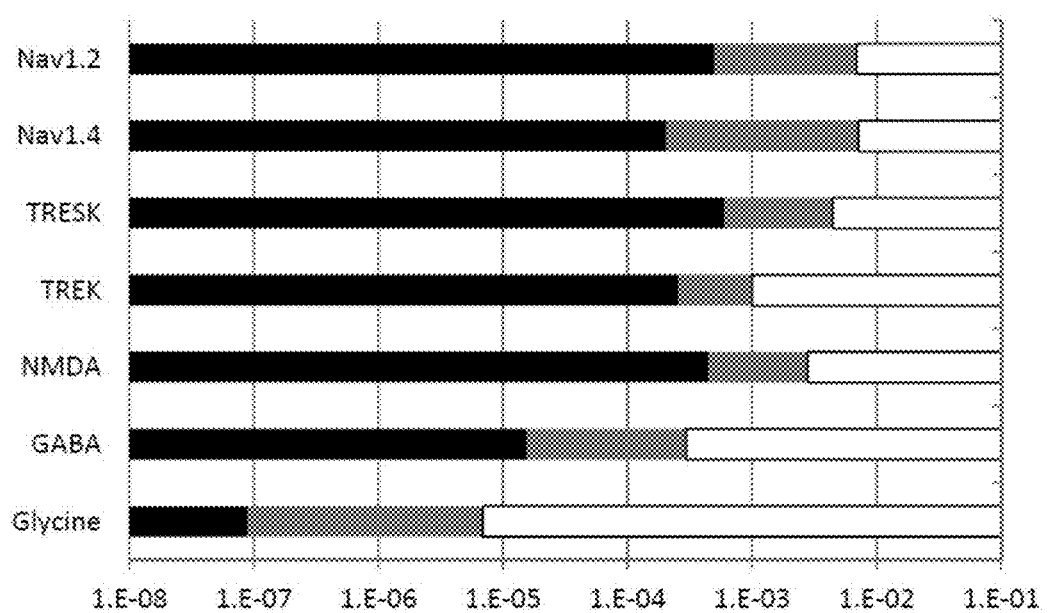
FIG. 7 illustrates a graph of ion channel and receptor modulation as a function of molar water solubility. Drugs modulate channel or receptor activity over the solubility range indicated by the white bar and do not modulate activity over the solubility range indicated by the black bar. The grey region represents the 95% confidence interval around the solubility cut-off for 3 different hydrocarbon types (1-alcohols, n-alkanes, and dialkyl ethers) for all channels and receptors except the NMDA receptor, on which a total of 13 different hydrocarbon types were studied.

Increasing hydrocarbon chain length decreases water solubility, but also increases molecular size. However, when graphed as a function of either carbon number (FIG. 5) or molecular volume (FIG. 6), the observed NMDA receptor cut-off effects show no consistent pattern. For example, the n-alkanes, 1-alkenes, and 1-alkynes show progressive lengthening of the hydrocarbon chain cut-off, presumably as a result of the increasing aqueous solubility conferred by the double and triple carbon bonds, respectively. There was also tremendous variation in molecular size of compounds exhibiting NMDA receptor cut-off. Alkanes exhibited NMDA receptor cut-off between butane and pentane, respectively 4 and 5 carbons in length, whereas the primary amines exhibited cut-off between 1-octadecanamine and 1-eicosanamine, respectively 18 and 20 carbons in length. As expected, the molecular volume of these compounds associated with NMDA receptor cut-off is also quite different, with the primary amine being over 3 times larger than the alkane.

Discussion

NMDA receptor modulation is associated with an approximate 1.1 mM water solubility cut-off (FIG. 4). In contrast, GABA$_A$ receptors potentiated all studied compounds, suggesting that either a GABA$_A$ cut-off occurs at a lower water solubility value or possibly that GABA$_A$ receptors lack such a cut-off. Increasing a single hydrocarbon length to find a receptor cut-off effect introduces confounding factors of carbon number and molecular volume that could in turn be responsible for the cut-off effect (Eger, et al., Anesth Analg (1999) 88:1395-1400; Jenkins, J Neurosci (2001) 21:RC 136; Wick, Proc Natl Acad Sci USA (1998) 95:6504-6509; Eger, Anesth Analg (2001) 92:1477-1482). An aggregate comparison of cut-off values for all functional groups as a function of carbon number (FIG. 5) or molecular volume (FIG. 6) shows no discernible pattern, suggesting that these physical properties are unlikely the primary limiting factors for drug-receptor modulation.

Nonetheless, although the correlation between cut-off and molar water solubility is very good, it is not perfect. Some variability is due simply to the lack of compounds of intermediate solubility within a functional group series. For example, pentanethiol inhibited NMDA receptors, whereas the 1-carbon longer hexanethiol did not (Table 3). This pre-cut-off thiol is nearly 3-times more soluble in water than its post-cut-off cognate; yet it is not possible to obtain a more narrowly defined cut-off delineation for 1-thiols. Even larger variability was observed with the dialkylbenzene series, to which 1 additional carbon was added to each 1- and 3-alkyl group. The solubility ratio between the NMDA antagonist 1,3-dimethylbenzene and its cut-off cognate 1,3-diethylbenzene is more than 18 (Table 3).

Variability about the molar water solubility NMDA receptor cut-off may also have arisen from the use of calculated, rather than measured, values for hydrocarbon molar water solubility. Aqueous solubility is difficult to measure accurately, particularly for poorly soluble substances. Calculated solubilities are more accurate for small uncharged compounds, but still can have an absolute error within 1 log unit (Delaney, et al., Drug Discov Today (2005) 10:289-295). However, even predicted values for nonpolar n-alkanes may show large deviations from experimental data as the hydrocarbon chain length increases (Ferguson, J Phys Chem B (2009) 113:6405-6414).

Furthermore, the molar solubility values used in the present study were calculated for pure water at 25° C. and at pH=7.0. These were not the conditions under which drug-receptor effects were studied. Ringer's oocyte perfusates contained buffers and physiologic concentrations of sodium, potassium, and chloride resulting in a 250 mOsm solution. The solubility of haloether and haloalkane anesthetic vapors vary inversely with osmolarity (Lerman, et al., *Anesthesiology* (1983) 59:554-558), as do the water-to-saline solubility ratio of benzenes, amines, and ketones (Long, et al., *Chem Rev* (1952) 51:119-169). The presence of salts could have caused overestimation of aqueous solubility for some compounds when using values calculated for pure water. Likewise, solubility is also temperature-dependent. Studies were conducted at 22° C.; solubility of gases in water should be greater than values calculated at 25° C. In contrast, most solutes used in the present study have negative enthalpy for dissolution (Abraham, et al., *J Am Chem Soc* (1982) 104:2085-2094), so solubility should be decreased at the lower ambient temperature. The reverse should occur for exothermic solutions, as predicted by the Le Chatelier principle. As for hydronium ion concentration, the solubility of most study compounds is trivially affected at pH values between 7-to-8. However, hydrocarbons containing an amine group have pKa values that are closer to physiologic pH, and the calculated aqueous solubility of 1-eicosanamine and 1-octadecanamine (Table 2) decreases by about 66% as pH increases from 7 to 8. Calculated molar water solubilities for the amines in this study were probably modestly overestimated at a physiologic pH equal to 7.4.

Despite these inaccuracies inherent in calculated rather than experimentally measured values, an association between molar water solubility and NMDA receptor modulation cut-off remains evident. Anesthetics exhibit low-affinity binding on receptors; these weak interactions are inconsistent with an induced fit binding. Rather, anesthetics likely bind to pre-existing pockets and surfaces on or within the protein (Trudell, et al., *Br J Anaesth* (2002) 89:32-40). A critical water solubility for modulation implies that critical modulation sites are either hydrophilic or amphiphilic. Hydrocarbons act as hydrogen bond donors—or in the case of electrophiles, as hydrogen bond acceptors—with amino acid residues on anesthetic-sensitive receptors, resulting in displacement of water molecules from these binding pockets and alteration of protein function (Bertaccini, et al., *Anesth Analg* (2007) 104:318-324; Abraham, et al., *J Pharm Sci* (1991) 80:719-724; Streiff, et al., *J Chem Inf Model* (2008) 48:2066-2073). These low energy anesthetic-protein interactions are postulated to be enthalpically favorable since the displaced water molecules should be better able to hydrogen bond with like molecules in the bulk solvent rather than with amino acids (Bertaccini, et al., *Anesth Analg* (2007) 104: 318-324; Streiff, et al., *J Chem Inf Model* (2008) 48:2066-2073). Halothane and isoflurane both have been shown to bind in water accessible pockets formed between α-helices in δ-subunits of the nicotinic acetylcholine receptor (Chiara, et al., *Biochemistry* (2003) 42:13457-13467), a member of the 4-transmembrane receptor superfamily that includes the $GABA_A$ receptor. Models of nicotinic acetylcholine receptors and $GABA_A$ receptors further suggest that endogenous agonist or anesthetic binding might increase water accumulation in hydrophilic pockets and increase the number and accessibility of hydrophilic sites that are important for channel gating (Willenbring, et al., *Phys Chem Chem Phys* (2010) 12:10263-10269; Williams, et al., *Biophys J* (1999) 77:2563-2574). However, molecules that are insufficiently water soluble may not be able to displace enough water molecules at enough critical sites in order to modulate channel function.

NMDA receptor modulation by inhaled anesthetics such as isoflurane, xenon, and carbon dioxide occurs—at least in part—at hydrophilic agonist binding sites (Brosnan, et al., *Anesth Analg* (2011) 112:568-573; Dickinson, et al., *Anesthesiology* (2007) 107:756-767). Yet despite evidence that hydrophilic interactions are important to hydrocarbon modulation of anesthetic-sensitive receptors, the minimum hydrocarbon hydrophilicity required to exert anesthetic-like effects is different between NMDA and $GABA_A$ receptors. As these receptors belong to different and phylogenetically distinct superfamilies, it seems likely that either the number of displaced water molecules required to effect modulation and/or the relative affinities of the hydrocarbon versus water molecule for a critical hydrophilic protein pocket and/or the number of hydrophilic sites necessary for allosteric modulation should also be different between proteins. Put another way, there is a minimum number of hydrocarbon molecules—no matter the type—that is required to interact with NMDA receptors to alter ion channel conductance, and this number is significantly greater than that necessary to alter $GABA_A$ receptor ion channel conductance. Implied is that other ion channels should exhibit hydrocarbon cut-off effects that correlate with molar water solubility, and these solubility cut-off values will likely be more similar between channels having a common phylogeny than cut-off values between distantly or unrelated proteins.

Hydrocarbons below the water solubility cut-off presumably have insufficient molecules in the aqueous phase to successfully compete with water at hydrophilic modulation or transduction sites on a receptor alter its function. Likewise, transitional compounds and nonimmobilizers predicted by the Meyer-Overton correlation to produce anesthesia either have lower than expected potency or lack anesthetic efficacy altogether. And like NMDA cut-off hydrocarbons in the present study, transitional compounds and nonimmobilizers all share a common property of low aqueous solubility (Eger E I, 2nd. Mechanisms of Inhaled Anesthetic Action In: Eger E I, 2nd, ed. The Pharmacology of Inhaled Anesthetics. I L, USA: Baxter Healthcare Corporation, 2002; 33-42). Nonimmobilizers such as 1,2-dichlorohexafluorocyclobutane fail to depress $GABA_A$-dependent pyramidal cells (Perouansky, et al., *Anesth Analg* (2005) 100:1667-1673) or NMDA-dependent CA1 neurons (Taylor, et al., *Anesth Analg* (1999) 89:1040-1045) in the hippocampus, and likely lack these effects elsewhere in the central nervous system. With decreasing water solubility, there is differential loss of receptor effects—such as occurred with NMDA receptors versus $GABA_A$ receptors in the present study. The anesthetic cut-off effect in whole animal models correlates with agent water solubility, and might be explained by the loss of one or more anesthetic-receptor contributions to central nervous system depression. Conversely, receptor molar water solubility cut-off values may be used to define those ion channels that are sine qua non for volatile anesthetic potency. Inhaled agents likely act via low affinity interactions with multiple cell receptors and ion channels to decrease neuronal excitability in the brain and spinal cord, but a loss or inadequate contribution from certain targets—perhaps $GABA_A$ or glycine receptors—as water solubility decreases may render a drug a nonimmobilizer. Additionally, agents having a water solubility below the cut-off value for some anesthetic-sensitive receptors may also produce undesirable pharmacologic properties, such as seizures following the loss of $GABA_A$ receptor modulation (Raines, *Anesthesiology* (1996) 84:663-671). In contrast, NMDA receptors can contribute to immobilizing actions of conventional volatile anesthetics, 43 but they are not as a general principle essential for inhaled anesthetic action since an agent like pentane does not modulate NMDA receptors—even at a saturated aqueous concentration (Table 3)—yet has a measurable minimum alveolar concentration (Liu, et al., *Anesth Analg* (1993) 77:12-18; Taheri, et al., *Anesth Analg* (1993) 77:7-11).

Although only water solubility was predictive of NMDA receptor cut-off, size and shape nonetheless must be able to influence this effect. Most of the hydrocarbons examined in the present study had functional groups located on the 1- or 2-carbon position. However, the ethers were all 1,1'-oxy-bisalkanes; each member of the ether consisted of symmetrical 1-carbon additions to alkyl groups on either side of the oxygen atom (Table 2). Hence this electron-rich oxygen atom allowing hydrogen bonding with water molecules or amino acid residues with strong partial positive charges lies buried in the middle of the ether. Consequently, for hydrocarbons with equivalent molar water solubilities, it may be more difficult for dialkyl ether to form hydrogen bonds in hydrophilic receptor pockets compared to a long primary amine (Table 2) that might more easily insert its nucleophilic terminus into the anesthetic-binding pocket while the long hydrophobic carbon chain remains in the lipid membrane. This may explain why ethers in this study appear to exhibit an NMDA cut-off that is slightly greater than hydrocarbons with other functional groups. Perhaps if a methyl-alkyl ether series were used instead of a dialkyl ether series, the apparent molar water solubility cut-off for this group would have been lower.

As the hydrocarbon chain lengthened within any functional group, the efficacy of $GABA_A$ receptor modulation also tended to increase. This is consistent with the Meyer-Overton prediction of increased anesthetic potency as a function of increasing hydrophobicity (Mihic, et al., *Mol Pharmacol* (1994) 46:851-857; Horishita, et al., *Anesth Analg* (2008) 107:1579-1586). However, the efficacy by which NMDA receptors were inhibited by hydrocarbons prior to the cut-off varied greatly between functional groups. Most compounds caused about 25-to-40% inhibition of NMDA receptor currents. However, the alkane n-butane almost completely inhibited NMDA receptor currents prior to cut-off, whereas the thiol 1-pentanethiol caused only 15% NMDA receptor current inhibition. Since solubility values are discontinuous within a hydrocarbon series, it is not possible to evaluate changes in modulation efficacy as solubility asymptotically approaches a cut-off within a hydrocarbon functional group series. Perhaps agents that are closer to the critical molar water solubility required for receptor modulation begin to lose potency despite increasing drug lipophilicity. If so, differences in NMDA receptor efficacy may reflect the relative difference between this theoretical critical molar water solubility and the aqueous solubility of the pre-cut-off test agent.

Finally, discrete and distinct water solubility cut-off values for anesthetic-sensitive receptors offer the possibility of a structure-activity relationship that may aid new pharmaceutical design. Anesthetics produce a number of desirable effects, such as analgesia and amnesia, and a number of side effects, such as hypotension and hypoventilation. Different pharmacodynamic properties are likely mediated by different cell receptors or channels or combinations thereof. Thus, by modifying a compound to decrease its water solubility below the NMDA receptor cut-off, absolute specificity for $GABA_A$ versus NMDA receptors may be obtained and those side-effects mediated by NMDA receptor inhibition should be reduced or eliminated. Conversely, highly insoluble agents could be modified to increase the molar water solubility above the NMDA cut-off in order to add desirable pharmacologic effects from this receptor, provided that the immobilizing versus NMDA receptor median effective concentrations are not sufficiently different as to maintain relative receptor specificity. At the same time, differential cut-off values suggest an important limit to drug design. It will probably not be possible to design an anesthetic with low-affinity receptor binding that exhibits absolute specificity for NMDA receptors while having no effect on $GABA_A$ receptors up to a saturating aqueous concentration. Only if the minimum alveolar concentration and the anesthetic potency at NMDA receptors are much greater than the anesthetic potency at $GABA_A$ receptors might relative anesthetic specificity for NMDA receptors be achieved.

Example 2

1,1,2,2,3,3,4-heptafluorocyclopentane (CAS#15290-77-4) Induces Anesthesia

All known inhalation anesthetics modulate multiple unrelated anesthetic receptors, such as transmembrane-3 (TM3) receptors, transmembrane-4 (TM4) receptors, or both TM3 and TM4 receptors. We tested a series of homologous n-alcohols, n-alkanes, n-alkenes, n-alkynes, n-aldehydes, primary amines, 1-alkylfluorides, dialkyl ethers, alkyl benzenes, esters, haloalkanes, ketones, sulfides, and thiols that differed only by 1 or 2 carbon chain lengths. We studied the effects of these drugs on NMDA receptors (a member of the TM3 superfamily) and $GABA_A$ receptors (a member of the TM4 superfamily) at saturating drug concentrations in an oocyte two-electrode voltage clamp model. For $GABA_A$ versus NMDA receptors, we found that there is no correlation between specificity and vapor pressure, carbon chain length, or molecular volume. However, there exists a water solubility-specificity cut-off value equal to about 1.1 mM with a 95% confidence interval between about 0.4 and about 2.9 mM (calculated molar solubility in water at pH=7). Compounds more soluble than this threshold value can negatively modulate NMDA receptors and positively modulate $GABA_A$ receptors. Compounds less soluble than this threshold value only positively modulate $GABA_A$ receptors. We have also identified approximate water solubility cut-off values for glycine receptors, K2P channels, and voltage-gated sodium channels.

The above-described structure activity relationship was used to identify candidate anesthetics, predict the receptor effect profile of unknown candidate anesthetics, and provide the means by which known anesthetics can be modified to change their water solubility and thus their pharmacologic effect profile. Using the above method, we have identified several candidate cyclic halogenated hydrocarbon and cyclic halogenated heterocycles that are predicted to modulate $GABA_A$ receptors, including agents that show absolute selectivity for $GABA_A$ vs. NMDA receptors (i.e., that potentiate $GABA_A$ receptors without inhibiting NMDA receptors). We identified 1,1,2,2,3,3,4-heptafluorocyclopentane (HFCP) (CAS#15290-77-4), and predicted by its solubility that it would selectively modulate $GABA_A$ but not NMDA receptors and exert a general anesthetic effect (it has until this time never been evaluated in biological systems for narcotic effects). HFCP is colorless, odorless, nonflammable, stable in soda lime, and has sufficient vapor pressure to deliver via inhalation.

HFCP caused loss of righting reflex (a surrogate measure of unconsciousness) in 4 healthy ND4 mice at 1.0±0.2 (mean±SD) percent of 1 atmosphere. This odorless agent caused no excitement or coughing during anesthetic induction. After 2 hours of anesthesia, mice were awake after about 1 minute of discontinuing HFCP administration. Histopathology of heart, lung, kidney and liver tissues collected 2 days later revealed no evidence of inflammation or toxicity. As predicted by its water solubility, 1,1,2,2,3,3,4-heptafluorocyclopentane potentiates $GABA_A$, glycine, and some inhibitory potassium channels in vitro, but has no effect on NMDA receptors up to a saturating aqueous concentration. Despite a lack of NMDA receptor effects, 1,1,2,2,3,3,4-heptafluorocyclopentane is able to produce the desired pharmacologic endpoints of unconsciousness and immobility that appears similar to desirable effects produced by conventional agents.

To our knowledge, no new inhaled anesthetics are currently under development because of an incomplete understanding of the mechanisms of action and activity-structure relationships of these agents. Inhalation anesthetics have among the lowest therapeutic indices (low safety margin) of drugs in routine clinical use; there is a need to develop newer and safer agents. We have identified a physical property (molar water solubility) that is important to determining whether an anesthetic can modulate channels or receptors that contribute to immobility and amnesia. We have applied this knowledge in order to identify a novel volatile anesthetic of clinical use (HFCP) which also lacks NMDA receptor modulation.

Example 3

1,1,2,2,3,3,4,5-octafluorocyclopentane (CAS#828-35-3) Induces Anesthesia 1,1,2,2,3,3,4,5-octafluorocyclopentane (CAS#828-35-3) caused a loss of righting reflex in 4 healthy Sprague-Dawley rats at a concentration of 3.3±0.4 (mean±SD) percent of 1 atmosphere. This agent has a faint but pleasant odor and induced anesthesia very rapidly without excitement or coughing. After discontinuing the agent, rats were awake and ambulatory in less than 1 minute. As predicted by its water solubility, 1,1,2,2,3,3,4,5-octafluorocyclopentane potentiates $GABA_A$, glycine, and some inhibitory potassium channels in vitro, but has no effect on NMDA receptors up to a saturating aqueous concentration. Despite a lack of NMDA receptor effects, 1,1,2,2,3,3,4,5-octafluorocyclopentane is able to produce the desired pharmacologic endpoints of unconsciousness and immobility that appears similar to desirable effects produced by conventional agents.

Example 4

Perfluorotetrahydropyran (CAS#355-79-3) Induces Anesthesia

Perfluorotetrahydropyran (CAS#355-79-3) caused a loss of righting reflex in mice at a concentration of 1-10%.

Example 5

2,2,3,3,4,5-hexafluorotetrahydro-5-(trifluoromethyl)-furan Induces Anesthesia 2,2,3,3,4,5-hexafluorotetrahydro-5-(trifluoromethyl)-furan (a mixture of the isomers from CAS#133618-59-4 and CAS#133618-49-2) caused a loss of righting reflex in mice at a concentration of 1-10%.

Example 6

Synthesis Schemes

General schemes for the synthesis of the halogenated anesthesia compounds described herein are known in the art. References describing the synthesis schemes generally and for the specific compounds are summarized in Table 4, below.

TABLE 4

| | Compound | Published Reference |
| --- | --- | --- |
| GENERAL SYNTHETIC FLUOROCHEMISTRY TEXTBOOKS | | Chambers, Richard D. Fluorine in Organic Chemistry. WileyBlackwell. 2004. ISBN: 978-1405107877. Iskra, Jernej. Halogenated Heterocycles: Synthesis, Application and Environment (Topics in Heterocyclic Chemistry). Springer. 2012. ISBN: 978-3642251023 Gakh, Andrei and Kirk, Kenneth L. Fluorinated Heterocycles (ACS Symposium Series). American Chemical Society. 2009. ISBN: 978-0841269538 |
| ALCOHOLS | | |
| 1351959-82-4 | Methanol, 1-fluoro-1-[2,2,2-trifluoro-1-(trifluoromethyl)ethoxy]- | |
| 14115-49-2 | 1-Butanol, 4,4,4-trifluoro-3,3-bis(trifluoromethyl)- | Mochalina, E. P.; Dyatkin, B. L.; Galakhov, I. V.; Knunyants, I. L. Doklady Akademii Nauk SSSR (1966), 169(6), 1346-9. Delyagina, N. I.; Pervova, E. Ya.; Knunyants, I. L. Izvestiya Akademii Nauk SSSR, Seriya Khimicheskaya (1972), (2), 376-80. |
| 3056-01-7 | 1-Butanol, 1,1,2,2,3,3,4,4,4-nonafluoro- | |
| 782390-93-6 | 1-Butanol, 2,2,3,4,4,4-hexafluoro-3-(trifluoromethyl)- | |
| 90999-87-4 | 1-Butanol, 3,4,4,4-tetrafluoro-3-(trifluoromethyl)- | |
| 313503-66-1 | 1-Pentanol, 1,1,4,4,5,5,5-heptafluoro- | |
| 57911-98-5 | 1-Pentanol, 1,1,2,2,3,3,4,4,5,5,5-undecafluoro- | |

TABLE 4-continued

| | Compound | Published Reference |
|---|---|---|
| DIETHERS | | |
| 362631-92-3 | Ethane, 1,1,2-trifluoro-1,2-bis(trifluoromethoxy)- | |
| 115395-39-6 | Ethane, 1,1,1,2-tetrafluoro-2,2-bis(trifluoromethoxy)- | Venturini, Francesco; Metrangolo, Pierangelo; Resnati, Giuseppe; Navarrini, Walter; Tortelli, Vito. Chimica Oggi (2008), 26(4), 36-38. Navarrini, Walter; Venturini, Francesco; Sansotera, Maurizio; Ursini, Maurizio; Metrangolo, Pierangelo; Resnati, Giuseppe; Galimberti, Marco; Barchiesi, Emma; Dardani, Patrizia. Journal of Fluorine Chemistry (2008), 129(8), 680-685.<br>Adcock, James L.; Robin, Mark L.; Zuberi, Sharique. Journal of Fluorine Chemistry (1987), 37(3), 327-36.<br>Cantini, Marco; Metrangolo, Pierangelo; Navarrini, Walter; Resnati, Giuseppe; Venturini, Francesco. Ital. Appl. (2007), IT 2007MI1481 A1 20071023.<br>Marraccini, Antonio; Pasquale, Antonio; Fiorani, Tiziana; Navarrini, Walter. Eur. Pat. Appl. (1990), EP 404076 A1 19901227. |
| 40891-98-3 | Ethane, 1-(difluoromethoxy)-1,1,2,2-tetrafluoro-2-(trifluoromethoxy)- | Adcock, J. L.; Lagow, R. J. Journal of Organic Chemistry (1973), 38(20), 3617-18. |
| 378-11-0 | Ethane, 1,1,2,2-tetrafluoro-1,2-bis(trifluoromethoxy)- | |
| 362631-95-6 | Ethane, 1,2-difluoro-1,2-bis(trifluoromethoxy)- | |
| 1683-90-5 | Ethane, 1,2-bis(trifluoromethoxy)- | Aldrich, P. E.; Sheppard, William A. Journal of Organic Chemistry (1964), 29(1), 11-15. |
| 870715-97-2 | Propane, 1,1,3,3-tetrafluoro-1,3-bis(trifluoromethoxy)- | Weis, Derick C.; Faulon, Jean-Loup; LeBorne, Richard C.; Visco, Donald P., Jr. Industrial & Engineering Chemistry Research (2005), 44(23), 8883-8891. |
| 156833-18-0 | Propane, 2,2-difluoro-1,3-bis(trifluoromethoxy)- | Arimura, Takashi; Kurosawa, Shigeru; Sekiya, Akira. Journal of Chemical Research, Synopses (1994), (5), 202-3. |
| 133640-19-4 | Propane, 1,1,1,3,3-pentafluoro-3-methoxy-2-(trifluoromethoxy)- | |
| 124992-92-3 | Propane, 1,1,1,3,3,3-hexafluoro-2-(fluoromethoxymethoxy)- | Du, Xue Mei; Fan, Hong; Goodman, Joshua L.; Kesselmayer, Mark A.; Krogh-Jespersen, Karsten; LaVilla, Joseph A.; Moss, Robert A.; Shen, Shilan; Sheridan, Robert S. Journal of the American Chemical Society (1990), 112(5), 1920-6. |
| 104159-55-9 | Propane, 1,1,1,2,3,3-hexafluoro-3-methoxy-2-(trifluoromethoxy)- | Galimberti, Marco; Fontana, Giovanni; Resnati, Giuseppe; Navarrini, Walter. Journal of Fluorine Chemistry (2005), 126(11-12), 1578-1586.<br><br>Navarrini, Walter; Galimberti, Marco; Fontana, Giovanni. Eur. Pat. Appl. (2004), EP 1462434 A1 20040929. |
| DIOXANES | | |
| 362631-99-0 | 1,4-Dioxane, 2,2,3,3,5,6-hexafluoro- | |
| 135871-00-0 | 1,4-Dioxane, 2,3-dichloro-2,3,5,5,6,6-hexafluoro- | Krespan, Carl George; Resnick, Paul Raphael. PCT Int. Appl. (1991), WO 9104251 A2 19910404. |
| 56625-45-7 | 1,4-Dioxane, 2,3-dichloro-2,3,5,5,6,6-hexafluoro-, trans- (9CI) | Krespan, Carl G.; Dixon, David A. Journal of Organic Chemistry (1991), 56(12), 3915-23.<br><br>Coe, P. L.; Dodman, P.; Tatlow, J. C. Journal of Fluorine Chemistry (1975), 6(2), 115-28. |
| 56625-44-6 | 1,4-Dioxane, 2,3-dichloro-2,3,5,5,6,6-hexafluoro-, cis- (9CI) | Krespan, Carl G.; Dixon, David A. Journal of Organic Chemistry (1991), 56(12), 3915-23.<br><br>Coe, P. L.; Dodman, P.; Tatlow, J. C. Journal of Fluorine Chemistry (1975), 6(2), 115-28. |
| 56269-26-2 | 1,4-Dioxane, 2,2,3,5,6,6-hexafluoro- | Burdon, James; Coe, Paul L.; Parsons, Ian W.; Tatlow, John C. U.S. (1975), US 3883559 A 19750513. |
| 56269-25-1 | 1,4-Dioxane, 2,2,3,5,5,6-hexafluoro- | Burdon, James; Coe, Paul L.; Parsons, Ian W.; Tatlow, John C. U.S. (1975), US 3883559 A 19750513. |
| 34206-83-2 | 1,4-Dioxane, 2,2,3,3,5,6-hexafluoro-, trans- (9CI) | Burdon, James; Coe, Paul L.; Parsons, Ian W.; Tatlow, John C. U.S. (1975), US 3883559 A 19750513.<br>Coe, P. L.; Dodman, P.; Tatlow, J. C. Journal of Fluorine Chemistry (1975), 6(2), 115-28.<br>Burdon, J.; Parsons, I. W. Tetrahedron (1971), 27(19), 4533-51. |
| 34181-52-7 | 1,4-Dioxane, 2,2,3,5,5,6-hexafluoro-, cis- (9CI) | Burdon, James; Coe, Paul L; Parsons, Ian W.; Tatlow, John C. U.S. (1975), US 3883559 A 19750513.<br>Coe, P. L.; Dodman, P.; Tatlow, J. C. Journal of Fluorine Chemistry (1975), 6(2), 115-28.<br>Burdon, J.; Parsons, I. W. Tetrahedron (1971), 27(19), 4533-51. |

TABLE 4-continued

| Compound | | Published Reference |
|---|---|---|
| 34181-51-6 | p-Dioxane, 2,2,3,5,5,6-hexafluoro-, trans- (8Cl) | Burdon, James; Coe, Paul L.; Parsons, Ian W.; Tatlow, John C. U.S. (1975), US 3883559 A 19750513.<br>Burdon, J.; Parsons, I. W. Tetrahedron (1971), 27(19), 4533-51. |
| 34181-50-5 | 1,4-Dioxane, 2,2,3,5,6,6-hexafluoro-, cis- (9Cl) | Burdon, James; Coe, Paul L.; Parsons, Ian W.; Tatlow, John C. U.S. (1975), US 3883559 A 19750513.<br>Coe, P. L; Dodman, P.; Tatlow, J. C. Journal of Fluorine Chemistry (1975), 6(2), 115-28.<br>Burdon, J.; Parsons, I. W. Tetrahedron (1971), 27(19), 4533-51. |
| 34181-49-2 | p-Dioxane, 2,2,3,5,6,6-hexafluoro-, trans- (8Cl) | Burdon, J.; Parsons, I. W. Tetrahedron (1971), 27(19), 4533-51. |
| 34181-48-1 | 1,4-Dioxane, 2,2,3,3,5,6-hexafluoro-, (5R,6S)-rel- | Coe, P. L; Dodman, P.; Tatlow, J. C. Journal of Fluorine Chemistry (1975), 6(2), 115-28.<br>Burdon, J.; Parsons, I. W. Tetrahedron (1971), 27(19), 4533-51. |
| 34118-18-8 | 1,4-Dioxane, 2,2,3,3,5,5,6-heptafluoro- | Adcock, James L. Journal of Fluorine Chemistry (1980), 16(3), 297-300.<br>Dodman, P.; Tatlow, J. C. Journal of Fluorine Chemistry (1976), 8(3), 263-74.<br>Burdon, James; Coe, Paul L.; Parsons, Ian W.; Tatlow, John C. U.S. (1975), US 3883559 A 19750513.<br>Coe, P. L.; Dodman, P.; Tatlow, J. C. Journal of Fluorine Chemistry (1975), 6(2), 115-28.<br>Burdon, J.; Parsons, I. W. Tetrahedron (1971), 27(19), 4533-51. |
| 32981-22-9 | 1,4-Dioxane, 2,2,3,3,5,5,6,6-octafluoro- | Meinert, H.; Fackler, R.; Mader, J.; Reuter P.; Roehlke, W. Journal of Fluorine Chemistry (1992), 59(3), 351-65.<br>Krespan, Carl G.; Dixon, David A. Journal of Organic Chemistry (1991), 56(12), 3915-23.<br>Adcock, James L. Journal of Fluorine Chemistry (1980), 16(3), 297-300.<br>Berenblit, V. V.; Dolnakov, Yu. P.; Davidov, G. A.; Sokolov, S. V. Zhurnal Prikladnoi Khimii (Sankt-Peterburg, Russian Federation) (1980), 53(4), 858-61.<br>Lagow, Richard J.; Adcock, James L.; Maraschin, Norma J. U.S. (1978), US 4113435 A 19780912.<br>Berenblit, V. V.; Dolnakov, Yu. P.; Davydov, G. A.; Grachev, V. I.; Sokolov, S. V. Zhurnal Prikladnoi Khimii (Sankt-Peterburg, Russian Federation) (1975), 48(10), 2206-10.<br>Adcock, J. L.; Beh, R. A.; Lagow, R. J. Journal of Organic Chemistry (1975), 40(22), 3271-5.<br>Abe, Takashi; Nagase, Shunji; Baba, Hajime. Jpn. Tokkyo Koho (1974), JP 49027588 B 19740718.<br>Berenblit, V. V.; Dolnakov, Yu. P.; Sass, V. P.; Senyushov, L. N.; Sokolov, S. V. Zhurnal Organicheskoi Khimii (1974), 10(10), 2031-5.<br>Adcock, J. L.; Lagow, R. J. Journal of the American Chemical Society (1974), 96(24), 7588.<br>Abe. Takashi; Nagase, Shunji; Baba, Hajime. Bulletin of the Chemical Society of Japan (1973), 46(8), 2524-7.<br>Sianesi, Dario; Fontanelli, Renzo; Grazioli, Alberto. Ger. Offen. (1972), DE 2111696 A 19720127. |
| DIOXOLANES | | |
| 344303-08-8 | 1,3-Dioxolane, 2,4,4,5-tetrafluoro-5-(trifluoromethyl)- | |
| 344303-05-5 | 1,3-Dioxolane, 2-chloro-4,4,5-trifluoro-5-(trifluoromethyl)- | |
| 269716-57-6 | 1,3-Dioxolane, 4,4,5,5-tetrafluoro-2-(trifluoromethyl)- | Kawa, Hajim; Takubo, Seiji. Jpn. Kokai Tokkyo Koho (2000), JP 2000143657 A 20000526. |
| 238754-29-5 | 1,3-Dioxolane, 4-chloro-2,2,4-trifluoro-5-(trifluoromethyl)- | Russo, Antonio; Navarrini, Walter. Eur. Pat. Appl. (1999), EP 937720 A1 19990825.<br>Russo, Antonio; Navarrini, Walter. Journal of Fluorine Chemistry (2004), 125(1), 73-78. |
| 162970-78-7 | 1,3-Dioxolane, 4,5-dichloro-2,2,4,5-tetrafluoro-, trans- (9Cl) | Navarrini, W.; Bragante, L; Fontana, S.; Tortelli, V.; Zedda, A. Journal of Fluorine Chemistry (1995), 71(1), 111-17. |
| 162970-76-5 | 1,3-Dioxolane, 4,5-dichloro-2,2,4,5-tetrafluoro-, cis- (9Cl) | Navarrini, W.; Bragante, L.; Fontana, S.; Tortelli, V.; Zedda, A. Journal of Fluorine Chemistry (1995), 71(1), 111-17. |
| 139139-68-7 | 1,3-Dioxolane, 4-chloro-2,2,4,5,5-pentafluoro- | Navarrini, W.; Bragante, L.; Fontana, S.; Tortelli, V.; Zedda, A. Journal of Fluorine Chemistry (1995), 71(1), 111-17. |
| 87075-00-1 | 1,3-Dioxolane, 4,5-dichloro-2,2,4,5-tetrafluoro- | Navarrini, Walter; Bragante, Letanzio. Eur. Pat. Appl. (1992), EP 499158 A1 19920819.<br>Navarrini, Walter; Fontana, Simonetta. Eur. Pat. Appl. (1992), EP 499157 A1 19920819.<br>Navarrini, Walter; Tortelli, Vito; Zedda, Alessandro. Eur. Pat. Appl. (1995), EP 683181 A1 19951122. |

TABLE 4-continued

| Compound | | Published Reference |
|---|---|---|
| 85036-66-4 | 1,3-Dioxolane, 2,4,4,5-tetrafluoro-5-(trifluoromethyl)-, trans- (9CI) | Muffler, Herbert; Siegemund, Guenter; Schwertfeger, Werner. Journal of Fluorine Chemistry (1982), 21(2), 107-32. |
| 85036-65-3 | 1,3-Dioxolane, 2,4,4,5-tetrafluoro-5-(trifluoromethyl)-, cis- (9CI) | Muffler, Herbert; Siegemund, Guenter; Schwertfeger, Werner. Journal of Fluorine Chemistry (1982), 21(2), 107-32. |
| 85036-60-8 | 1,3-Dioxolane, 2-chloro-4,4,5-trifluoro-5-(trifluoromethyl)-, trans- (9CI) | Muffler, Herbert; Siegemund, Guenter; Schwertfeger, Werner. Journal of Fluorine Chemistry (1982), 21 (2), 107-32. |
| 85036-57-3 | 1,3-Dioxolane, 2-chloro-4,4,5-trifluoro-5-(trifluoromethyl)-, cis- (9CI) | Muffler, Herbert; Siegemund, Guenter; Schwertfeger, Werner. Journal of Fluorine Chemistry (1982), 21(2), 107-32. |
| 85036-55-1 | 1,3-Dioxolane, 2,2-dichloro-4,4,5,5-tetrafluoro- | Muffler, Herbert; Siegemund, Guenter; Schwertfeger, Werner. Journal of Fluorine Chemistry (1982), 21(2), 107-32. |
| 76492-99-4 | 1,3-Dioxolane, 4,4,5-trifluoro-5-(trifluoromethyl)- | Siegemund, Guenter; Muffler, Herbert. Ger. Offen. (1980), DE 2906447 A1 19800904.<br>Muffler, Herbert; Siegemund, Guenter; Schwertfeger, Werner. Journal of Fluorine Chemistry (1982), 21(2), 107-32. |
| 64499-86-1 | 1,3-Dioxolane, 4,4-difluoro-2,2-bis(trifluoromethyl)- | |
| 64499-85-0 | 1,3-Dioxolane, 4,5-difluoro-2,2-bis(trifluoremethyl)-, cis- (9CI) | |
| 64499-66-7 | 1,3-Dioxolane, 4,5-difluoro-2,2-bis(trifluoromethyl)-, trans- (9CI) | |
| 64499-65-6 | 1,3-Dioxolane, 4,4,5-trifluoro-2,2-bis(trifluoromethyl)- | Anton, Douglas Robert; Farnham, William Brown; Hung, Ming Hong; Mckinney, Ronald James; Resnick, Paul Raphael. PCT Int. Appl. (1991), WO 9109025 A2 19910627. |
| 55135-01-8 | 1,3-Dioxolane, 2,4,4,5,5-pentafluoro-2-(trifluoromethyl)- | Berenblit, V. V.; Dolnakov, Yu. P.; Sass, V. P.; Senyushov, L. N.; Sokolov, S. V. Zhurnal Organicheskoi Khimii (1974), 10(10), 2031-5.<br><br>Berenblit, V. V.; Dolnakov, Yu. P.; Davydov, G. A.; Grachev, V. I.; Sokolov, S. V. Zhurnal Prikladnoi Khimii (Sankt-Peterburg, Russian Federation) (1975), 48(10), 2206-10. |
| 21297-65-4 | 1,3-Dioxolane, 2,2,4,4,5,5-hexafluoro- | Prager, Julianne H. Journal of Organic Chemistry (1966), 31(2), 392-4.<br><br>Throckmorton, James R. Journal of Organic Chemistry (1969), 34(11), 3438-40.<br>Sianesi, Dario; Fontanelli, Renzo; Grazioli, Alberto. Ger. Offen. (1972), DE 2111696 A 19720127.<br>Berenblit, V. V.; Dolnakov, Yu. P.; Davydov, G. A; Grachev, V. I.; Sokolov, S. V. Zhurnal Prikladnoi Khimii (Sankt-Peterburg, Russian Federation) (1975), 48(10), 2206-10.<br>Berenblit, V. V.; Dolnakov, Yu. P.; Sass, V. P.; Senyushov, L. N.; Sokolov, S. V. Zhurnal Organicheskoi Khimii (1974), 10(10), 2031-5.<br>Navarrini, Walter; Fontana, Simonetta; Montanari, Vittorio. Eur. Pat. Appl. (1991), EP 460948 A2 19911211.<br>Navarrini, W.; Bragante, L.; Fontana, S.; Tortelli, V.; Zedda, A. Journal of Fluorine Chemistry (1995), 71(1), 111-17. |
| 19701-22-5 | 1,3-Dioxolane, 2,2,4,4,5-pentafluoro-5-(trifluoromethyl)- | Navarrini, Walter; Fontana, Simonetta; Montanari, Vittorio. Eur. Pat. Appl. (1991), EP 460948 A2 19911211.<br><br>Navarrini, W.; Bragante, L.; Fontana, S.; Tortelli, V.; Zedda, A. Journal of Fluorine Chemistry (1995), 71(1), 111-17. |
| CYCLOPENTANES | | |
| 362014-70-8 | Cyclopentane, 5-chloro-1,1,2,2,3,3,4,4-octafluoro- | Imura, Hideaki; Takada, Naokado; Komata, Takeo. Jpn. Kokai Tokkyo Koho (2001), JP 2001261594 A 20010926. |
| 773-17-1 | Cyclopentane, 1,1,2,2,3,4,4,5-octafluoro- | Heitzman, R. J.; Patrick, C. R.; Stephens, R.; Tatlow, J. C. Journal of the Chemical Society (1963), 281-9. |
| 828-35-3 | Cyclopentane, 1,1,2,2,3,3,4,5-octafluoro- | Sekiya, Akira; Yamada, Toshiro; Watanabe, Kazunori. PCT Int. Appl. (1996), WO 9600707 A1 19960111.<br>Sekya, Akira; Yamada, Toshiro; Watanabe, Kazunori. Jpn. Kokai Tokkyo Koho (1996), JP 08143487 A 19960604. |
| 3002-03-7 | Cyclopentane, 1,1,2,3,3,4,5-heptafluoro- | |
| 149600-73-7 | Cyclopentane, 1,1,2,2,3,3,4,4-octafluoro- | Rao, Velliyur Nott Mallikarjuna; Weigert, Frank Julian; Krespan, Carl George. PCT Int. Appl. (1993), WO 9305002 A2 19930318. |
| 1765-23-7 | Cyclopentane, 1,1,2,2,3,4,5-heptafluoro- | Heitzman, R. J.; Patrick, C. R.; Stephens, R.; Tatlow, J. C. Journal of the Chemical Society (1963), 281-9.<br>Burdon, J.; Hodgins, T. M.; Stephens, R.; Tatlow, J. C. Journal of the Chemical Society (1965), (April), 2382-91.<br>Yamada, Toshiro; Sugimoto, Tatsuya. Jpn. Kokai Tokkyo Koho (1999), JP 11292807 A 19991026. |

TABLE 4-continued

| Compound | | Published Reference |
|---|---|---|
| 699-38-7 | Cyclopentane, 1,1,2,3,4,5-hexafluoro- | |
| 15290-77-4 | Cyclopentane, 1,1,2,2,3,3,4-heptafluoro- | Otsuki, Noriyasu. Petrotech (Tokyo, Japan) (2005), 28(7), 489-493.<br><br>Takada, Naokado; Hirotsu, Miki; Komata, Takeo. Jpn. Kokai Tokkyo Koho (2002), JP 2002241325 A 20020828.<br>Suzuki, Takefumi; Kim, Yoon Nam; Yuasa, Hiroko; Yamada, Toshiro. Jpn. Kokai Tokkyo Koho (2001), JP 2001247494 A 20010911.<br>Sekiya, Akira; Ko, Masataka; Tamura, Masanori; Yamada, Toshiro. Jpn. Kokai Tokkyo Koho (2001), JP 2001240567 A 20010904.<br>Kim, Yoon Nam; Yuasa, Hiroko; Suzuki, Takefumi; Yamada, Toshiro. Jpn. Kokai Tokkyo Koho (2001), JP 2001240569 A 20010904.<br>Sakyu, Fuyuhiko; Takada, Naokado; Komata, Takeo; Kim, Yoon Nam; Yamada, Toshiro; Sugimoto, Tatsuya. Jpn. Kokai Tokkyo Koho (2000), JP 2000247912 A 20000912.<br>Saku, Fuyuhiko; Takada, Naokado; Inomura, Hideaki; Komata, Takeo. Jpn. Kokai Tokkyo Koho (2000), JP 2000226346 A 20000815.<br>Yamada, Toshiro; Sugimoto, Tatsuya; Sugawara, Mitsuru. PCT Int. Appl. (1999), WO 9950209 A1 19991007.<br>Yamada, Toshiro; Uruma, Takashi; Sugimoto, Tatsuya. PCT Int. Appl. (1999), WO 9933771 A1 19990708.<br>Sekiya, Akira; Yamada, Toshirou; Uruma, Takashi; Sugimoto, Tatsuya. PCT Int. Appl. (1998), WO 9851650 A1 19981119.<br>Banks, Ronald E.; Barlow, Michael G.; Haszeldine, Robert N.; Lappin, M.; Matthews, V.; Tucker, N. I. Journal of the Chemical Society [Section] C: Organic (1968), (5), 548-50. |
| 199989-36-1 | Cyclopentane, 1,1,2,2,3,4-hexafluoro- | |
| 123768-18-3 | Cyclopentane, 1,1,2,2,3,3-hexafluoro- | Stepanov, A. A.; Delyagina, N. I.; Cherstkov, V. F. Russian Journal of Organic Chemistry (2010), 46(9), 1290-1295.<br>Saku, Fuyuhiko; Takada, Naokado; Inomura, Hideaki; Komata, Takeo. Jpn. Kokai Tokkyo Koho (2000), JP 2000226346 A 20000815.<br>Sekiya, Akira; Yamada, Toshirou; Uruma, Takashi; Sugimoto, Tatsuya. PCT Int. Appl. (1998), WO 9851650 A1 19981119.<br>Sekiya, Akira; Yamada, Toshiro; Watanabe, Kazunori. Jpn. Kokai Tokkyo Koho (1996), JP 08143487 A 19960604.<br>Yamada, Toshiro; Mitsuda, Yasuhiro. PCT Int. Appl. (1994), WO 9407829 A1 19940414.<br>Anton, Douglas Robert. PCT Int. Appl. (1991), WO 9113846 A1 19910919.<br>Bielefeldt, Dietmar; Braden, Rudolf; Negele, Michael; Ziemann, Heinz. Eur. Pat. Appl. (1991), EP 442087 A1 19910821.<br>Bielefeldt, Dietmar; Marhold, Albrecht; Negele, Michael. Ger. Offen. (1989), DE 3735467 A1 19890503. |
| 1259529-57-1 | Cyclopentane, 1,1,2,2,3-pentafluoro- | |
| CYCLOHEXANES | | |
| 830-15-9 | Cyclohexane, 1,1,2,2,3,3,4,4-octafluoro- | Evans, D. E. M.; Feast, W. J.; Stephens, R.; Tatlow, J. C. Journal of the Chemical Society (1963), (October), 4828-34. |
| FURANS | | |
| 634191-25-6 | Furan, 2,3,4,4-tetrafluorotetrahydro-2,3-bis(trifluoromethyl)- | |
| 377-83-3 | Furan, 2,2,3,3,4,4,5-heptafluorotetrahydro-5-(trifluoromethyl)- | Chepik, S. D.; Cherstkov, V. F.; Mysov, E. I.; Aerov, A F.; Galakhov, M. V.; Sterlin, S. R.; German, L. S. Izvestiya Akademii Nauk SSSR, Seriya Khimicheskaya (1991), (11), 2611-18.<br>Abe, Takashi; Nagase, Shunji. Journal of Fluorine Chemistry (1979), 13(6), 519-30.<br>Abe, Takashi; Nagase, Shunji. Jpn. Kokai Tokkyo Koho (1978), JP 53025552 A 19780309.<br>Abe, Takashi; Nagase, Toshiharu; Baba, Hajime. Jpn. Tokkyo Koho (1976), JP 51045594 B 19761204.<br>Abe, Takashi; Nagase, Shunji; Baba, Hajime. Jpn. Kokai Tokkyo Koho (1976), JP 51082257 A 19760719.<br>Abe, Takashi; Nagase, Shunji; Baba, Hajime. Jpn. Kokai Tokkyo Koho (1975), JP 50106955 A 19750822.<br>Abe, Takashi; Nagase, Toshiharu; Baba, Hajime. Jpn. Tokkyo Koho (1973), JP 48012742 B 19730423. |

TABLE 4-continued

| Compound | | Published Reference |
|---|---|---|
| 374-53-8 | Furan, 2,2,3,3,4,5,5-heptafluorotetrahydro-4-(trifluoromethyl)- | Jpn. Kokai Tokkyo Koho (1981), JP 56142877 A 19811107. |
| | | Abe, Takashi; Nagase, Shunji. Journal of Fluorine Chemistry (1979), 13(6), 519-30. |
| | | Abe, Takashi; Nagase, Shunji. Jpn. Kokai Tokkyo Koho (1978), JP 53124259 A 19781030. |
| | | Abe, Takashi; Nagase, Shunji. Jpn. Kokai Tokkyo Koho (1978), JP 53025552 A 19780309. |
| | | Abe, Takashi; Nagase, Toshiharu; Baba, Hajime. Jpn. Tokkyo Koho (1976), JP 51045594 B 19761204. |
| | | Abe, Takashi; Nagase, Shunji; Baba, Hajime. Jpn. Kokai Tokkyo Koho (1976), JP 51082257 A 19760719. |
| 133618-52-7 | Furan, 2,2,3,4,5-pentafluorotetrahydro-5-(trifluoromethyl)-, (2a,3a,4β)- | |
| 133618-53-8 | Furan, 2,2,3,4,5-pentafluorotetrahydro-5-(trifluoromethyl)-, (2α,3β,4α)- (9CI) | Burdon, James; Coe, Paul L; Smith, J. Anthony; Tatlow, John Colin. Journal of Fluorine Chemistry (1991), 51(2), 179-96. |
| 133618-52-7 | Furan, 2,2,3,4,5-pentafluorotetrahydro-5-(trifluoromethyl)-, (2α,3α,4β)- (9CI) | Burdon, James; Coe, Paul L.; Smith, J. Anthony; Tatlow, John Colin. Journal of Fluorine Chemistry (1991), 51(2), 179-96. |
| 61340-70-3 | Furan, 2,2,3,3,5,5-hexafluorotetrahydro-4-(trifluoromethyl)- | Abe, Takashi; Nagase, Shunji; Baba, Hajime. Bulletin of the Chemical Society of Japan (1976), 49(7), 1888-92. |
| 634191-26-7 | Furan, 2,3-difluorotetrahydro-2,3-bis(trifluoromethyl)- | |
| 1026470-51-8 | Furan, 2-chloro-2,3,3,4,4,5,5-heptafluorotetrahydro- | |
| 179017-83-5 | Furan, 2,2,3,3,4,4,5-heptafluorotetrahydro-5-methyl- | |
| 133618-59-4 | Furan, 2,2,3,3,4,5-hexafluorotetrahydro-5-(trifluoromethyl)-, trans- (9CI) | Burdon, James; Coe, Paul L.; Smith, J. Anthony; Tatlow, John Colin. Journal of Fluorine Chemistry (1991), 51(2), 179-96. |
| 133618-49-2 | Furan, 2,2,3,3,4,5-hexafluorotetrahydro-5-(trifluoromethyl)-, cis- (9CI) | Burdon, James; Coe, Paul L.; Smith, J. Anthony; Tatlow, John Colin. Journal of Fluorine Chemistry (1991), 51(2), 179-96. |
| PYRANS | | |
| 71546-79-7 | 2H-Pyran, 2,2,3,3,4,5,5,6,6-nonafluorotetrahydro-4- | Abe, Takashi; Nagase, Shunji. Journal of Fluorine Chemistry (1979), 13(6), 519-30. |
| 356-47-8 | 2H-Pyran, 2,2,3,3,4,4,5,5,6-nonafluorotetrahydro-6-(trifluoromethyl)- | Abe, Takashi; Tamura, Masanori; Sekiya, Akira. Journal of Fluorine Chemistry (2005), 126(3), 325-332. |
| | | Jpn. Kokai Tokkyo Koho (1980), JP 55051084 A 19800414. |
| | | Abe, Takashi; Nagase, Shunji. Journal of Fluorine Chemistry (1979), 13(6), 519-30. |
| | | Abe, Takashi; Kodaira, Kazuo; Baba, Hajime; Nagase, Shunji. Journal of Fluorine Chemistry (1978), 12(1), 1-25. |
| | | No Inventor data available. (1961), GB 862538 19610315. |
| | | Sander, Manfred; Helfrich, Frledrich; Blochl, Walter. (1959), DE 1069639 19591126. |
| | | No Inventor data available. (1954), GB 718318 19541110. |
| 61340-74-7 | 2H-Pyran, 2,2,3,3,4,4,5,6,6-nonafluorotetrahydro-5-(trifluoromethyl)- | Abe, Takashi; Nagase, Shunji. Journal of Fluorine Chemistry (1979), 13(6), 519-30. |
| | | Abe, Takashi; Nagase, Shunji; Baba, Hajime. Bulletin of the Chemical Society of Japan (1976), 49(7), 1888-92. |
| | | Abe, Takashi; Kodaira, Kazuo; Baba, Hajime; Nagase, Shunji. Journal of Fluorine Chemistry (1978), 12(1), 1-25. |
| 657-48-7 | 2H-Pyran, 2,2,6,6-tetrafluorotetrahydro-4-(trifluoromethyl)- | Wang, Chia-Lin J. Organic Reactions (Hoboken, NJ, United States) (1985), 34, No pp. given. |
| | | Dmowski, Wojciech; Kolinski, Ryszard A. Polish Journal of Chemistry (1978), 52(1), 71-85. |
| | | Hasek, W. R.; Smith, W. C.; Engelhardt, V. A. Journal of the American Chemical Society (1960), 82, 543-51. |

TABLE 4-continued

| Compound | | Published Reference |
|---|---|---|
| 874634-55-6 | 2H-Pyran, 2,2,3,3,4,4,5,5,6-nonafluorotetrahydro-6-methyl- | Abe, Takashi; Tamura, Masanori; Sekiya, Akira. Journal of Fluorine Chemistry (2005), 126(3), 325-332. |
| 355-79-3 | Perfluorotetrahydropyran | Wang, Chia-Lin J. Organic Reactions (Hoboken, NJ, United States) (1985), 34, No pp. given.<br>Abe, Takashi; Tamura, Masanori; Sekiya, Akira. Journal of Fluorine Chemistry (2005), 126(3), 325-332.<br>Moldavsky, Dmitrii D.; Furin, Georgii G. Journal of Fluorine Chemistry (1998), 87(1), 111-121.<br>Nishimura, Masakatsu; Shibuya, Masashi; Okada, Naoya; Tokunaga, Shinji. Jpn. Kokai Tokkyo Koho (1989), JP 01249728 A 19891005.<br>Nishimura, Masakatsu; Okada, Naoya; Murata, Yasuo; Hirai, Yasuhiko. Eur. Pat. Appl. (1988), EP 271272 A2 19880615.<br>Abe, Takashi; Nagase, Shunji. Journal of Fluorine Chemistry (1979), 13(6), 519-30.<br>De Pasquale, Ralph J. Journal of Organic Chemistry (1973), 38(17), 3025-30.<br>Abe, Takashi; Nagase, Toshiharu; Baba, Hajime. Jpn. Tokkyo Koho (1973), JP 48012742 B 19730423.<br>Henne, Albert L; Richter, Sidney B. Journal of the American Chemical Society (1952), 74, 5420-2.<br>Kauck, Edward A.; Simons, Joseph H. (1952), US 2594272 19520429. |
| 362631-93-4 | 2H-Pyran, 2,2,3,3,4,5,5,6-octafluorotetrahydro-, (4R,6S)-rel- | |
| 65601-69-6 | 2H-Pyran,2,2,3,3,4,4,5,5,6-nonafluorotetrahydro- | Zapevalova, T. B.; Plashkin, V. S.; Selishchev, B. N.; Bil'dinov, K. N.; Shcherbakova, M. S. Zhurnal Organicheskoi Khimii (1977), 13(12), 2573-4. |

General schemes for the synthesis of halogenated compounds, including the anesthesia compounds are provided, e.g., in Chambers, "Fluorine in Organic Chemistry." Wiley Blackwell, 2004. ISBN:978-1405107877; Iskra, "Halogenated Heterocycles: Synthesis, Application and Environment (Topics in Heterocyclic Chemistry)." Springer, 2012. ISBN:978-3642251023; and Gakh, and Kirk, "Fluorinated Heterocycles" (ACS Symposium Series). American Chemical Society, 2009. ISBN:978-0841269538.

Halogenated Alcohols

Synthesis schemes for halogenated alcohols are summarized in Table 4 and can be applied to the synthesis of the halogenated alcohol anesthetic compounds described herein, including those of Formula I. Illustrative references describing synthesis of halogenated alcohols include without limitation, e.g., Mochalina, et al., *Akademii Nauk SSSR* (1966), 169(6), 1346-9; Delyagina, et al., *Akademii Nauk SSSR, Seriya Khimicheskaya* (1972), (2), 376-80; Venturini, et al., *Chimica Oggi* (2008), 26(4), 36-38; Navarrini, et al., *Journal of Fluorine Chemistry* (2008), 129(8), 680-685; Adcock, et al., *Journal of Fluorine Chemistry* (1987), 37(3), 327-36; Cantini, et al., Ital. Appl. (2007), IT 2007MI1481 A1 20071023; Marraccini, et al., Eur. Pat. Appl. (1990), EP 404076 A1; Adcock, et al., *Journal of Organic Chemistry* (1973), 38(20), 3617-18; Aldrich, et al., *Journal of Organic Chemistry* (1964), 29(1), 11-15; Weis, et al., *Industrial & Engineering Chemistry Research* (2005), 44(23), 8883-8891; Arimura, et al., *Journal of Chemical Research. Synopses* (1994), (5), 202-3; Du, et al., *Journal of the American Chemical Society* (1990), 112(5), 1920-6; Galimberti, et al., *Journal of Fluorine Chemistry* (2005), 126(11-12), 1578-1586; and Navarrini, et al., Eur. Pat. Appl. (2004), EP 1462434 A1. Generally, fluorinated alcohols can be synthesized using techniques of direct hypofluorite addition and reverse hypofluorite addition, described, e.g., in Navarrini, et al., *Journal of Fluorine Chemistry* (2008), 129(8), 680-685.

In a typical direct hypofluorite addition, a stream of hypofluorite is bubbled into a solution of an olefin maintained at the desired temperature in a semi-batch method in order to operate in excess of olefin. The addition reactor can be standard dimensions designed 250 ml American Iron and Steel Institute (AISI) 316 stainless steel cooled by an external vessel. The reactor can be realized with a discharge bottom valve and two feeding tubes. The reactor's head can be equipped with: an outgoing tube for collecting the off-gas stream and a mechanical/magnetic transmission stirring system. The feed of the addition reactor and the off-gases can be analysed on-line, e.g., via infrared (IR), gas chromatography-thermal conductivity detector (GC-TCD) and gas chromatography-infrared (GC-IR). At the end of the addition, the reactor can be stripped with 4 nL/h of helium for about 30 min, the vessel is unloaded and the resulting mixture analysed, e.g., via gas chromatography (GC), GC-mass spectrometry (MS) e nuclear magnetic resonance (NMR) $^{19}$F. The raw reaction mixture can be distilled in vacuum or at atmospheric pressure.

In a typical reverse hypofluorite addition, a stream of olefin is bubbled into a solution of hypofluorite in order to operate in excess of hypofluorite at the desired temperature. The reaction can be carried out in a continuous stirred-tank reactor (CSTR) with a continuous feed of both the reagents. The reactor is charged with the solvent, cooled at the desired temperature and a gaseous stream comprising $CF_3OF$ (2.35 nL/h), He (2.5 nL/h), $COF_2$ (0.3 nL/h) is fed in the reactor (e.g., for about 12 min) before starting to add the olefin. After adding the olefin, for safety reasons it is compulsory to eliminate the residual hypofluorite before opening the reactor. In order to remove the majority of the overloaded hypofluorite from the bulk, the liquid phase can be stripped with a stream of 4 nL/h of helium for about 30 min at the temperature between −80 and −90° C., after that maintaining the temperature in the range −80 to −90° C. about 2 ml of CFCl═CFCl can be added in the reactor to eliminate the remaining traces of hypofluorite. The traces of $CF_3OF$ react completely with $CFCl=CFCl$ producing $CF_3O—CFCl—CF_2Cl$.

Halogenated Cyclopentanes and Cyclohexanes

Synthesis schemes for halogenated cyclopentanes and cyclohexanes are summarized in Table 4 and can be applied to the synthesis of the halogenated cyclopentane and cyclohexane anesthetic compounds described herein, including those of Formulae V and VI. Illustrative references describing synthesis of halogenated cyclopentanes and halogenated cyclohexanes include without limitation, e.g., Imura, et al., *Jpn. Kokai Tokkyo Koho* (2001), JP 2001261594A; Heitzman, et al., *Journal of the Chemical Society* (1963), 281-9; Sekiya, Akira; et al., PCT Int. Publ. WO 96/00707 A1, Sekiya, et al., *Jpn. Kokai Tokkyo Koho* (1996), JP 08143487 A; Rao, et al, PCT Int. Publ. WO 93/05002 A2; Burdon, et al., *Journal of the Chemical Society* (1965), (April), 2382-91; Yamada, et al., *Jpn. Kokai Tokkyo Koho* (1999), JP 11292807 A; Otsuki, *Petrotech* (Tokyo, Japan) (2005), 28(7), 489-493; Takada, et al., *Jpn. Kokai Tokkyo Koho* (2002), JP 2002241325 A; Suzuki, et al., *Jpn. Kokai Tokkyo Koho* (2001), JP 2001247494 A; Sekiya, et al., *Jpn. Kokai Tokkyo Koho* (2001), JP 2001240567 A; Kim, et al., *Jpn. Kokai Tokkyo Koho* (2001), JP 2001240569 A; Sakyu, et al., *Jpn. Kokai Tokkyo Koho* (2000), JP 2000247912 A; Saku, et al, *Jpn. Kokai Tokkyo Koho* (2000), JP 2000226346 A; Yamada, et al., PCT Int. Publ. WO 99/50209 A1; Yamada, et al., PCT Int. Publ. WO 99/33771 A1; Sekiya, et al., PCT Int. Publ. WO 98/51650 A1; Banks, et al., *Journal of the Chemical Society [Section]C: Organic* (1968), (5):548-50; Stepanov, et al., *Russian Journal of Organic Chemistry* (2010), 46(9): 1290-1295; Saku, et al., Jpn. Kokai Tokkyo Koho (2000), JP 2000226346 A; Sekiya, et al., PCT Int. Publ. WO 98/51650 A1; Sekya, et al., *Jpn. Kokai Tokkyo Koho* (1996), JP 08143487 A; Yamada, et al., PCT Int. Publ. WO 94/07829 A1; Anton, PCT Int. Publ. WO 91/13846 A1; Bielefeldt, et al., Eur. Pat. Appl. (1991), EP 442087 A1; Bielefeldt, et al., Ger. Offen. (1989), DE 3735467 A1; and Evans, et al., *Journal of the Chemical Society* (1963), (October), 4828-34. Generally, fluorinated cyclopentanes and fluorinated cyclohexanes can be synthesized using techniques described, e.g., in Evans, et al., *Journal of the Chemical Society* (1963), (October), 4828-34; Burdon, et al., *Journal of the Chemical Society* (1965), (April), 2382-91.

A halogenated cyclopentane or halogenated cyclohexane can be synthesized by reduction of a halogenated cycloalkene with lithium aluminum hydride, as described, for example, by Evans, et al., *Journal of the Chemical Society* (1963), (October), 4828-34. In this approach, a (poly)fluorocycloalkene is mixed with lithium aluminum hydride in ether, producing several species of (poly)fluorocycloalkenes in an addition-elimination process. These (poly)fluorocycloalkenes can be characterized and several (poly)fluorocycloalkanes and related compounds can be made from them. Elimination is the most important reaction of such systems, and a possible pathway for a cis-E2-process. For reaction of the polyfluorocycloalkene with lithium aluminum anhydride, the (poly)fluorocycloalkene is added dropwise to a stirred suspension of lithium aluminum hydride in diethyl ether at −20° C. When the initial reaction subsides, the solution is refluxed, then cooled to −20° C. and 50% v/v sulphuric acid is added dropwise, followed by water until no precipitate remained. The dried ($MgSO_4$) ethereal solution is evaporated through a vacuum-jacketed column (1'×1½") packed with glass helices to leave a mixture of (poly) fluorocycloalkenes (180 g.) which is separated by preparative gas chromatography (column type B, 100° C., $N_2$ flow-rate 60 l./hr.). 1H-Nonafluorocyclohexene prepared in this way contained a trace of ether which can be removed by a second gas-chromatographic separation in a column of type A packed with tritolyl phosphate-kieselguhr (1:3). The double bond of the (poly)fluorocycloalkenes can be readily saturated, e.g., by fluorination with cobaltic fluoride, or by catalytic hydrogenation at atmospheric pressure to produce the corresponding desired (poly)fluorocycloalkane. Characterization of the (poly)fluorocycloalkenes (poly)fluorocloalkanes can be performed using standard methodologies, including, e.g., oxidation, NMR spectroscopy, mass spectroscopy, resistance to alkali, and gas chromatography.

The vapour-phase fluorination of a cycloalkadiene with cobaltic fluoride to produce the corresponding (poly)fluorocycloalkane and the alternative synthesis of the (poly) fluorocycloalkane starting from a (poly)fluorocycloalkene, fluorinating with cobaltic fluoride and then reducing with lithium aluminum hydride are described, for example, by Heitznman, et al., *Journal of the Chemical Society* (1963), 281-9. For vapour-phase fluorination of a cycloalkadiene, the cycloalkadiene is fed into a reactor containing cobalt trifluoride maintained at 190° C.-250° C. The products are collected in a copper trap cooled by solid carbon dioxide and any remaining in the reactor is swept into the trap by a gentle stream of nitrogen. The total product is poured into ice-water and washed with sodium hydrogen carbonate solution. The clear organic layer is separated, and a resin discarded. The combined products are distilled through a vacuum-jacketed column (4'×1") packed with Dixon gauze rings (1/16"×1/16"). The distillation is controlled by analytical gas chromatography. For synthesis of the (poly)fluorocycloalkanes the corresponding (poly)fluorocycloalkenes, the (poly)fluorocycloalkene is first chlorinated and then reduced. For chlorination, the olefin and liquid chlorine are irradiated with ultraviolet light for 4 hr. in a quartz flask fitted with a condenser at −78° C. The excess of chlorine is removed by washing the products with aqueous sodium hydrogen carbonate (10% w/v). The (poly)chlorofluorocycloalkane product is dried ($P_2O_5$) and distilled, and can be analyzed by gas chromatography and infrared spectroscopy. For reduction, the (poly)chlorofluorocycloalkane product in dry ether is added to a stirred suspension of lithium aluminum hydride in dry ether at 0° C. The apparatus is fitted with a condenser cooled to −78° C. After 5 hours' stirring at 15° C., unchanged lithium aluminum hydride is destroyed at 0° C. by the careful addition of water followed by hydrochloric acid (10% v/v) to dissolve the solid. The ethereal layer is distilled through a column (2'×¼") and the residue can be analyzed by gas chromatography and infrared spectroscopy.

The synthesis of (poly)fluorocycloalkanes by addition of chlorine to the corresponding (poly)fluorocycloalkene, followed by lithium aluminum hydride reduction is described, for example, by Burdon, et al., *Journal of the Chemical Society* (1965), (April), 2382-91. For chlorination, the (poly) fluorocycloalkene is mixed with an excess of chlorine in the presence of ultraviolet irradiation. For reduction, the (poly) chlorofluorocycloalkane in dry ether are added over 2 hr. to a stirred solution of lithium aluminum hydride in dry ether at 0° C. The reaction mixture is stirred for a further 2 hr., and then the excess of lithium aluminum hydride is destroyed in the usual way with 50% sulphuric acid. Distillation of the dried ($MgSO_4$) ether layer through a 6 in. column packed with glass helices leaves a residue. The species in the residue can be separated by gas chromatography on a preparative scale [e.g., column 4.8 m.×35 mm. diam., packed with dinonyl phthalate-kieselguhr (1:2); temp. 98° C. $N_2$, flow-rate 11 l./hr.]. The eluted components can be analyzed by infrared spectroscopy (IR) and/or NMR.

Halogenated Dioxanes

Synthesis schemes for halogenated dioxanes are summarized in Table 4 and can be applied to the synthesis of the halogenated dioxane anesthetic compounds described herein, including those of Formula III. Illustrative references describing synthesis of halogenated dioxanes include without limitation, e.g., Krespan, et al., PCT Int. Appl. (1991), WO 91/04251; Krespan, et al., Journal of Organic Chemistry (1991), 56(12), 3915-23; Coe, et al., Journal of Fluorine Chemistry (1975), 6(2), 115-28; Burdon, et al., U.S. Pat. No. 3,883,559; Burdon, et al., Tetrahedron (1971), 27(19), 4533-51; Adcock, et al., Journal of Fluorine Chemistry (1980), 16(3), 297-300; Dodman, et al., Journal of Fluorine Chemistry (1976), 8(3), 263-74; Meinert, et al., Journal of Fluorine Chemistry (1992), 59(3), 351-65; Berenblit, et al., Zhurnal Prikladnoi Khimii (Sankt-Peterburg, Russian Federation) (1980), 53(4), 858-61; Lagow, et al., U.S. Pat. No. 4,113,435; Berenblit, et al., Zhurnal Prikladnoi Khimii (Sankt-Peterburg, Russian Federation) (1975), 48(10), 2206-10; Adcock, et al., Journal of Organic Chemistry (1975), 40(22), 3271-5; Abe, et al., Jpn. Tokkyo Koho (1974), JP 49027588B; Berenblit, et al. Zhurnal Organicheskoi Khimii (1974), 10(10), 2031-5; Adcock, et al., Journal of the American Chemical Society (1974), 96(24), 7588; Abe, et al., Bulletin of the Chemical Society of Japan (1973), 46(8), 2524-7; and Sianesi, et al., Ger. Offen. (1972), DE 2111696A. Generally, fluorinated dioxanes can be synthesized by fluorinating dioxanes over cobalt trifluoride ($CoF_3$) or over potassium tetrafluorocobaltate, for example, as described in Burdon, et al., Tetrahedron (1971), 27(19), 4533-51. Polyfluorodioxenes generally can be synthesized by dehydrofluorination of the appropriate polyfluorodioxane, for example, as described in Coe, et al., Journal of Fluorine Chemistry (1975), 6(2), 115-28.

In a typical fluorination of dioxane over $CoF_3$, as described, e.g., by Burdon, et al., Tetrahedron (1971), 27(19), 4533-51, dioxane is passed into a stirred bed of $CoF_3$ (apparatus has been described in Bohme, Br. Dtsch. Chem. Ges. 74:248 (1941) and Bordwell, et al., J Amer Chem Soc 79:376 (1957) at 100° C. in a stream of $N_2$ (10 dm$^3$/hr). After all the dioxane enters the reactor (about 3 hrs), the $N_2$ stream is continued for a further 2 hr. The products are trapped at −78° C. and poured into iced water. Separation gives a pale yellow liquid which deposits crystals of a tetrafluorodioxane on being stored at −60° C. The products from multiple (e.g., four) such fluorinations are washed with aqueous $NaHCO_3$ and distilled from $P_2O_5$ up a 2' vacuum jacketed glass column packed with Dixon gauze rings ($\frac{1}{16}$"×$\frac{1}{16}$"). The fractions collected can be further separated, e.g., by analytical gas-liquid chromatography (GLC) and analyzed, e.g., by GLC, IR, MS and/or NMR.

In a typical fluorination of dioxane over $KCoF_4$, as described, e.g., by Burdon, et al., Tetrahedron (1971), 27(19), 4533-51, dioxane is passed in a stream of $N_2$ (10 dm$^3$/hr) over a heated (230° C.) and stirred bed of $KCoF_4$ (the apparatus has been described in Burdon, et al., J. Chem Soc. 2585 (1969)). The addition takes about 3 hr., and the $N_2$ stream is continued for 2 hr. afterwards. The products are collected in a copper trap cooled to −78° C.; washed with water and dried to give crude material. The crude product, or a sample thereof, can be further separated, e.g., by analytical gas-liquid chromatography (GLC) and analyzed, e.g., by GLC, IR, MS and/or NMR.

In a typical isomerization of the polyfluorodioxanes over $AlF_3$, as described, e.g., by Burdon, et al., Tetrahedron (1971), 27(19), 4533-51, dioxane is passed in a stream of $N_2$ (1.5 dm$^3$/hr) through a heated (temp stated in each case) glass tube (12"×$\frac{3}{4}$") packed with $AlF_3$, powder supported on glass chips. The products are collected in a trap cooled in liquid air. The polyfluorodioxans are isomerized at elevated temperatures in the range of about 390° C. to about 490° C. The isomerized products can be further separated, e.g., by analytical gas-liquid chromatography (GLC) and analyzed, e.g., by GLC, IR and/or NMR.

Halogenated Dioxolanes

Synthesis schemes for halogenated dioxolanes are summarized in Table 4 and can be applied to the synthesis of the halogenated dioxolane anesthetic compounds described herein, including those of Formula IV. Illustrative references describing synthesis of halogenated dioxolanes include without limitation, e.g., Kawa, et al., Jpn. Kokai Tokkyo Koho (2000), JP 2000143657A; Russo, et al., Eur. Pat. Appl. (1999), EP 937720 A1; Russo, et al., Journal of Fluorine Chemistry (2004), 125(1), 73-78; Navarrini, et al., Journal of Fluorine Chemistry (1995), 71(1), 111-17; Navarrini, et al., Eur. Pat. Appl. (1992), EP 499158A; Navarrini, et al., Eur. Pat. Appl. (1995), EP 683181 A1; Muffler, et al., Journal of Fluorine Chemistry (1982), 21(2), 107-32; Anton, et al., PCT Int. Appl. (1991), WO 9109025 A2; Berenblit, et al., Zhurnal Organicheskoi Khimii (1974), 10(10), 2031-5; Berenblit, et al., Zhurnal Prikladnoi Khimii (Sankt-Peterburg, Russian Federation) (1975), 48(10), 2206-10; Prager, Journal of Organic Chemistry (1966), 31(2), 392-4; Throckmorton, Journal of Organic Chemistry (1969), 34(11), 3438-40; Sianesi, et al., Ger. Offen. (1972), DE 2111696 A; and Navarrini, et al., Eur. Pat. Appl. (1991), EP460948A2. Generally, fluorinated dioxolanes can be synthesized by addition of bis-(fluoroxy)difluoromethane (BDM) to halogenated alkenes, e.g., as described by Navarrini, et al., J Fluorine Chem 71:111-117 (1995) or by reaction of chloroalkoxyfluorocarbonyl halides or ketones with fluoride ions, e.g., as described by Muffler, et al., J Fluorine Chem 21:107-132 (1982).

In a typical reaction for addition of bis-(fluoroxy)difluoromethane (BDM) to halogenated alkenes, e.g., as described by Navarrini, et al., J Fluorine Chem 71:111-117 (1995), a semi-continuous or continuous system can be used. In a general procedure for a semi-continuous system, a glass reactor equipped with a mechanical stirrer, reflux condenser, thermocouple, inner plunging pipes, maintained at temperatures in the range of about −196° C. to 25° C. (see, Table 1 of Navarrini, et al., supra) is charged with a 0.2-5 M solution (50-300 ml) of the olefin in $CFCl_3$, $CF_2Cl_2$ or with the pure olefin. A flow of bis(fluoroxy)difluoromethane (usually about 1 liter per hour flow rate) diluted with He in a 1:5 ratio is then fed into the reactor until 90% of the olefin is converted. At the end of the addition, helium is bubbled through the reaction mixture to remove traces of unreacted $CF_2(OF)_2$. The dioxolanes are isolated via fractional distillation using an HMS 500 C Spaltrohr Fischer apparatus. In a general procedure for a continuous system, bis(fluoroxy) difluoromethane at a flow rate of about 0.4 liters per hour diluted with He (about 2 liters per hour) and the olefin (36 mmol per hour) are simultaneously but separately fed, at the temperatures in the range of about −196° C. to 25° C. (see, Table 1 of Navarrini, et al., supra), into a multi-neck glass reactor containing a $10^{-1}$ to $10^{-2}$ M solution of the olefin and equipped with a magnetic entrainment mechanical stirrer, reflux cooler, thermocouple and inner plunging pipes. After feeding the reagents for 4 hr, helium is bubbled through the reaction mixture to remove traces of unreacted $CF_2(OF)_2$. The reaction mixture can be purified by fractional distillation. The reaction products can be separated through traps cooled to −50° C., −80° C., −100° C., −120° C. and −196° C., as appropriate. Further distillation of the mixtures collected at −100° C. to −120° C. through traps cooled to −50° C., −60° C., −75° C., −100° C., −105° C., −112° C., −120° C. and −196° C., respectively, allows collection of the pure dioxolane, e.g., in the −75° C., −100° C., −112° C. traps. The collected dioxolane product can be analyzed, e.g., by GLC, IR, MS and/or NMR.

Halogenated Pyrans

Synthesis schemes for halogenated pyrans are summarized in Table 4 and can be applied to the synthesis of the halogenated tetrahydropyran anesthetic compounds described herein, including those of Formula VII. Illustrative references describing synthesis of halogenated pyrans include without limitation, e.g., Abe, et al., *Journal of Fluorine Chemistry* (1979), 13(6), 519-30; Abe, et al., *Journal of Fluorine Chemistry* (2005), 126(3), 325-332; Jpn. Kokai Tokkyo Koho (1980), JP 55051084 A; Abe, et al., *Journal of Fluorine Chemistry* (1979), 13(6), 519-30; Abe, et al., *Journal of Fluorine Chemistry* (1978), 12(1), 1-25; GB Pat. No. 862538; Sander, et al., (1959), DE 1069639; GB Pat No. 718318; Abe, et al., *Journal of Fluorine Chemistry* (1979), 13(6), 519-30; Abe, et al., *Bulletin of the Chemical Society of Japan* (1976), 49(7), 1888-92; Wang, *Organic Reactions* (Hoboken, N.J., United States) (1985), vol. 34; Dmowski, et al., *Polish Journal of Chemistry* (1978), 52(1), 71-85; Hasek, et al., *Journal of the American Chemical Society* (1960), 82, 543-51; Abe, et al., *Journal of Fluorine Chemistry* (2005), 126(3), 325-332; Moldavsky, et al., *Journal of Fluorine Chemistry* (1998), 87(1), 111-121; Nishimura, et al., *Jpn. Kokai Tokkyo Koho* (1989), JP 01249728 A; Nishimura, Eur. Pat. Appl. (1988), EP 271272 A2; Abe, et al., *Journal of Fluorine Chemistry* (1979), 13(6), 519-30; De Pasquale, *Journal of Organic Chemistry* (1973), 38(17), 3025-30; Abe, et al., *Jpn. Tokkyo Koho* (1973), JP 48012742 B; Henne, et al., *Journal of the American Chemical Society* (1952), 74, 5420-2; Kauck, et al., (1952), U.S. Pat. No. 2,594,272; and Zapevalova, et al., *Zhurnal Organicheskoi Khimii* (1977), 13(12), 2573-4. Generally, fluorinated pyrans can be synthesized by reducing to a diol a perfluorinated dibasic ester, cyclizing the diol to an ether, chlorinating the cyclic ether to produce a perhalogenated cyclic ether, and then fluorinating the perhalogenated cyclic ether to produce the desired perfluorinated cyclic ether. Typically, for reduction of a perfluorinated dibasic ester to a diol, the perfluorinated dibasic ester is reduced with $LiAlH_4$ in dry ether to give the diol. The diol can be recrystallized, e.g., from benzene. For cyclization, a mixture of the glycol and concentrated sulfuric acid (10 g. or 0.1 mole) is kept in an oil bath at a temperature in the range of about 185° C. to about 250° C. The cyclic ether which distilled over can be dried, e.g., with Drierite, and redistilled. For chlorination of the cyclic ether, the cyclic ether is placed in a quartz flask illuminated with a sun lamp or UV lamp. Chlorine is bubbled through for two days. An ice-cooled trap attached to the reflux condenser caught entrained material, which is returned from time to time. For fluorination of the cyclic ether to produce the perfluorinated cyclic ether, the cyclic ether and $SbF_3Cl_2$ are heated at 155° C. for 24 hours in a steel bomb. The pressure rises to about 230 p.s.i. and drops to about 50 p.s.i. on cooling to room temperature. This pressure is released into a Dry Ice trap which collects raw perfluorinated cyclic ether. For larger rings, a two-step procedure may be applied. The cyclic ether and $SbF_3Cl_2$ are heated to 125° C. for seven hours in a 450 ml. steel bomb, with shaking. The pressure rises to about 75 p.s.i. The temperature is raised to 160° C. for 16 hours, which raises pressure to 280 p.s.i. After cooling, a light fraction is collected by distillation. The light fraction and $SbF_3Cl_2$ are shaken at 160° C. for five hours in a bomb. The pressure rises to about 320 p.s.i. After cooling, repeated distillation of the crude product gives the desired perfluorinated cyclic ether. This perfluorinated cyclic ether can be purified by passage through two 10% HCl bubblers to remove traces of antimony salts, concentrated $H_2SO_4$ to remove unsaturated impurities and finally distilled from $P_2O_5$. The purified material can be analyzed, e.g., by GLC, IR, MS and/or NMR.

Halogenated Furans

Synthesis schemes for halogenated furans are summarized in Table 4 and can be applied to the synthesis of the halogenated tetrahydrofuran anesthetic compounds described herein, including those of Formula VI. Illustrative references describing synthesis of halogenated furans include without limitation, e.g., Chepik, et al., *Izvestiya Akademii Nauk SSSR, Seriya Khimicheskaya* (1991), (11), 2611-18; Abe, et al., *Journal of Fluorine Chemistry* (1979), 13(6), 519-30; Abe, et al., *Jpn. Kokai Tokkyo Koho* (1978), JP53025552A; Abe, et al., *Jpn. Tokkyo Koho* (1976), JP 51045594 B; Abe, et al., *Jpn. Kokai Tokkyo Koho* (1976), JP 51082257 A; Abe, et al., *Jpn. Kokai Tokkyo Koho* (1975), JP 50106955 A; Abe, et al., *Jpn. Tokkyo Koho* (1973), JP 48012742 B; *Jpn. Kokai Tokkyo Koho* (1981), JP 56142877 A.; Abe, et al., Journal of Fluorine Chemistry (1979), 13(6), 519-30; Abe, et al., *Jpn. Kokai Tokkyo Koho* (1978), JP 53124259 A; Burdon, et al., *Journal of Fluorine Chemistry* (1991), 51(2), 179-96; and Abe, et al., *Bulletin of the Chemical Society of Japan* (1976), 49(7), 1888-92. Generally, fluorinated furans can be produced, e.g., by electrochemical fluorination or by exposure of a tetrahydrofuran to tetrafluorocobaltate(III) and/or cobalt trifluoride.

A typical electrochemical fluorination reaction is described, e.g., by Abe and Nagase, *J Fluorine Chem* 13:519-530 (1979). An electrolytic cell that can be used is described in Abe, et al., *J Fluorine Chem* 12:1 (1978); and Abe, et al., *J Fluorine Chem* 12:359 (1976). The compound (e.g., furan) to be fluorinated is charged into the cell which contained 1 liter electrochemically purified anhydrous hydrogen fluoride, and the resulting solution is subjected to fluorination with an anodic current density of 3.5 $A/dm^2$, a cell voltage of 5.0~6.2 V, and a cell temperature of about 5-6° C. over a period of 437 min (234 Ahr) until the cell voltage rose rapidly up to 9.0 V. Initially, the products collected in cold traps (−196° C.) are roughly separated into at least two fractions using the traps of a low-temperature distillation unit. After that, the composition of products in these fractions can be can be further separated, e.g., by analytical gas-liquid chromatography (GLC) and analyzed, e.g., by GLC, IR, MS and/or NMR.

Typical reactions for fluorination by tetrafluorocobaltate (III) and/or cobalt trifluoride are described, e.g., in Burdon, et al., *Journal of Fluorine Chemistry* (1991), 51(2), 179-96. For fluorination by Potassium Tetrafluorocobaltate(III) a tetrahydrofuran is passed through a standard stirred reactor (1.2 m×15 cm i.d.; 6 Kg $KCoF_4$) at 200° C., during 3 hours. The reactor is purged with nitrogen (15 liters per hour for 1.5 h), and the trap contents are washed with water. The dried crude product can be analyzed, e.g., by GLC, IR, MS and/or NMR. For fluorination by cobalt trifluoride, crude product is passed via a liquid seal into a similar reactor (1.3 m×18 cm i.d.; packed with 10 Kg of $CoF_3$) during 3 h. Temperatures are maintained in the range of about 120-150° C. Following a nitrogen sweep (25 liters per hour for 2 h) the contents of the cold trap (−78° C.) are poured onto ice and washed with water. The combined products are washed (aqueous sodium bicarbonate then water) and dried (MgSO$_4$ then P$_2$O$_5$). A part can be fractionally distilled through a 1 m vacuum-jacketed spinning band column, with analysis by GLC. Fractions obtained can be further separated by preparative GLC (e.g., Pye Series 104 machine, with a flame-ionization detector; tube packings, Ucon L.B. 550X on Chromasorb P 30-60 (1:4); analysis tube, 1.7 m×4 mm i.d.; semi-preparative tube, 9.1 m×7 mm i.d.) to give a pure sample of each product. As appropriate or desired, the fluorinated products can be isomerized. The apparatus used for isomerization can be an electrically-heated hard glass tube (320 mm×25 mm i.d.), packed with a 1:1 mixture of aluminium fluoride and small glass spheres. Before use, this is heated to 280° C. for 24 h, whilst a slow stream of nitrogen is passed through. With the tube temperature at 420° C., the fluorinated product is passed through during 30 min. in a stream of nitrogen. Isomerized and non-isomerized products can be further separated, e.g., by analytical gas-liquid chromatography (GLC) and analyzed, e.g., by GLC, IR, MS and/or NMR.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of inducing anesthesia in a subject, comprising administering to the subject via the respiratory system an effective amount of a compound or a mixture of compounds of Formula I:

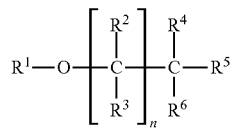

wherein:
n is 0-4,
R$^1$ is H;
R$^2$, R$^3$, R$^4$, R$^5$ and R$^6$ independently are selected from H, X, CX$_3$, CHX$_2$, CH$_2$X and C$_2$X$_5$; and
wherein X is a fluorine, the compound having a vapor pressure of at least 0.1 atmospheres (76 mmHg) at 25° C., and the number of hydrogen atoms in Formula I do not exceed the number of carbon atoms, thereby inducing anesthesia in the subject.

2. The method of claim 1, wherein the compound is selected from the group consisting of:
a) 1-Butanol, 4,4,4-trifluoro-3,3-bis(trifluoromethyl)- (CAS#14115-49-2);
b) 1-Butanol, 1,1,2,2,3,3,4,4,4-nonafluoro- (CAS#3056-01-7);
c) 1-Butanol, 2,2,3,4,4,4-hexafluoro-3-(trifluoromethyl)- (CAS#782390-93-6);
d) 1-Butanol, 3,4,4,4-tetrafluoro-3-(trifluoromethyl)- (CAS#90999-87-4);
e) 1-Pentanol, 1,1,4,4,5,5,5-heptafluoro- (CAS#313503-66-1); and
f) 1-Pentanol, 1,1,2,2,3,3,4,4,5,5,5-undecafluoro- (CAS#57911-98-5).

3. The method of claim 2, wherein the compound is 1-Butanol, 4,4,4-trifluoro-3,3-bis(trifluoromethyl)- (CAS#14115-49-2).

4. The method of claim 2, wherein the compound is 1-Butanol, 1,1,2,2,3,3,4,4,4-nonafluoro- (CAS#3056-01-7).

5. The method of claim 2, wherein the compound is 1-Butanol, 2,2,3,4,4,4-hexafluoro-3-(trifluoromethyl)- (CAS#782390-93-6).

6. The method of claim 2, wherein the compound is 1-Butanol, 3,4,4,4-tetrafluoro-3-(trifluoromethyl)- (CAS#90999-87-4).

7. The method of claim 2, wherein the compound is 1-Pentanol, 1,1,4,4,5,5,5-heptafluoro- (CAS#313503-66-1).

8. The method of claim 2, wherein the compound is 1-Pentanol, 1,1,2,2,3,3,4,4,5,5,5-undecafluoro- (CAS#57911-98-5).

9. The method of claim 2, wherein the compound is administered at a dose sufficient to achieve a desired anesthetic endpoint, the desired anesthetic endpoint selected from the group consisting of general anesthesia, sedation, tranquilization, immobility, amnesia, analgesia, unconsciousness and autonomic quiescence.

10. The method of claim 2, wherein the subject is a mammal.

11. A method of inducing anesthesia in a subject, comprising administering to the subject an effective amount of a compound or a mixture of compounds of Formula I:

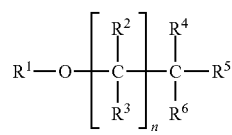

wherein:
n is 0-4,
R$^1$ is H;
R$^2$, R$^3$, R$^4$, R$^5$ and R$^6$ independently are selected from H, X, CX$_3$, CHX$_2$, CH$_2$X and C$_2$X$_5$; and
wherein X is a fluorine, the compound having a vapor pressure of at least 0.1 atmospheres (76 mmHg) at 25° C., and the number of hydrogen atoms in Formula I do not exceed the number of carbon atoms, thereby inducing anesthesia in the subject.

12. The method of claim 11, wherein the compound is selected from the group consisting of:
a) 1-Butanol, 4,4,4-trifluoro-3,3-bis(trifluoromethyl)- (CAS#14115-49-2);
b) 1-Butanol, 1,1,2,2,3,3,4,4,4-nonafluoro- (CAS#3056-01-7);
c) 1-Butanol, 2,2,3,4,4,4-hexafluoro-3-(trifluoromethyl)- (CAS#782390-93-6);
d) 1-Butanol, 3,4,4,4-tetrafluoro-3-(trifluoromethyl)- (CAS#90999-87-4);
e) 1-Pentanol, 1,1,4,4,5,5,5-heptafluoro- (CAS#313503-66-1); and
f) 1-Pentanol, 1,1,2,2,3,3,4,4,5,5,5-undecafluoro- (CAS#57911-98-5).

13. The method of claim 12, wherein the administering comprises administering by any route sufficient to achieve a desired anesthetic effect.

14. The method of claim 13, wherein the compound is 1-Butanol, 4,4,4-trifluoro-3,3-bis(trifluoromethyl)- (CAS#14115-49-2).

15. The method of claim 13, wherein the compound is 1-Butanol, 1,1,2,2,3,3,4,4,4-nonafluoro- (CAS#3056-01-7).

16. The method of claim 13, wherein the compound is 1-Butanol, 2,2,3,4,4,4-hexafluoro-3-(trifluoromethyl)- (CAS#782390-93-6).

17. The method of claim 13, wherein the compound is 1-Butanol, 3,4,4,4-tetrafluoro-3-(trifluoromethyl)- (CAS#90999-87-4).

18. The method of claim 13, wherein the compound is 1-Pentanol, 1,1,4,4,5,5,5-heptafluoro- (CAS#313503-66-1).

19. The method of claim 13, wherein the compound is 1-Pentanol, 1,1,2,2,3,3,4,4,5,5,5-undecafluoro- (CAS#57911-98-5).

20. The method of claim 13, wherein the compound is administered at a dose sufficient to achieve a desired anesthetic endpoint, the desired anesthetic endpoint selected from the group consisting of general anesthesia, sedation, tranquilization, immobility, amnesia, analgesia, unconsciousness and autonomic quiescence.

21. The method of claim 12, wherein the subject is a mammal.

22. The method of claim 1, wherein the mammal is a human.

23. The method of claim 21, wherein the mammal is a human.

* * * * *